(12) United States Patent
Smith et al.

(10) Patent No.: US 10,894,948 B2
(45) Date of Patent: Jan. 19, 2021

(54) RESETTING PLURIPOTENT STEM CELLS

(71) Applicant: CAMBRIDGE ENTERPRISE LIMITED, Cambridge, Cambridgeshire (GB)

(72) Inventors: Austin Smith, Cambridge (GB); Ge Guo, Cambridge (GB); Yasuhiro Takashima, Cambridge (GB)

(73) Assignee: CAMBRIDGE ENTERPRISE LIMITED, Cambridge (GB)

(*) Notice: Subject to any disclaimer, the term of this patent is extended or adjusted under 35 U.S.C. 154(b) by 0 days.

(21) Appl. No.: 15/505,707

(22) PCT Filed: Aug. 21, 2015

(86) PCT No.: PCT/GB2015/052431
§ 371 (c)(1),
(2) Date: Feb. 22, 2017

(87) PCT Pub. No.: WO2016/027099
PCT Pub. Date: Feb. 25, 2016

(65) Prior Publication Data
US 2018/0112187 A1    Apr. 26, 2018

(30) Foreign Application Priority Data

Aug. 22, 2014 (GB) .................................. 1414992.6
Aug. 29, 2014 (GB) .................................. 1415368.8

(51) Int. Cl.
*C12N 5/074* (2010.01)
*C12N 5/0735* (2010.01)

(52) U.S. Cl.
CPC ......... *C12N 5/0696* (2013.01); *C12N 5/0606* (2013.01); *C12N 2500/38* (2013.01); *C12N 2500/99* (2013.01); *C12N 2501/065* (2013.01); *C12N 2501/115* (2013.01); *C12N 2501/119* (2013.01); *C12N 2501/15* (2013.01); *C12N 2501/16* (2013.01); *C12N 2501/235* (2013.01); *C12N 2501/415* (2013.01); *C12N 2501/60* (2013.01); *C12N 2501/604* (2013.01); *C12N 2501/605* (2013.01); *C12N 2501/724* (2013.01); *C12N 2501/727* (2013.01); *C12N 2501/73* (2013.01); *C12N 2501/90* (2013.01); *C12N 2501/999* (2013.01); *C12N 2510/00* (2013.01); *C12N 2533/52* (2013.01)

(58) Field of Classification Search
CPC ............................ C12N 5/0696; C12N 5/0606; C12N 2500/38; C12N 2500/99; C12N 2501/065; C12N 2501/115; C12N 2501/119; C12N 2501/15; C12N 2501/16; C12N 2501/235; C12N 2501/415; C12N 2501/60; C12N 2501/604; C12N 2501/605; C12N 2501/724; C12N 2501/727; C12N 2501/73; C12N 2501/90; C12N 2501/999; C12N 2501/00; C12N 2533/52

USPC ......................................................... 435/377
See application file for complete search history.

(56) References Cited

U.S. PATENT DOCUMENTS

| 9,074,180 | B2 | 7/2015 | Smith | |
|---|---|---|---|---|
| 9,580,686 | B2 | 2/2017 | Buhring | |
| 2011/0088107 | A1* | 4/2011 | Hanna | A01K 67/0271 800/21 |
| 2012/0046346 | A1* | 2/2012 | Rossi | C12N 15/111 514/44 R |
| 2012/0270313 | A1* | 10/2012 | Paul | C07D 403/04 435/354 |
| 2014/0220681 | A1* | 8/2014 | Valamehr | C12N 5/0696 435/366 |
| 2014/0315301 | A1* | 10/2014 | Hanna | C12N 5/0611 435/366 |

FOREIGN PATENT DOCUMENTS

| WO | 2010/077955 A2 | 7/2010 |
|---|---|---|
| WO | 2011/084747 A2 | 7/2011 |
| WO | 2014/174470 A1 | 10/2014 |
| WO | 2016/016894 A1 | 2/2016 |
| WO | 2016/055519 A1 | 4/2016 |
| WO | 2016/079146 A1 | 5/2016 |
| WO | 2016/148253 A1 | 1/2018 |

OTHER PUBLICATIONS

Sumi et al., Epiblast Ground State Is Controlled by Canonical Wnt/β-Catenin Signaling in the Postimplantation Mouse Embryo and Epiblast Stem Cells, PLOS ONE, vol. 8, Iss. 5, (May 2013), pp. 1-11.*

Theunissen et al., "Systematic Identification of Culture Conditions for Induction and Maintenance of Naive Human Pluripotency", Cell Stem Cell 15(4) 471-487 (2014).

Chan et al., "Induction of a human pluripotent state with distinct regulatory circuitry that resembles preimplantation epiblast", Cell Stem Cell 13(6) 663-675 (2013).

Dutta et at., "Self-renewal versus lineage commitment of embryonic stem cells: protein kinase C signaling shifts the balance", Stem Cells 29(4) 618-628 (2011).

(Continued)

*Primary Examiner* — Jennifer M. H. Tichy
(74) *Attorney, Agent, or Firm* — Nixon Peabody LLP; David S. Resnick; Teresa A. Ptashka

(57) ABSTRACT

The invention provides methods and materials for resetting or sustaining a human stem cell in a "naïve" or "ground" state, based on the use of media including combinations of inhibitors. An example naïve culture medium comprises a PKC inhibitor, a MEK inhibitor. Also provided are methods of obtaining or propagating such cells, cells obtained using these methods, and novel culture media, which can be used in these methods.

Figure 1A:
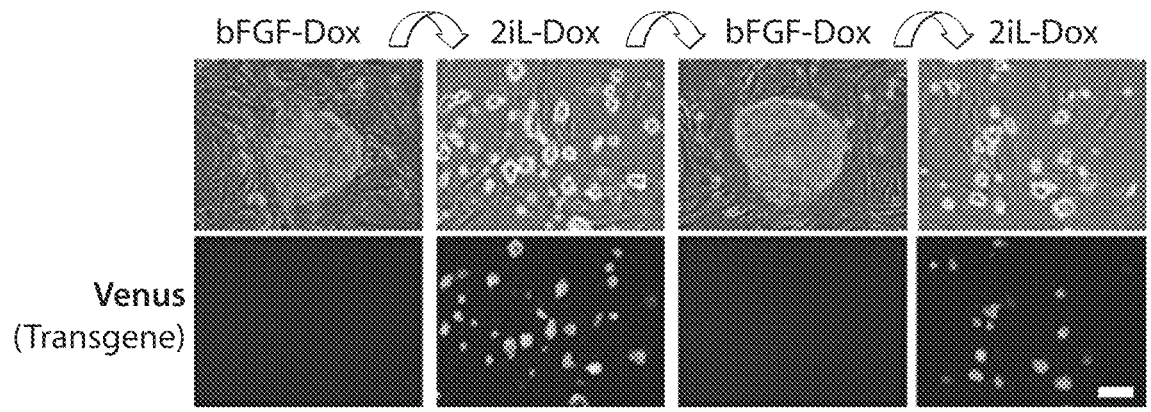

18 Claims, 65 Drawing Sheets
Specification includes a Sequence Listing.

(56) References Cited

OTHER PUBLICATIONS

Guo et al., "Epigenetic resetting of human pluripotency", Development 144(15) 2748-2763 (2017).
Guo et al., "Klf4 reverts developmentally programmed restriction of ground state pluripotency", Development 136(7) 1063-1069 (2009).
Guo et at., "Naive Pluripotent Stem Cells Derived Directly from Isolated Cells of the Human Inner Cell Mass", Stem Cell Reports 6(4) 437-446 (2016).
Theunissen et al., "Systematic Identification of Culture Conditions for Induction and Maintenance of Naive Human Pluripotency", Cell Stem Cell 15(4) 524-526 (2014).
Valahmehr et al., "Platform for induction and maintenance of transgene-free hiPSCs resembling ground state pluripotent stem cells", Stem Cell Reports 2(3) 366-381 (2014).
Wang et al.. "Rapid and efficient reprogramming of somatic cells to induced pluripotent stem cells by retinoic acid receptor gamma and liver receptor homolog 1", Proc Natl Acad Sci USA 108(45) 18283-18288 (2011).
Ware et al., "Derivation of naive human embryonic stem cells", Proc Natl Acad Sci USA 111)12) 4484-4489 (2014).
Zimmerlin et al., "Tankyrase inhibition promotes a stable human naive pluripotent state with improved functionality", Development 143(23) 4368-4380 (2016).
Hao et al., "WUNT/beta-catenin pathway up-regulates Stat3 and converges on LIF to prevent differentiation of mouse embryonic stem cells", Dev Biol 290(1) 81-91 (2006).
Gafni et al., "Derivation of novel human ground state naive pluripotent stem cells." Nature 504:282-286 (2013).
Hanna et al., "Human embryonic stem cells with biological and epigenetic characteristics similar to those of mouse ESCs." PNAS 107(20):9222-9227 (2010).
Rajendran et al., "Inhibition of Protein Kinase C Signaling Maintains Rat Embryonic Stem Cell Pluripotency." Journal of Biological Chemistry 288(34):24351-24362 (2013).
Takashima et al., "Resetting Transcription Factor Control Circuitry toward Ground-State Pluripotency in Human." Cell 158:1254-1269 (2014).
Schoumacher et al. "Inhibiting Tankyrases sensitizes KRAS-mutant cancer cells to MEK inhibitors via FGFR2 feedback signaling" Cancer Research 74(12): 3294-3305 (2014).

* cited by examiner

C and D

3x10^4 cells are seeded on 12 wells and cultured for 7 days with 2DG or reduced glucose.
(with Rock in KSR and without Rock in t2iL+Go)

Figure 17

Sequencing Stats

| BS-seq Sample | Sequencing reads | Mapping Efficiency (%) | Fold coverage (Genome length GRCh37_p13) |
|---|---|---|---|
| Conventional iPSC H91 | 163350819 | 84.9 | 4.17 |
| Conventional iPSC H92 | 156765441 | 85.1 | 4.00 |
| Conventional iPSC 19X | 153635899 | 84.9 | 3.92 |
| Reset cells 19.1 | 154802363 | 67.1 | 3.12 |
| Reset cells 19.2 | 155956363 | 66.0 | 3.09 |
| Reset cells 19.X | 137626880 | 65.8 | 2.72 |

H3K9me3 staining for Mouse ES cells and EpiSC

H3K9me3 staining for Human reset cells in t2iL+Gö

H3K9me3 staining for mEpiSC bFGF/Activin

H3K9me staining for mES cells 2iL

SEQUENCE LISTING

<160> NUMBER OF SEQ ID NOS: 6

<210> SEQ ID NO 1
<211> LENGTH: 21

```
<212> TYPE: DNA
<213> ORGANISM: Artificial sequence
<220> FEATURE:
<223> OTHER INFORMATION: Synthetic primer

<400> SEQUENCE: 1
tggtagcaat ttgaggctct g                                              21

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
atcggcgtct tgacacaac                                                 19

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
aaggacaaga agcgaagcat                                                20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
ttcctgtcat cccctggata                                                20

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
attaccatgg gtcgaggtga                                                20

<210> SEQ ID NO 6
<211> LENGTH: 20
<212> TYPE: DNA
<213> ORGANISM: Artificial sequence
<220> FEATURE:
<223> OTHER INFORMATION: Synthetic primer

<400> SEQUENCE: 6
agaaaagaaa cgagccgtca                                                20
```

RESETTING PLURIPOTENT STEM CELLS

CROSS-REFERENCE TO RELATED APPLICATIONS

This application is a 35 U.S.C. § 371 National Phase Entry Application of International Application No. PCT/GB2015/052431, filed Aug. 21, 2015, which designates the U.S. and which claims priority to GB Application No. 1414992.6, filed Aug. 22, 2014, and GB Application No. 1415368.8, filed Aug. 29, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Feb. 15, 2017, is named 20170222_Sequence_Listing_062915-088930-US.TXT and is 1,441 bytes in size.

TECHNICAL FIELD

The present invention relates to cells in a naïve state, to methods for resetting human pluripotent stem cells to a more naïve state, methods of sustaining cells in a naïve state, to cells obtained by the methods, and to materials used in the methods.

BACKGROUND ART

Stem cell-based technologies have been identified as offering huge potential for therapeutic and non-therapeutic applications.

Human pluripotent stem cells (PSC), whether derived from supernumerary embryos (Reubinoff et al., 2000; Thomson et al., 1998) or by molecular reprogramming (Takahashi et al., 2007; Yu et al., 2007), show several distinguishing characteristics compared with paradigmatic mouse embryonic stem cells (ESC). Originally regarded as inconsequential species-specific features (Thomson et al., 1998), increasing evidence suggests that these differences reflect discrete developmental identities (Rossant, 2008; Smith, 2001). Notably, the derivation of post-implantation epiblast stem cells (EpiSCs) (Brons et al., 2007; Tesar et al., 2007) demonstrates that alternative phenotypes of pluripotent stem cell can be obtained from mice.

Mouse ESC self-renewal is favoured by blockade of fibroblast growth factor (FGF) receptor or downstream mitogen activated protein kinase (Erk) signalling (Burdon et al., 1999; Ying et al., 2008), and is stimulated by the cytokine leukaemia inhibitory factor (LIF) (Smith et al., 1988; Williams et al., 1988). Combining two inhibitors (2i) of the Erk pathway and of glycogen synthase kinase-3 (GSK3) with Leukaemia inhibitory factor (LIF) (2iL) provides a defined culture system that is effective for ESC of all strains of mouse and rat tested, supporting efficient derivation and clonal expansion from dissociated cells (Boroviak et al., 2014; Buehr et al., 2008; Li et al., 2008; Wray et al., 2010; Ying et al., 2008).

This serum- and growth factor-free culture formulation is also highly selective; most cell types, including EpiSC and human PSC, differentiate or die in 2iL alone. The stability and relative homogeneity of ESC in 2iL (Wray et al., 2010) is proposed to represent a developmental ground state closely reflective of the newly formed epiblast in the mature blastocyst (Boroviak et al., 2014; Nichols and Smith, 2009). Reprogramming of murine cells towards a naïve state was also reported in WO2009/101407.

EpiSC are related to primitive streak-stage late epiblast populations and, like human PSC, are heterogeneous both between and within cell lines (Kojima et al., 2014; Tsakiridis et al., 2014). Unlike ground state cells, EpiSC and human PSC passage poorly when dissociated, resulting in low cloning efficiency (Thomson et al., 1998), and are reliant on growth factors, notably fibroblast growth factor (FGF) and TGFβ/activin (Amit et al., 2000; Guo et al., 2009; Vallier et al., 2005). Conversely, they are unresponsive to LI F.

Conversion of mouse EpiSCs to ESC may provide a paradigm for generation of human ground state PSC (Guo et al., 2009). Early trials (Hanna et al., 2010; Wang et al., 2011) noted ESC-like morphology but cells appeared unstable in the absence of continuous transgene expression or selection. More recently complex culture formulations have been proposed to allow propagation of human PSC with altered characteristics (Chan et al., 2013; Gafni et al., 2013; Ware et al., 2014), but these cells remain dependent on FGF, TGFβ and/or serum replacement factors, and lack evidence for rewiring of transcriptional control circuitry.

In summary, despite much interest in this area, the generation of stable 'ground state' or 'naïve' human PSCs has not previously been demonstrated. Thus it can be seen that provision of stable reprogrammed cells that can be reproducibly made would provide a contribution to the art.

We therefore investigated further the generation and stabilisation of human cells with phenotypic features and transcription factor governance characteristic of ground state pluripotency.

DISCLOSURE OF THE INVENTION

The present invention aims to address one or more of the inefficiencies or other problems referred to in the cited art above, and an object of the invention is to provide cells in a naïve state.

It is also an object of the invention to provide methods for resetting human cells to a naïve state.

It is also an object of the invention to provide methods of sustaining human stem cells in a naïve state.

The invention also concerns the provision of media adapted for these things.

In various aspects of the invention described below, the present inventors have shown that human PSCs can be reprogrammed toward the ground state, for example using reprogramming factors and inhibitors.

Previous proposals to allow propagation of human PSC with altered characteristics (Chan et al., 2013; Gafni et al., 2013; Ware et al., 2014) result in cells that remain dependent on FGF, TGFβ and/or serum replacement factors. Additionally, the present inventors have shown by transcriptome analysis that cells obtained by these earlier methods do not achieve the transcriptional state of ground cells. Current human pluripotent stem cells lack the transcription factor circuitry/network that governs the ground state of mouse embryonic stem cells (ESC).

By contrast cells defined herein, and obtainable or obtained by the methods of the present invention are both globally distinct from standard human pluripotent stem cells, for example based on transcriptome data, and highly consistent across cell lines.

Accordingly, in one aspect, the present invention provides human stem cells in a naïve state.

The recent study by Theunissen et al. suggests that a complex cocktail of 5 or 6 inhibitors plus feeders are needed in combination with activin (and sometimes FGF) to reprogram human cells. Furthermore, this study reports that the X chromosome is actually inactivated in their XX "naïve" cells.

The present inventors have demonstrated that appropriate culture mediums and conditions as described herein can be employed to reset/reprogram these human stem cells towards the ground state. The present inventors have also identified culture conditions for sustaining cells in a reset state.

Accordingly, described herein is a method for reprogramming human stem cells (e.g. hPSCs) towards the ground state. The method is a method of resetting transcription factor control circuitry towards ground state. As explained below, the methods may also be applied to stem cells from other species.

The resetting/reprogramming methods described herein are demonstrated to reproducibly reset multiple cells lines. Additionally, the inventors have shown that the methods described herein produce stable cells lines having ground state characteristics. Characteristics of the cells produced are described in more details elsewhere herein.

Thus in one aspect, the invention provides methods for resetting cells toward a 'ground' or 'naïve' state. The methods of resetting cells may also be referred to as methods of reprogramming cells. This reprogramming resets transcription factor control circuitry towards ground state pluripotency.

Induction of a naïve state can be done in a first, resetting medium. This naïve state can be sustained, and the cells propagated in a second, naïve culture medium, that comprises a PKC inhibitor.

The present invention provides a method of reprogramming a human stem cell to a more naïve state comprising:
  a) providing a human stem cell to be reprogrammed,
  b) inducing a more naïve state, wherein the inducing comprises culturing the in a first medium, wherein the first medium comprises a MEK inhibitor and preferably a STAT3 activator, and optionally other factors
  c) sustaining the cell in a second medium, wherein the second medium comprises the presence of a MEK inhibitor and a PKC inhibitor, and preferably a GSK3 inhibitor and a STAT3 activator, and optionally other factors
  d) thereby obtaining a reprogrammed cell.

Thus the present invention provides a method of resetting a human stem cell to a more naïve state, the method comprising: providing a human stem cell to be reset; resetting the transcription factor network, wherein the resetting comprises culturing the cell under a first condition, wherein the first condition is in the presence of a MEK inhibitor and a PKC inhibitor, and sustaining the cell in a second condition, wherein the second condition comprises the presence of a MEK inhibitor and preferably a STAT3 activator, and preferably also a GSK3 inhibitor and a STAT3 activator. Cells The present inventors have used objective criteria and functional assays to demonstrate actual and substantial progress towards reprogramming the human stem cells to a ground/naïve state. The present inventors have demonstrated that ground state pluripotency is a distinctive cell identity for human cells.

The terminology 'naïve' and 'primed' was introduced to describe early and late phases of epiblast ontogeny and respective ESC and EpiSC derivatives (Nichols and Smith, 2009). Human PSC are generally considered more related to primed EpiSCs than to naïve ESC (Chia et al., 2010; De Los Angeles et al., 2012). There is no demonstrable difference in differentiation potential of mouse naïve ES cells and primed EpiSCs, either in vitro or in teratomas. However, EpiSCs, like hESCs/iPSCs, exhibit variable biases towards particular lineages, but nonetheless they are pluripotent.

The transcriptional regulators OCT4 and SOX2 constitute the central pillar of pluripotency through all its phases (Nichols and Smith, 2012; Niwa, 2007; Young, 2011). These factors are essential but not restricted to, nor sufficient for, the ESC ground state.

A select group of regulators present in the pre-implantation epiblast and ESC interconnect with OCT4/SOX2 to confer and sustain naïve status. Foremost among these are NANOG, KLF2, KLF4, ESRRB, TBX3 and TFCP2L1 (Dunn et al., 2014; Ivanova et al., 2006; Martello et al., 2013; Niwa et al., 2009; Ye et al., 2013). Apart from NANOG, these factors are expressed at very low levels or are absent from EpiSC and human PSC.

Strikingly, however, transfection of EpiSC with a single component in conjunction with transfer to 2iL can ignite the entire circuitry and reset the mouse ESC ground state (Guo et al., 2009; Hanna et al., 2009; Silva et al., 2009). Cell state conversion is evidenced by morphology, growth factor independence, clonal expansion, marker profile, epigenome resetting, and contribution to blastocyst injection chimaeras.

Resetting the cells according to the present invention induces expression of these factors in human cells with the exception of ESRRB. The ground state pluripotent identity is less robust in the absence of ESRRB and knockdown of single components, TFCP2L1 or KLF4, causes collapse. Introduction of ESRRB stabilises the human ground state as in mouse ESC and increases resistance to depletion of other factors.

Accordingly, in some embodiments of the methods, ESRRB is introduced into the cell, for example using an expression vector.

A 'ground state' and a 'naïve state' are used interchangeably herein. Cells of the invention are cells in a naïve state. In the methods of the present invention cells are reprogrammed to a naïve state. Cells reprogrammed using methods of the present invention may be referred to as 'reprogrammed' or 'reset' cells.

Ground state cells are a stable self-renewing culture of homogeneous pluripotent stem cells that are epigenetically erased and have the developmental identity and functional capacity of pre-implantation epiblast.

The present invention provides human stem cells in a naïve state.

The present invention provides methods for reprogramming human stem cells, e.g. hPSCs to a naïve state.

The Examples below demonstrate that the cells produced by the methods of the present invention (reset cells) have many similarities to ground state/naïve mouse embryonic stem cells (mESCs) and the human epiblast ICM. Transcriptome analysis shows that reset cells generated are both globally distinct from standard human pluripotent stem cells and highly consistent across cell lines.

The reset cells have dramatically altered growth factor responsiveness, switched metabolic activity and a functionally distinct gene regulatory network.

Reset or reprogrammed cells according to the present invention express genes and proteins that are indicative of a naïve state. The reset cells may express regulators that maintain a naïve status in embryonic stem cells.

Reset cells/cells in a naïve state according to the invention may have 1, 2, 3, 4, 5, 6, 7, 8, 9, 10, 11, 12, 13, 14, 15, 16, 17, 18, 19, 20, 21, 22, 23, 24, 25, 26, 27 or all 28 of the following features. In some embodiments reset cells/cells in a naïve state have 2, 3, 4, 5, 6, 7, 8, 9, 10, 11, 12, 13, 14, 15, 16, 17, 18, 19, 20, 21, 22, 23, 24 or all 25 of features 1 to 24 and 28.

In preferred embodiments the features of cells in a naïve state comprise one or more of features 4 and 8. In some embodiments the cells comprise features 4, 5, 8 and 9. In some embodiments the cells comprise features 4, 5 and 9. In some embodiments the cells have features 5, 8 and 9. In some embodiments the cells have features 4, 5 and 6. In some embodiments the cells have features 4, 8 and 9. In some embodiments the cells have features 4, 6, 8 and 9. In some embodiments the cells have features 1-10. In some embodiments the cells have features 4-10. In some embodiments the cells have features 4-10 and 13-22.

In some embodiments the cells have all of features 13-22. In some embodiments the cells have features 4, 8 and 13-22. In some embodiments the cells have features 1 and 13-22.

In some preferred embodiments the cells have at least 5 of the below features, preferably including feature 4. In some preferred embodiments the cells have at least 5 of the below features including: 4, 8 and 9; 5, 8 and 9 or 4 and 8. In some embodiments the cells have at least 5 of the below features including features 6, 9 and 10.

In some embodiments the cells have at least 10 of the below features. In some embodiments the cells have at least 15 of the below features. In preferred embodiments the cells have all of the below features.

In some embodiments cells in a naïve state have at least feature 28. In some embodiments, cells in a naïve state have at least feature 4. In some embodiments, cells in a naïve state have at least feature 8. In some embodiments, cells in a naïve state have at least feature 7.

In the below list of features, comparative features such as enhancement, up-regulation, down-regulation and increased and decrease levels are in comparison to conventional hPSCs or EpiSCs, for example hPSCs or EpiSCs of the same origin. Where cells are obtained by resetting methods described herein, the comparison may be between cells prior to resetting and after resetting.

Feature 1

In some embodiments cells in a naïve state can continuously and clonally self-renew in culture and retain pluripotency. For example the naïve cells can propagate in naïve culture medium as described elsewhere herein.

Feature 2

In some embodiments the global (i.e. whole genome) transcriptome of a human cell in a naïve state is related to mouse embryonic stem cells and distinct from mouse post-implantation epiblast stem cells (EpiSCs) or conventional human pluripotent stem cells.

The relationship between transcriptomes may be assessed for example using principal component analysis. The relationship may be assessed using gene expression clustering, such as hierarchical clustering, for example using RNA-Seq, or microarray data.

In other words, in some embodiments the whole genome transcriptome of a human cell in a naive state is more similar to that of mouse embryonic stem cells than to mouse post-implantation epiblast stem cells (EpiSCs) or conventional human pluripotent stem cells.

Feature 3

In some embodiments the global transcriptome of a human cell in a naive state is related to pre-implantation epiblast and distinct from post-implantation epiblast.

In other words, in some embodiments the global transcriptome of a human cell in a naive state is more similar to pre-implantation epiblast than post-implantation epiblast.

As for feature 2, the relationship between transcriptomes may be assessed for example using principal component analysis. The relationship may be assessed using gene expression clustering, such as hierarchical clustering, for example using RNA-Seq, or microarray data.

Feature 4

In one embodiment, naïve cells according to the invention express mRNA and protein of pre-implantation epiblast specific transcription factors. For example, naïve cells may express 1, 2, 3, 4, 5, 6 or all of: KLF2, KLF4, TFCP2L1, TBX3, REX1, GBX2 and STELLA (DPPA3). In preferred embodiments at least 80%, 85%, 90% or 95%, preferably at least 90% of cells in a naïve cell culture express 1, 2, 3, 4, 5, 6 or all of the above transcription factors.

In preferred embodiments naïve cells additionally express mRNA and protein of general pluripotency factors, such as OCT4, SOX2 and SALL4. In preferred embodiments naïve cells express elevated mRNA and protein levels of NANOG as compared to conventional hPSCs, for example elevation is by between 30-100%, as measured by qRT-PCR or RNA-seq for mRNA, immunostaining or immunoblotting for protein. For example, mRNA and/or protein levels may be elevated by at least 30, 35, 40, 50, 60, 70, 80, 90 or 100%.

In preferred embodiments at least 80%, 85%, 90% or 95%, preferably at least 90% of cells in a naïve cell culture express and/or upregulate these factors.

Optionally ESRRB is expressed in a non-human cell in a naive state.

Upregulation of factors in reset cells can be measured relative to the cells prior to reprogramming towards a naïve state using the methods described herein, or in comparison to convention hPSCs.

Protein expression can be measured using immunostaining or immunoblotting. mRNA levels can be measured using qRT-PCR or RNA-seq.

Feature 5

In some embodiments human cells in a naïve state are reliant on critical transcription factors defined in mouse embryonic stem cells, particularly TFCP2L1 and KLF4. Accordingly perturbation (for example by mutation, knockdown or knockout) of TFCP2L1 and KLF4 may lead to differentiation or death.

For example, when TFCP2L1 and KLF4 are perturbed while the cells are cultured with a GSK3 inhibitor, a MEK inhibitor, a PCK inhibitor and Lif, the cells die. If the cells are transferred to FGF/KSR they revert to conventional hPSC characteristics.

In some embodiments, the human cells in a naïve state are reliant on one or more of TFCP2L1, KLF4, KLF2, NANOG and TBX3. Accordingly, perturbation of one or more of these factors may lead to cell differentiation or death.

Perturbation of these factors (e.g. TFCP2L1 and KLF4) has little or no effect on conventional human pluripotent stem cells.

Feature 6

In some embodiments the human cells in a naïve state display nuclear localisation of TFE3. In preferred embodiments, at least 45%, 50%, 55%, 60%, 70% or more of the cells in a naïve state display nuclear localisation of TFE3. In preferred embodiments, more than 50% of calls in a naïve state display nuclear localisation of TFE3. Nuclear localisation of TFE3 can be demonstrated by immunostaining, for example.

Feature 7

In some embodiments, the human cells in a naïve state do not express or express at low levels early lineage markers that are typically expressed in convention human pluripotent stem cells. For example the human cells in a naïve state do not express, or only express at low levels markers such as AFP, EOMES and/or BRACHURY. In preferred embodiments, mRNA of the lineage markers is expressed at levels of less than 15, 12, 10, 9, 8, 5, 2, or 1, preferably less than 10 FPKM (Fragments Per Kilobase of transcript per Million mapped reads).

Feature 8

In some embodiments human naïve cells have active mitochondrial respiration. Conventional PSCs do not have this property, while mouse ESC utilise both mitochondrial oxidative phosphorylation and glycolysis.

Mitochondrial respiration may be measured by oxygen consumption rate (OCR).

Basal OCR, as measured by extracellular flux analysis, may be at least 2-fold higher in cells in a naïve state than in conventional human pluripotent stem cells. Maximal OCR in the presence of an uncoupling reagent such as FCCP may be at least 4-fold higher.

Cells in a naïve state have substantial spare respiratory capacity, for example they may have a 4-10 fold increase in OCR in the presence of FCCP. Conventional human pluripotent stem cells show only a marginal increase in OCR in the presence of FCCP.

Accordingly, in some embodiments cells in a naïve state may utilise both mitochondrial oxidative phosphorylation and glycolysis. The cells in a naïve state may self-renewal in the presence of 2-deoxyglucose or low glucose. Conventional hPSCs do not renew in these conditions.

Feature 9

In some embodiments the cells in a naïve state have genome-wide hypomethylation. Preferably, the genome-wide methylation level is 70%, 60%, 50%, 40%, 30% or less that the methylation level of hPSCs, preferably 50% or less.

Hypomethylation is a distinctive property of primitive cells in human embryos that is lost in conventional PSC (Guo et al., 2014) but is recapitulated in reset cells of the invention. Global demethylation has to be considered essential for resetting to a primitive naïve state, which is by definition epigenetically erased.

Reset cells according to the present invention may show global demethylation in response to reprogramming using the methods of the invention. For example immunofluorescence staining for 5-methylcytosine (5mC) is weaker in reset cells than in cells that have not been reprogrammed.

Reset cells may show a reduction of at least 10-90%, for example 15-80, 20-70, 30-60, 40-50, preferably about at least 50% in methylation of CpG genome-wide. In some embodiments methylation is reduced to 60% or less, preferably to 30-40%. Methylation levels may be measured in comparison to methylation levels of conventional hPSCs.

Methylation levels may be quantified by nucleoside mass spectrometry or by bisulphite modification coupled to deep sequencing (B seq).

Feature 10

Cells in a naïve state according to the invention may have lower levels of histone modifications associated with gene silencing than hPSCs or EpiSCs. For example reduced levels of H3K27me3 and H3K9me3.

Levels of histone modifications may be measured by quantitative immunostaining or chromatin immunoprecipitation couple to deep sequencing (ChIP-seq).

Female cells in a naïve state may show reversible epigenetic erasure of the X chromosome, more specifically demethylation of the X chromosome, and absence of H3K27me3 foci in XX reset cells, preferably in 80% or more of XX cells. In some embodiments reversal of a naïve state, e.g. by culture in KSR/FGF, restores H3K27me3 foci in the majority of cells, preferably by at least 50%, 60%, or 70% or more.

Feature 11

In some embodiments cells in a naïve state are capable of incorporation into a host embryo inner cell mass (ICM) and a pre-implantation epiblast to form embryo chimaeras. The incorporated cells may be visualised by the presence of viable cells within the ICM at the expanded blastocyst stage.

Feature 12

In some embodiments cells in a naïve state can colonise a post-implantation epiblast and derivative tissues in chimaeras formed with the same, or closely related, species.

Feature 13

In some embodiments cells in a naïve state can self-renew in the absence of detectable Erk/MAP kinase signalling. The signalling may be detected using immunoblotting for phosphorylated Erk1 and Erk2. In the absence of Erk/MAP kinase signalling, there phosphorylated Erk1 and Erk2 are no detectable. In other words, cells in a naïve state may self-renew in the presence of complete inhibition of Erk/MAP kinase signalling.

Feature 14

In some embodiments cells in a naïve state can self-renew in the presence of growth factor receptor tyrosine kinase signalling inhibition.

Feature 15

In some embodiments cells in a naïve state can self-renew in the presence of TGF-β/activin signalling inhibition. In other word cells in a naïve state may propagate independently from activin/TGFβ. For example reset cells may propagate in the presence of the inhibitor A83-01.

Feature 16

In some embodiments cells in a naïve state can self-renew in the presence of PKC inhibition or knockdown, in particular atypical PKC (aPKC) inhibition, particularly aPKC iota inhibition.

Feature 17

In some embodiments cells in a naïve state can self-renew in the presence of partial inhibition of (GSK3) glycogen synthase kinase-3 activity. For example the cells in a naïve state can self-renew in the presence of a GSK3 inhibitor, for example when the concentration of the inhibitor is about 0.1-5 μM, preferably about 0.5-2 μM, preferably about 1 μM.

Feature 18

In some embodiments cells in a naïve state can self-renew in the presence of leukaemia inhibitory factor (LIF) or other STAT3 agonists/activators.

Feature 19

In some embodiments cells in a naïve state can self-renew from dissociated single cells without Rho associated kinase inhibition (ROCKi). In other words, cells in a naïve state can self-renew in culture that does not comprise a ROCK inhibitor.

Feature 20

In some embodiments cells in a naïve state can self-renew in the absence of serum or serum substitutes.

Feature 21

In some embodiments cells in a naïve state can self-renew in the absence of feeder cells Feature 22

In some embodiments cells in a naïve state can self-renew in the absence of transgene expression or other genetic perturbation. For example, the cells in a naïve state can self-renew in the absence of exogenous reprogramming factor expression.

Feature 23

The Examples illustrate that reset cells produce by the methods of the invention are stable. Preferably, they show retention of normal karyotype (i.e. diploid) in long term passaging.

In some embodiments, cells in a naïve state retain diploid karyotype, preferably without rearrangement, insertion or deletion over more than 5, 10, 15, 20, 25, 30, 35, 40, 50 or more population doublings, preferably, the cells in a naïve state retain diploid karyotype over more than 40 population doublings.

Feature 24

In some embodiments, cells in a naïve state differentiate in the presence of growth factor stimulation of Erk/MAP kinase signalling and activin into conventional primed pluripotent phenotype. Optionally, this change can be measured by loss of pre-implantation epiblast (or 'grounds state') transcription factors and/or by up-regulation of lineage markers at the mRNA and protein level as described herein.

Feature 25

In some embodiments, cells in a naïve state are able to differentiate in vitro into primordial germ cells as well as somatic germ layers Feature 26

In some embodiments, cells in a naïve state can establish continuous culture in vitro by direct transition from a pre-implantation epiblast. In other words, the cells in a naïve state can be obtained for culture directly from a pre-implantation epiblast.

Feature 27

In some embodiments cells in naïve state are identifiable by their morphology. The cells may have a tightly packed domed appearance. The cells may also be described as forming compact refractile colonies. Mouse ESC have a tightly packed domed appearance.

Feature 28

In some embodiments cells in a naïve state have a reduction in expression of de novo methyltransferase (DNMT3a and DNMT3b). In preferred embodiments the reduction is at both mRNA and protein level as compared with conventional human pluripotent stem cells.

In preferred embodiments the reduction is at least than two-fold, optionally three-fold. In other words, the reduction in expression of DNMT3a and DNMT3b may be at least half of that of conventional human pluripotent stem cells.

In summary, the invention provides a human stem cell in a naïve state, wherein the naïve state is characterised by at least 1, 2, 3, 4, 5, 6, 7, 8, 9, 10, 11, 12, 13, 14, 15, 16, 17, 18, 19, 20, 21, 22, 23, 24, 25, 26, 27 or all of the following features ("naïve state features"):

a) the ability to continuously and clonally self-renewal in culture and retain pluripotency
b) a whole genome transcriptome related to mouse embryonic stem cells and distinct from mouse post-implantation epiblast stem cells (EpiSCs) or conventional human pluripotent stem cells as measured by principal component analysis or hierarchical clustering of RNA-seq or microarray data
c) a whole genome transcriptome related to pre-implantation epiblast and distinct from post-implantation epiblast as measured by principal component analysis or hierarchical clustering of RNA-seq or microarray data.
d) expression of mRNA and protein of pre-implantation epiblast specific transcription factors, optionally 1, 2, 3, 4, 5, 6 or all of: KLF2, KLF4, TFCP2L1, TBX3, REX1, GBX2 and STELLA (DPPA3), and expression of mRNA and protein of general pluripotency factors, such as OCT4, SOX2 and SALL4, and optionally elevated mRNA and protein levels of NANOG as measured by qRT-PCR and immunostaining or immunoblotting respectively;
e) reliance on critical transcription factors defined in mouse embryonic stem cells, particularly TFCP2L1 and KLF4 as demonstrated by e.g. cell collapse upon knock down or knock out;
f) nuclear localisation of TFE3 in e.g. more than 50% of cells demonstrated by immunostaining;
g) low level expression (e.g. less than 10 FPKM) or absence of expression of early lineage markers that are typically expressed in conventional human pluripotent stem cells, such as AFP, EOM ES and/or BRACHURY;
h) active mitochondrial respiration, for example as measured by oxygen consumption rate (OCR);
i) genome-wide hypomethylation to below 50% measured by nucleoside mass spectrometry or bisulfite modification coupled to deep sequencing (BS-seq);
j) lower levels of histone modifications associated with gene silencing, such as reduced levels of H3K27me3 and H3K9me3 compared with conventional human pluripotent stem cells or somatic cells as determined by quantitative immunostaining or chromatin immunoprecipitation coupled to deep sequencing (ChIP-seq);
k) capable of incorporation into a host embryo inner cell mass and a pre-implantation epiblast to form embryo chimaeras, e.g. as visualised by presence of viable cells within the ICM at the expanded blastocyst stage;
l) able to colonise a post-implantation epiblast and derivative tissues in foetal and adult chimaeras following introduction into a pre-implantation embryo of the same, or a closely related, species;
m) self-renewal in the absence of detectable Erk/MAP kinase signalling, for example as measured by immunoblotting for phosphorylated Erk1 and Erk2;
n) self-renewal in the presence of growth factor receptor tyrosine kinase signalling inhibition;
o) self-renewal in the presence of TGFbeta/activin signalling inhibition;
p) self-renewal in the presence of PKC inhibition or knockdown;
q) self-renewal in the presence of partial inhibition of (GSK3) glycogen synthase kinase-3 activity;
r) self-renewal in the presence of STAT3 agonists, such as LIF;
s) self-renewal from dissociated single cells without Rho associated kinase inhibition (ROCKi);
t) self-renewal in the absence of serum or serum substitutes;
u) self-renewal in the absence of feeder cells;
v) self-renewal in the absence of transgene expression or other genetic perturbation;

w) retention of diploid karyotype without rearrangement in long-term passaging, for example over more than 40 population doublings;

x) differentiation into conventional primed pluripotent phenotype in the presence of growth factor stimulation of Erk/MAP kinase signalling and activin, for example as measured by down-regulation of ground state transcription factors and up-regulation of lineage markers at mRNA and protein level;

y) able to differentiate in vitro into primordial germ cells as well as somatic germ layers;

z) established in continuous culture in vitro by direct transition from a pre-implantation epiblast;

aa) culture has tightly packed domed appearance;

bb) greater than two-fold reduction in expression of de novo methyltransferase (DNMT3a and DNMT3b) at both mRNA and protein level compared with conventional human pluripotent stem cells.

Further optional features of cells in a naïve state, including cells in a naïve state obtained by the methods described herein are described below. Cells in a naïve state may have one or more of the below features in addition to those described above.

In one embodiment, expression of one or more of the following factors is upregulated in the reset cells as compared to the cells before reprogramming:

NANOG
KLF2
KLF4
ESRRB
TBX3
TFCP2L1
KLF5
DPPA3 (STELLA)
ZFP42 (REX1)
GBX2
SALL4
DNMT3L

Expression of these factors is indicative of a naïve state. Accordingly, cells in a naïve state express one or more of the above factors, in addition to OCT4, SOX2 and NANOG.

In preferred embodiments expression of 2, 3, 4, 5, 6, 7, 8, 9, 10, 11, 12, 13 or all of the above factors is upregulated in reset cells. In some embodiments, 1, 2, 3, 4, 5, 6 or all of: OCT4, SOX2, NANOG, KLF2, KLF4, TBX3 and TFCP2L1 are upregulated in reset cells.

In some embodiments, expression of NANOG, KLF2, KLF4, TBX3 and TFCP2L1 is induced in reset cells.

In particularly preferred embodiments reset cells according to the invention express upregulated levels of endogenous KLF4 and NANOG. In particularly preferred embodiments reset cells according to the invention express upregulated levels of endogenous TFCP2L1 and KLF4. In other preferred embodiments the reset cells express upregulated levels of NANOG, TFCP2L1 and KLF4.

In some embodiments TET1 is also upregulated.

Reset cells/cells in a naïve state of the present invention may also display downregulation of lineage specific genes as compared to untreated cells. For example, expression of one or more of the following factors is downregulated in the reset cells as compared to the hPSCs before reprogramming. For example, or more of the following lineage specific genes may be down-regulated:

ACTC1
CER1
FLT1
NES
NOG
EOMES FOXA2
CTNNB1
BMP2
BRACHYURY

Cells in a naïve state express one or more the factors listed above that are indicative of a naïve state. Cells in a naïve state may also have downregulated expression of lineage specific genes, for example down regulation of one or more of the lineage specific genes listed above.

Cells reset using the methods described herein may self-renew continuously without ERK signalling, are phenotypically stable.

Reset cells may differentiate in vitro and form embryoid bodies. Reset cells may be capable of differentiating into cells of all three germ layers.

Reset cells may form teratomas in vivo, for example when integrated into mice.

Changes in properties may be observed in comparison to human pluripotent stem cells that have not been reprogrammed.

Cells in a naïve state may express one or more (e.g. 2, 3, 4, 5, 6, or 7) surface markers selected from the list consisting of: HAVCR1 (CD365), CCR8 (CDw198), ITGAM (CD11B), IL6R (CD126), PVR (CD155), ADGRE5 (CD97) and CD53.

In one aspect the present invention provides cells obtained by the methods described herein.

Cells in a naïve state may have one or more of the properties described above for reset cells. For example, cells may have 2, 3, 4, 5, 6, 7, 8, 9, 10, 12 or more of the properties described for reset cells. In other words they may have one or more of the following properties:

Up-regulation of one or more of the regulators that maintain naïve status in embryonic stem cells Up-regulation of one or more the factors listed as upregulated in reset cells above Down-regulation of lineage specific factors a tightly packed domed appearance compact refractile colonies ability to differentiate in vitro capable of germ layer specification utilisation of both mitochondrial oxidative phosphorylation and glycolysis global hypomethylation demethylation of the X chromosome with reduction in intermediate levels of CGI demethylation lower levels of trimethylation of histone 3 lysine 9 (H3K9me3)

ability to form teratomas in vivo

In another aspect the present invention provides reset cells having one or more of the properties of reset cells/cells in a naïve state described herein. In particular, reset cells may express regulators that maintain a naïve state in embryonic stem cells.

Induction of a Naïve State

Cells of the invention, in a naive state, may be obtained using the methods described herein.

Induction of a naïve state may also be referred to herein as resetting to a naïve state.

Inducing a more naïve state may comprise expressing reprogramming factors in the cell. Reference to reprogramming factors is reference to factors which when expressed in the cell result in it being reprogrammed. Generally, the reprogramming factors include one or more transcription factors.

In some embodiments induction of a naïve state comprises expression of 1, 2, 3, 4 or all of KLF4, NR5a1 KLF17, NANOG and KLF2.

The present inventors have found that short-term expression of two components, NANOG and KLF2, is sufficient to ignite other elements of the network and reset the human pluripotent state.

In the present invention, the reprogramming factors may comprise, consist essentially of, or consist of Krüppel-like Factor 2 (KLF2) and NANOG. Preferably the reprogramming factors are human factors.

In these embodiments the first medium may further comprise a glycogen synthase kinase 3 (GSK3) inhibitor.

The first medium may further comprise a fibroblast growth factor (FGF) receptor inhibitor, for example PD173074.

The first medium may also comprise a PKC inhibitor.

Preferably the STAT3 (signal transducer and activator of transcription 3) activator is LIF, most preferably human LIF (hLIF). The first medium may contain an alternative agonist of the LIF receptor or other receptors that lead to activation of STAT3, such as IL-6 and soluble IL-6 receptor or oncostatin M.

The present invention provides a method of reprogramming a human stem cell to a more naïve state comprising:
a) providing a human stem cell to be reprogrammed,
b) inducing a more naïve state, wherein the inducing comprises: expressing or introducing reprogramming factors, wherein the reprogramming factors comprise NANOG and KLF2; and culturing the in a first medium, wherein the first medium comprises a MEK inhibitor and preferably a STAT3 activator,
c) sustaining the cell in a second medium, wherein the second medium comprises a PKC inhibitor, a MEK inhibitor and optionally a STAT3 activator and a GSK3 inhibitor,
d) thereby obtaining a reprogrammed cell.

The reprogramming factors may be expressed in the cell prior to culturing of the cell in the first medium.

Before transfer to the first medium, cells may be cultured in a conventional PSC medium, such as a serum-free medium, preferably in serum-free medium with fibroblast growth factor (FGF). For example FGF/KSR medium may be used. FGF/KSR is a conventional PSC medium that contains knockout serum replacement (KSR) and FGF. In more detail, FGF/KSR comprises: MEM/F12 with 10 ng/ml bFGF and 20% KSR supplemented with 100 mM 2-mercaptoethanol, MEM nonessential amino acids, 2 mM L-glutamine. The serum free medium may be supplemented by a Rho-associated protein kinase inhibitor (ROCKi).

Reprogramming factors (e.g. NANOG and KLF2) may be expressed when the cell is in serum-free medium (e.g. FGF/KSR). The cells can be transferred to the first medium, for example up to 6 days after reprogramming factor expression has started, for example up to 5 days, up to 4 days, up to 3 days after reprogramming factor expression has started. Preferably, the cells are transferred to the first medium between half a day and 2 and a half days after reprogramming factor expression has started, more preferably 1-2 days, e.g. 1 or 2 days after reprogramming factor expression has started.

In one embodiment, inducing the cells to a more naïve state comprises expressing reprogramming factors in the cell, wherein the reprogramming factors comprise NANOG and KLF2, and culturing the in cell a resetting medium, wherein the resetting medium comprises a MEK inhibitor, a GSK3 inhibitor and a STAT3 activator.

In another embodiment, inducing the cells to a more naïve state comprises expressing reprogramming factors in the cell, wherein the reprogramming factors comprise NANOG and KLF2, and culturing the in cell a resetting medium, wherein the resetting medium comprises a MEK inhibitor, a FGF receptor inhibitor and a STAT3 activator.

Methods of expressing reprogramming factors in the cells are discussed in more detail elsewhere herein.

The present inventors have shown that it is possible to reset the cells towards the ground state without exogenous expression of NANOG and KLF2 or other reprogramming factors. In the absence of exogenous reprogramming factors, it is preferable that the first medium further comprises a histone deacetylase inhibitor (HDACi), for example valproic acid or sodium butyrate. Preferably the HDACi is at a concentration of 0.1-1 mM, preferably 0.5-1 mM.

In the absence of reprogramming factors it is preferable that the culture medium is E6-based medium.

Accordingly, in some embodiments, the present invention provides a method of reprogramming a human stem cell to a more naïve state comprising:
a) providing a human stem cell to be reprogrammed,
b) inducing a more naïve state, wherein the inducing comprises culturing the in a first medium, wherein the first medium comprises a MEK inhibitor, a HDAC inhibitor and preferably a STAT3 activator,
c) sustaining the cell in a second medium, wherein the second medium comprises and a PKC inhibitor, a MEK inhibitor and optionally a GSK3 inhibitor and a STAT3 activator,
d) thereby obtaining a reprogrammed cell.

In a preferred embodiment, the first medium further comprises a tankyrase inhibitor, for example a tankyrase-1 inhibitor. In some embodiments the tankyrase inhibitor is XAV939. The first medium may also comprise a PKC inhibitor.

In some embodiments the second medium further comprises a ROCK inhibitor, for example Y27632.

In some embodiments the first medium further comprises an HDAC inhibitor, for example valproic acid sodium salt or sodium butyrate. In preferred embodiments the first medium comprises valproic acid sodium salt.

In some embodiments the HDAC inhibitor is present at a concentration of about 0.05-10 mM, for example 0.1-5 mM, 0.2-2 mM, preferably about 0.5-1 mM.

In preferred embodiments the first medium does not contain FGF. In some embodiments the first medium does not contain activin. In some embodiments the first medium does not contain FGF or activin.

In one embodiment, inducing a more naïve state comprises culturing the in cell a resetting medium, wherein the resetting medium comprises one or more of:
a MEK inhibitor, a tankyrase inhibitor, a HDAC inhibitor a PKC inhibitor and a STAT3 activator.

In one embodiment, inducing a more naïve state comprises culturing the in cell a resetting medium, wherein the resetting medium comprises a MEK inhibitor, a tankyrase inhibitor, a HDAC inhibitor and a STAT3 activator. Preferably, in this embodiment, exogenous reprogramming factors are not expressed in the inducing step.

'Resetting' Medium.

The 'first medium' may also be referred to herein as the 'resetting' or 'inducing' medium. Culturing the cells in the first medium may also be referred to as culturing the cells in a first condition. These terms and phrases are all used interchangeably.

The first medium per se forms one aspect of the invention, as does its use in the resetting methods described herein.

The first medium may comprise a basal medium (such as N2B27 or mTeSR™-E6) that is supplemented, for example with one, two, three or more of: a MEK inhibitor, a GSK3 inhibitor, a STAT3 activator, an FGF inhibitor, a HDAC inhibitor, a tankyrase inhibitor, a ROCK inhibitor and a PKC inhibitor. Preferably, the first medium comprises a basal medium (such as N2B27 or mTeSR™-E6) that is supplemented, for example with one, two, three or more of: a MEK inhibitor, a STAT3 activator, an FGF inhibitor, a HDAC inhibitor, a tankyrase inhibitor, a ROCK inhibitor and a PKC inhibitor.

In some embodiments, the first medium consists, or consists essentially, of a basal medium supplemented with a MEK inhibitor, a tankyrase inhibitor, a STAT3 activator, ROCK inhibitor, and preferably also a HDAC inhibitor.

In some embodiments, the first medium consists, or consists essentially, of a basal medium supplemented with a MEK inhibitor, an FGF inhibitor, a STAT3 activator and ROCK inhibitor.

In some embodiments, the first medium consists, or consists essentially, of a basal medium supplemented with a MEK inhibitor, a STAT3 activator and ROCK inhibitor.

The first medium is preferably a serum-free medium, such as mTeSR™-E6 basal medium (available from StemCell Technologies). Other media that are suitable for the propagation of stem cells may be used. For example N2B27 medium may be used. Alternatively, DMEM/F12 may be used.

The basal medium comprises insulin amongst other things.

In some embodiments, the basal medium comprises 1, 2, 3, 4, 5, 6, or preferably all of: DMEM/F12 (liquid), Neurobasal, (liquid), N2 supplement, B27 supplement, β-mercaptoethanol, L-Glutamine, Insulin, and preferably also L-Ascorbic Acid.

In some embodiments, the basal medium consists, or consists essentially, of DMEM/F12 (liquid), Neurobasal, (liquid), N2 supplement, B27 supplement, β-mercaptoethanol, L-Glutamine, Insulin, and preferably also L-Ascorbic Acid.

In preferred embodiments the basal medium is supplemented with L-Ascorbic Acid.

In some embodiments the first medium lacks serum or growth factors.

Further details, including examples of factors and preferred factors and culture conditions are given elsewhere herein.

Sustaining a Naïve State

The inventors have also shown that inhibition of ERK and protein kinase C signalling sustains the reset (naïve) state independently of exogenous NANOG and KLF2.

Accordingly, in one aspect, the invention provides a method of sustaining/maintaining/propagating human stem cells in a naïve state, the method comprising inhibiting PKC and MAPK/ERK. Preferably, the method further comprises treatment with a STAT3 activator. In a preferred method, the STAT3 activator is LIF, most preferably human LIF.

The invention also provides the use of a PKC inhibitor in combination with and MAPK/ERK/MEK inhibitor for sustaining/maintaining human cells in a naïve state.

The concentrations and other agents as described for sustaining a naïve state are applicable to these methods and uses.

Naïve Cell Culture Medium

The 'second medium' may be referred to as the 'naïve culture' or 'sustaining' medium. Culturing the cells in the second medium may also be referred to as culturing the cells in a second condition. These terms and phrases are all used interchangeably.

The second medium per se forms one aspect of the invention, as does its use in the culturing methods described herein.

The second medium comprises a MEK inhibitor and a PKC inhibitor. In preferred embodiments the second medium further comprises a GSK3 inhibitor. In preferred embodiments the second medium further comprises a STAT3 activator. In preferred embodiments the second medium comprises both a GSK3 inhibitor and a STAT3 activator.

In preferred embodiments the second medium comprises a Rock inhibitor, for example Y-27362.

Accordingly, in some embodiments, the second medium comprises a basal medium, a MEK inhibitor, a PKC inhibitor and preferably a GSK3 inhibitor and a STAT3 activator. In some embodiments, the second medium consists, or consists essentially, of a basal medium, a MEK inhibitor, a PKC inhibitor and preferably a GSK3 inhibitor and a STAT3 activator, and optionally a ROCK inhibitor.

The present inventors have shown that while colony morphology is improved in the absence of a GSK3 inhibitor, growth rate was reduced. Accordingly, in a preferred embodiment the quantity of GSK3 inhibitor (e.g. CHIR99021) in the second medium is titrated prior to the reprogramming. Accordingly the concentration of GSK3 inhibitor in the second medium is a concentration that is low enough to allow maintenance of ground state morphology, while high enough to restore the growth rate.

The GSK3 inhibitor may be similarly titrated for the first medium.

In one embodiment the GSK3 inhibitor is used at a concentration of 0-3 µM, preferably, 0.5-2 µM, more preferably about 1 µM.

In a preferred embodiment the PKC inhibitor is an inhibitor of an atypical PKC (aPKC), for example PKC iota. In a further embodiment the PKC inhibitor may inhibit both aPCK and also PKC delta"

Preferably the STAT3 (signal transducer and activator of transcription 3) activator is LIF, most preferably human LIF (hLIF). The first medium may contain an alternative agonist of the LIF receptor or other receptors that lead to activation of STAT3, such as IL-6 and soluble IL-6 receptor or oncostatin M.

In some embodiments the second medium further comprises a ROCK inhibitor, for example Y27632.

In some embodiments activin may be included in the second medium at a concentration between 0.5-5.0 ng/ml.

The basal medium is preferably a serum-free medium, such as N2B27 medium. Other media that are suitable for the propagation of stem cells may be used.

In some embodiments, the basal medium comprises 1, 2, 3, 4, 5, 6, or preferably all of: DMEM/F12 (liquid), Neurobasal, (liquid), N2 supplement, B27 supplement, β-mercaptoethanol, L-Glutamine, Insulin, and preferably also L-Ascorbic Acid.

In some embodiments, the basal medium consists, or consists essentially, of: DMEM/F12 (liquid), Neurobasal, (liquid), N2 supplement, B27 supplement, β-mercaptoethanol, L-Glutamine, Insulin, and preferably also L-Ascorbic Acid.

Preferred Cells for Use in the Methods

The cell to be reprogrammed is preferably a human cell. The human cells may be a pluripotent stem cell (hPSC). hPSCs may be induced (iPSCs) or embryo-derived.

Cells may be tissue biopsy samples that are initially reprogrammed by standard methods (Takashi et al., 2007; Yu et al, 2007), preferably via a non-integrating vector system such as Sendai virus, then reset using the methods described herein.

Cells may be obtained from pre-existing cell lines without need for biopsy. For example the invention is applicable to pre-existing embryonic stem cell lines. Human embryo-derived stem cells are obtainable from established cell lines such as the Shef6 embryonic cell lines.

In some embodiments cells are derived directly from embryos. Cells derived directly from embryos may be reset using the methods described herein. In some embodiments cells derived directly from embryos are propagated/sustained using the methods described herein.

In some embodiments cells are derived from pre-implantation stages. The embryos may be developed in vitro or in utero are cultured either intact, or after isolation of the inner cell mass (ICM) by microdissection or immunosurgery. Optionally the cells are dissociated into single cells prior to use in the methods of the present invention.

In some embodiments cells are derived from late blastocysts, peri-implantation embryos or post-implantation epiblast. Epiblast cells may be dissected and/or dissociated prior to use in the methods of the invention.

Human embryonic stem cells for use in the invention may be obtained using methods which do not require destruction of the embryo. For example, embryonic stem cells may be obtained from the human embryo by biopsy. Methods for obtaining embryonic stem cells from the embryo without destruction of the embryo were disclosed for example in Klimanskaya et al. 2006.

In some embodiments of the present invention, the methods and uses do not involve destruction of human embryos. In some embodiments, the methods do not involve or use cells obtained by methods requiring destruction of human embryos.

In some embodiments the methods and uses of the invention do not involve use of a human embryo for industrial/commercial purposes. In some embodiments, the methods do not involve cells obtained by methods requiring use of a human embryo for industrial/commercial purposes.

In some embodiments, the cell is not a human embryonic stem cell.

Human iPSCs may be derived from different cell types. For example, the cells can be produced from Fibroblast's, keratinocytes, adipose cells, bone marrow stromal cells or neuronal cells, particularly neuronal stem cells. Human iPSCs may be derived from diploid cells which may be a 'wild-type' or non-transformed cell. In other embodiments an iPSC is derived from a transformed (tumour) cell.

Cells may be obtained from an individual by standard techniques, for example by biopsy for skin cells. Cells may preferably be obtained from an adult. Methods for generating iPSCs are known in the art, for example as described in: Takahashi et al Nature 2007; Yu et al, Science 2007.

The cell to be reprogrammed may also be a cell which already expresses one of the reprogramming factors.

It will be understood that the methods and uses described herein also apply to other primates and non-human mammalian cells, and the features of the methods, uses and reset cells as described herein apply to non-human mammalian cells mutatis mutandis. Put another way, it will be understood (unless context demands otherwise) that where the term "human" is recited herein, it can be replaced with "mammalian" or any of the following: primate; non-human mammalian non-human primate; pig; sheep; cat; dog; goat; cow; camel; horse; llama; alpaca etc. In one embodiment the non-human mammalian cell is not a rodent cell.

Reprogramming Factors

As explained above, in some aspects of the invention inducing a more naïve state further comprises expressing reprogramming factors in the cell (e.g. KLF2 and NANOG). In preferred embodiments the reprogramming factors are human factors.

In some embodiments, other reprogramming factors may be used. For example, other factors which are known to play a role in programming of pluripotent stem cells may be used. Accordingly, in some embodiments, reprogramming factors for use in the present invention include one or more of OCT3/4, SOX2, Klf4, LIN28, c-MYC, KLF2 and NANOG. In some embodiments, reprogramming factors for use in the present invention include one or more of KLF4, NR5a1 KLF17, NANOG and KLF2. In some embodiments, reprogramming factors for use in the present invention include one or more of KLF4, NR5a1 KLF17, NANOG, OCT3/4, SOX2, LIN28, c-MYC and KLF2.

In some embodiments at least 2, at least 3 or at least 4 of the reprogramming factors are used. In a preferred embodiments at least KLF2 and NANOG are used.

Sequence data for these factors are available in established databases, for example the Ensembl Gene Browser or UniProt databases.

Expression of Reprogramming Factors

Reprogramming factors can be expressed in the cell using any method available to the skilled person.

In some embodiments the cell is not permanently genetically modified. The reprogramming factors may be transiently expressed, e.g. from plasmids.

Reprogramming factors may be expressed for at least 4, 5, 6, 7, 8, 9, or at least 10 days. In preferred embodiments, the reprogramming factors are expressed for at least 8 days.

In these embodiments the first medium may comprises an FGF receptor inhibitor. In some embodiments the first medium comprises an FGF receptor inhibitor, but no GSK3 inhibitor.

Plasmids which constitutively express the reprogramming factors (e.g. NANOG and KLF2) may be used. These methods suitably comprise introducing into the cells a plasmid preparation which expresses one or more reprogramming factors in the cell.

In an alternative embodiment reprogramming factors may be introduced by liposomal delivery or microinjection of either mRNAs or proteins prepared in vitro.

Factors may be expressed by integration into the genome e.g. factors may be introduced via retroviral infection or using a transposable element system. For example the piggyBac transposable element system may be used. Factors may be introduced in the form of mRNAs or proteins.

In these embodiments, the methods may include a step of selection after integration, in order to select the cells where integration is successful.

In these embodiments the method may comprise addition of an agent to induce gene expression. In these embodiments the reprogramming factors are inducibly expressed. Accordingly the reprogramming factors may be under the control of an inducible promoter. In the Examples below, the inventors use doxycycline (DOX) inducible expression of NANOG and KLF2, however, other regulatory systems may be used that use different operators, promoters and inducers.

In the Examples below the inventors have employed the piggyBac transposable element system in integrating methods. Irrespective of this, it will be understood that in embodiments of the invention integrative vector systems may be utilised. In such methods the gene encoding the reprogramming factor may optionally be removed or excised following the method.

It will be appreciated by those skilled in the art that the genetic material can be any form which leads to expression e.g. DNA, RNA and so on.

In some embodiments the methods comprise a step of transfecting the cell with genetic material encoding reprogramming factors. In some embodiments the cell is retransfected every 2-8, 3-7, or 4-6 days during induction of a naïve state.

Generally the cell may be maintained in culture until extrachromosomal genetic material, if any, introduced is lost, thereby providing a reprogrammed cell which is not genetically modified compared to the cell provided for reprogramming.

Accordingly, in some embodiments the cells produced by the methods of the invention are not genetically modified compared to the cell provided for reprogramming.

After introduction of genetic material to express the reprogramming factors, the cell is preferably maintained in culture to allow reprogramming of the cell and growth of the cell.

According to one aspect of the invention, transfection leads to transient expression of the reprogramming factors and, as a result, reprogramming but yielding a population of cells without genetic modification.

Lack of genetic modification in this context will be understood to mean the absence of heterologous nucleic acid sequences (especially those encoding reprogramming factors) stably introduced in the genome of the cell. By "heterologous" is meant that the nucleic acid in question has been introduced into said cell or an ancestor thereof, using genetic engineering. A heterologous nucleic acid may normally be absent from cells of that type (e.g. retroviral sequence) or may be additional to an endogenous gene of the cell (e.g. an additional copy of a reprogramming factor, where the endogenous copy has been inactivated) but in each case the heterologous nucleic acid is introduced by human intervention.

The nature of the transfection may be that extended culture of the reprogrammed cells results in loss of the transfection agent. Confirmation that cells are obtained with no genetic modification can be achieved by screening clones of the cells and analysing the DNA, for example using PCR with single copy deletion using this approach we have confirmed absence of genetic modification in cells obtained by these methods.

Expression of the reprogramming factors is suitably achieved using genetic material introduced into the cells and containing coding sequences for the reprogramming factors operatively linked to promoters; preferably, plasmids are used. The promoters direct expression of the reprogramming factors and, generally, a constitutive promoter is suitable, but the choice of promoter is not critical provided the reprogramming factors are expressed in the cells. Examples of suitable promoters include CAG, PKG and CMVE. The genetic material, such as the plasmids, further preferably does not replicate and has a very low integration efficiently, which can be further reduced e.g. by using circular rather than linear plasmids.

Plasmids are preferably introduced by using nucleofection which is an established procedure and known to be efficient. Other chemical and electrical methods are known and are also efficient, including electroporation and lipofection. Different transfection methods and protocols are available for different cells, all well known in the art. Generally, it is believed that the choice of plasmid and promoter and transfection route is not critical to the invention. The plasmid preparation comprises one or more plasmids which express in the cell the one or more reprogramming factors. There may be one plasmid for each factor or a plasmid may express more than one or all factors.

Culturing Protocols hPSCs may be cultured in conventional PSC medium, such as serum-free medium, for example a serum replacement medium supplemented with FGF, e.g. FGF/KSR. Cells may be passaged every 5 to 7 days prior to resetting. Cells may be passaged as small clumps by dissociation.

Cells may be dissociated prior to culture with the first medium, for example using trypsin. The cells may be plated as single cells. A ROCK inhibitor may be used to support initial plating.

The medium may be changed to the first medium up to 5 days after replating, for example, up to 4 days, 3, days, 2, days or 1 day after replating. In preferred embodiments, the medium is changed 0.5-2 days after replating, preferably about 1 day after replating.

In some embodiments, when the cell is cultured in the first medium, the medium may be replaced at least daily, or twice daily. The first medium may be replaced every 1-5, 1-4, 1-3, or 1-2 days. In preferred embodiments the first medium is replaced daily.

In some embodiments, when the cell is cultured in the first medium, the cells may be dissociated every 3-10, 4-8, or preferably 5-7 days, for example using accutase. The cells may be replated as single cells.

The cells may be cultured in the first medium for at least 5 days, for example 6, 7, 8, 9, 10, 11, 12, 13, 14, 15, 16, 17, 18, 19, 20, 21, 22, 23, 24, 25, 26, 27, 28, 29, 30 days or longer. In some embodiments, the cells are cultured in the first medium for 1-4 weeks, preferably about 2 weeks. Cells are then transferred to the second medium.

Cells may be transferred to the second medium once the cells are reset, for example, when the cells display the properties described for reset cells as described herein. In preferred embodiments the cells are transferred to the naïve culture medium after about 1-4 weeks, preferably after about 2 weeks in the first medium.

In some embodiments, when the cell is cultured in the second medium, the medium may be replaced at least daily, or twice daily. The second medium may be replaced every 1-5, 1-4, 1-3, or 1-2 days. In preferred embodiments the second medium is replaced daily.

In some embodiments, when the cell is cultured in the second medium, the cells may be dissociated every 3-10, 4-8, or preferably 5-7 days, for example using accutase. The cells may be replated as single cells.

Cells may be cultured on feeder cells throughout the reprogramming protocol, for example on MEF feeder cells.

In preferred embodiments the cells are cultured in the absence of feeder cells. In these embodiments, the concentration for the protein kinase C (PKC) inhibitor (e.g.

Gö6983) is chosen to allow culture in the absence of feeders. For example, the concentration may be about 1-3 μm, for example about 2 μm.

Cells may be cultured in the absence of feeder cells during resetting and/or sustaining. In some embodiments cells are cultured on matrix-coated plates, for example on Matrigel.

Uses of Inhibitors of Intracellular Signalling Cascades

During at least part of the reprogramming process as described herein, the cell is maintained in the presence of kinase inhibitors which inhibit kinases responsible for an intracellular signalling cascade. These inhibitors may be used in the methods of the invention as described elsewhere herein.

The cells may be maintained in the presence of a MEK inhibitor and GSK3 inhibitor. Together this inhibitor combination may be referred to as 2i. The cells may be cultured in a medium comprising:
(i) an MEK inhibitor and a GSK3 inhibitor, and
(ii) LIF.

This combination may be referred to as 2iL. In some embodiments that STAT3 activator is LIF, preferably hLIF.

It will be understood that other kinase inhibitors which inhibit a kinase responsible for an intracellular signalling component of the same cascades (e.g. MAPK/ERK, for example ERK1 or ERK2 cascade) may be substituted where desired for the MEK inhibitor or GSK3 inhibitor in the first or second medium. This may include inhibition of an upstream stimulus of the MAPK pathway, in particular through the FGF receptor (Ying, Nature, 2008). Likewise the LIF may be substituted where desired for other activators of Stat3 or gp130 signalling.

Inhibitors may be provided or obtained by those skilled in the art by conventional means or from conventional sources, and such inhibitors per se are not part of the present invention (see also WO2007113505).

Reference to GSK3 inhibition refers to inhibition of one or more GSK3 enzymes. The family of GSK3 enzymes is well-known and a number of variants have been described (see e.g. Schaffer et al.; Gene 2003; 302(1-2): 73-81). In specific embodiments GSK3-β is inhibited. GSK3-α inhibitors are also suitable, and in general inhibitors for use in the invention inhibit both GSK3-α and GSK3-β. A wide range of GSK3 inhibitors are known, by way of example, the inhibitors CHIR 98014, CHIR 99021, AR-AO144-18, TDZD-8, SB216763 and SB415286. In addition, the structure of the active site of GSK3-β has been characterised and key residues that interact with specific and non-specific inhibitors have been identified (Bertrand et al.; J Mol Biol. 2003; 333(2): 393-407). This structural characterisation allows additional GSK inhibitors to be readily identified.

The inhibitors used herein are preferably specific for the kinase to be targeted. The inhibitors of certain embodiments are specific for GSK3-β and GSK3-α, substantially do not inhibit erk2 and substantially do not inhibit cdc2. Preferably the inhibitors have at least 100 fold, more preferably at least 200 fold, very preferably at least 400 fold selectivity for human GSK3 over mouse erk2 and/or human cdc2, measured as ratio of $IC_{50}$ values; here, reference to GSK3 $IC_{50}$ values refers to the mean values for human GSK3-β and GSK3-α. Good results have been obtained with CHIR 99021 which is specific for GSK3. Examples of GSK3 inhibitors are described in Bennett C, et al, J. Biol. Chem., vol. 277, no. 34, Aug. 23 2002, pp 30998-31004 and in Ring D B, et al, Diabetes, vol. 52, March 2003, pp 588-595. Suitable concentrations for use of CHIR 99021 are in the range 0.01 to 10, preferably 0.1 to 5, preferably 0.1 to 11 μM.

Reference to a MEK inhibitor herein refers to MEK inhibitors in general. Thus, reference to a MEK inhibitor refers to any inhibitor a member of the MEK family of protein kinases, including MEK1, MEK2 and MEK5. Reference is also made to MEK1, MEK2 and MEK5 inhibitors. Examples of suitable MEK inhibitors, already known in the art, include the MEK1 inhibitors PD184352 and PD98059, inhibitors of MEK1 and MEK2 U0126 and SL327, and those discussed in Davies et al (2000) (Davies S P, Reddy H, Caivano M, Cohen P. Specificity and mechanism of action of some commonly used protein kinase inhibitors. Biochem J. 351, 95-105). In particular, PD184352 and PD0325901 have been found to have a high degree of specificity and potency when compared to other known MEK inhibitors (Bain, Biochem J. 2007). Other MEK inhibitors and classes of MEK inhibitors are described in Zhang et al. (2000) Bioorganic & Medicinal Chemistry Letters; 10:2825-2828. A preferred inhibitor combination is PD0325901 plus CHIR99021 used in the Examples below.

PKC inhibitors suitable for use in the present invention include 3-[1-[3-(dimethylamino)propyl]-5-methoxy-1H-indol-3-yl]-4-(1H-indol-3-yl)-1H-pyrrole-2,5-dione (Gö6983) (Gschwendt et al. 1996) or other compounds that selectively inhibit atypical protein kinase C isoforms and optionally also PKC delta.

The PKC inhibitor may be present in the second medium at a concentration of 0.01 to 10 μM, preferably, 0.1 to 5 μM, preferably 1 to 4 μM. Preferably the concentration of the PKC inhibitor is adjusted to allow culture growth in the absence of feeder cells (e.g. about 2 μM for Gö6983).

Another preferred PKC inhibitor is Ro-31-8425, which can be used analogously to Gö6983 (for example) at a concentration of 0.1 μM-1 μM.

It will be understood that where the term 'FGF receptor inhibitor' is used herein, it can be substituted with any FGF inhibitor, i.e. an inhibitor of FGF signalling. FGF receptor inhibitors suitable for use in the present invention include PD173074.

Inhibition of MEKs, GSK3 and PKC can also be conveniently achieved using RNA-mediated interference (RNAi). Typically, a double-stranded RNA molecule complementary to all or part of a MEK gene is introduced into the stem cells, thus promoting specific degradation of MEK-encoding mRNA molecules. This post-transcriptional mechanism results in reduced or abolished expression of the targeted MEK gene. Suitable techniques and protocols for achieving MEK inhibition using RNAi are known.

Accordingly, references herein to an inhibitor herein, encompass RNAi as an inhibitor.

A number of assays for identifying kinase inhibitors, including GSK3 inhibitors and MEK inhibitors, are known. For example, Davies et al (2000) describe kinase assays in which a kinase is incubated in the presence of a peptide substrate and radiolabelled ATP. Phosphorylation of the substrate by the kinase results in incorporation of the label into the substrate. Aliquots of each reaction are immobilized on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) J Biol Chem.; 271(35): 21005-21011 also describes assays for kinase activity which can be used to identify kinase inhibitors.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

Applications

Reset or embryo-derived ground state human pluripotent stem cells provide a superior starting material for various applications because of their homogeneity and absence of lineage priming or epigenetic restrictions that bias differentiation behaviour.

Human ground state cells may be applied to define benchmarks for human pluripotent stem cells and enable the field to adopt common standards, in particular for induction of pluripotency by molecular reprogramming.

Further uses include: differentiation to create cell culture models of human development and disease that can be applied in drug discovery and development, and in teratogenicity and toxicology testing; source of tissue stem cells and more mature cells for applications in clinical cell therapy; analysis of the relative contributions of genetics and epigenetics to developmental disorders, genetic disease and quantitative traits to facilitate advances in diagnostics, prognostics and patient treatment; generation of tissues and organs for transplantation either by bioengineering in vitro or by lineage/organ specific contribution to human-animal chimaeras.

Reset or embryo-derived ground state pluripotent stem cells from non-human primates and other mammals can be used for precision genome engineering to enhance or modify germline genetic constitution of animals. Germline modification is achieved by genome engineering or genome editing and clonal selection of ground state cells in culture, followed by production of chimaeras, breeding and screening for transmission of the modified genotype. Desired genetic alterations include single or multiple gene deletion, point mutation, or substitution. Chromosome-scale genome modifications/substitutions are also possible. Applications include: disease models; behavioural models; host compatibility for xenotransplantation and organ substitution; pharmaceutical, antibody and vaccine production; livestock improvement; breeding stock preservation and improvement. Non-human primate ground state cells may also be used in pre-clinical testing and evaluation of cell therapies.

In one aspect, the invention provides uses of cells in naïve state and cells reset using the methods herein for the above applications, and methods of using these cells in the above applications.

FIGURES

FIG. 1 Resetting the human PSC phenotype

Figure 12:
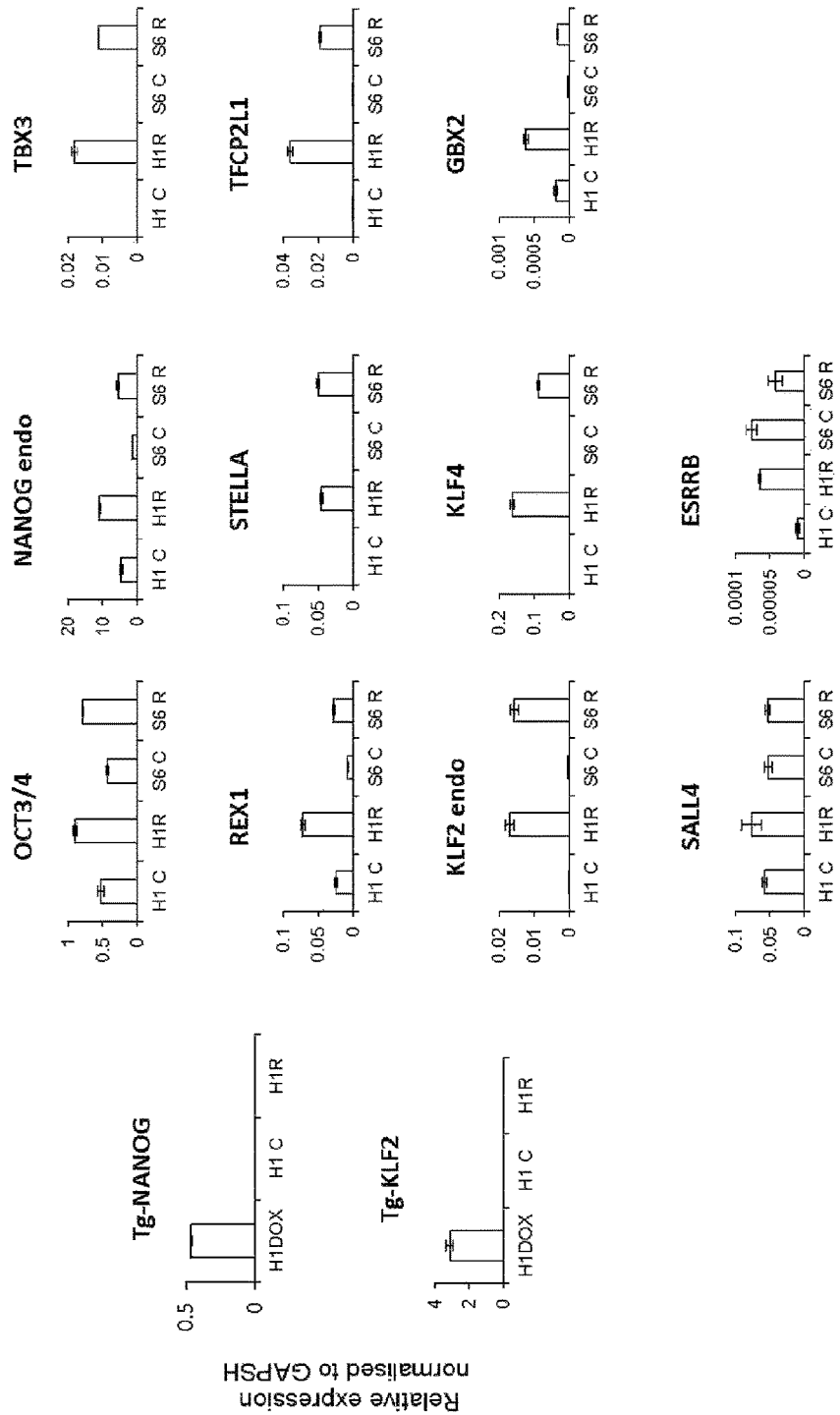

Data in this and other figures are from H9 cells, unless otherwise indicated, but similar results were obtained for H1 and Shef6 embryo derived cells and with various iPS cell lines (Table 1, FIG. 12, 13)

A. Induction or silencing respectively of NANOG and KLF2 transgenes combined with switching between 2iL and FGF/KSR supports expansion of colonies with distinct morphology. Transgene expression is indicated by the Venus reporter. Note that DOX-induced cells do not expand in FGF/KSR and conversely non-induced cells do not thrive in 2iL.

B. PKC inhibitor Gö6983 maintains the reset state in the absence of transgene expression. Upon DOX withdrawal cells in 2iL degenerated. Addition of Gö6983 (Gö) maintained cell proliferation and compact colony morphology, even after extended passaging. Note that intrinsic fluorescence of Gö produces a faint red background signal.

C. Expansion of reset cells in different CH concentrations. Cells were plated at $5 \times 10^4$ cells per well and cultured for 4 days in PD03 (1 µM) with LIF, and 0, 1, or 3 µM CH. Y axis indicates cell number ($\times 10^4$).

D. Colony formation in the presence of PKC inhibitor Gö6983 (Gö). Cells previously cultured in t2iL with DOX were plated without ROCKi on MEF feeders in 6 well dishes at 5000 cells/well in the indicated conditions. Colonies were stained for alkaline phosphatase after 10 days.

E. Colony forming assay. Cells maintained in t2iL+Gö were seeded without ROCKi at 2000 cells/well in 12 well dishes in t2iL+Gö plus FGF receptor inhibitor PD17 or TGF-β/activin receptor inhibitor A83-01. Colonies were stained for alkaline phosphatase after 7 days.

F. Cell proliferation analysis. X axis shows cumulative passage number in t2iL+Gö for reset. H9 and a H9.8 subclone along with reset cells generated from adipose cell derived iPS cells (AdiPS), and fibroblast derived iPS cells (FiPS). Cells were cultured in triplicate well seeded with $1 \times 10^5$ cells and passaged every 6 days, counting at each passage and reseeding at the starting density.

G. G-banded karyotype of reset H9 cells at passage 16 in t2iL+Gö (reset at original passage number 40).

H. Up-regulation of ground state transcription factor transcripts. qRT-PCR assay on reset H9 cells.

I. Immunofluorescence staining for ground state pluripotency markers. Note that TFE3 is translocated to nuclei in reset cells. The dot of red debris in the TFCP2L1 image of reset cells is attributed to intrinsic fluorescence of Gö.

J. Immunoblotting for ground state pluripotency proteins in conventional and reset H9 cells.

K. Colonies of reset cells cultured on Matrigel or Laminin 511-E8.

L. qRT-PCR assay for ground state transcription factors in feeder-free cultures of reset cells. RNA was extracted after 5 passages on Matrigel (Ma) or Laminin511-E8 (La). Reset cells cultured on MEF and conventional PSC on matrigel in mTeSR provide reference controls.

Scale bars in FIGS. 1A and B are 100 µM and in panels 1I and K are 20 µM.

FIG. 2 Differentiation capacity

A. Expression of lineage markers in embryoid bodies. Reset cells in t2iL+Gö were dissociated and aggregated at 10,000 cells/well in V-bottom 96-well plates in the presence of either KSR or serum. Pools of ten embryoid bodies were assayed by qRT-PCR at day 5 and day 10.

B. Teratoma formation. Reset cells were grafted directly from t2iL+Gö into NOD/SCID mice ($10^5$ cells injected per kidney capsule). Teratomas developed by 12 weeks in 3 out of 10 recipient mice. Tumour sections were stained with haematoxylin and eosin.

C. Reset cells in t2iL+Gö convert to conventional PSC morphology after transfer to FGF/KSR. Right hand panel shows typical colony 4 passages after transfer.

D. Ground state pluripotency factors are down-regulated in FGF/KSR. Reset cells maintained in t2iL+Gö were transferred to FGF/KSR and RNA was extracted at passages 5 and 18.

E. Colony formation after transfer into FGF/KSR. Reset cells were cultured in FGF/KSR for two passages, then 5000 cells/well were seeded in the presence of ROCKi in 12 well plates in either FGF/KSR or t2iL+Gö. Colonies were stained for alkaline phosphatase on day 7.

F. Definitive endoderm differentiation after activin and Wnt treatment. Flow cytometry shows around half of cells express both CXCR4 and E-cadherin at day 3. Immunofluorescence for SOX17 and FOXA2 was performed at day 4.

G. Neuronal differentiation after dual inhibition of activin/TGF-β and BMP pathways. Cells were fixed and stained for TUJ1 and NEUN at day 10.

Scale bars in panels C, F, and G are 100 μM.

FIG. 3 Mitochondrial activity

A. Oxygen consumption rate (OCR). Measurements obtained using a SeaHorse Extracellular Flux analyser.

B. Mitochondrial staining. MitoTracker is a general stain whereas TMRE staining is dependent on mitochondrial membrane activity. Scale bar in the right hand panel is 10 μM and in the higher resolution view of Mitoracker staining is 25 μM C & D. Proliferation in 2-deoxyglucose. After single cell dissociation, $3\times10^4$ cells were seeded on 12 wells and cultured for 7 days with indicated concentrations of 2-deoxyglucose (2DG) or reduced glucose. ROCKi was added to conventional PSC.

FIG. 4 Epigenetic configuration

A. Immunofluorescence staining with antibodies against 5mC, 5hmC and NANOG. Conventional PSC exhibit pronounced 5mC staining (white arrow). Reset cells have a reduced 5mC signal (white arrow) while feeder cells in the same well show strong staining (unfilled arrow).

B. Quantitation by mass spectrometry of global 5mC and 5hmC levels.

C. Quantitative summaries from whole genome bisulphite sequencing (BS-seq).

D. Heatmaps of methylation levels in up to 10000 random samplings of previously classified genomic regions: promoters, separated into CpG islands (CGIs) or non-CGI promoters; intragenic and intergenic CGI; exons; introns; LINEs and SINEs. (Three biological replicates of conventional and reset H9 cultures).

E. Scatter plots of CGI methylation percentages in conventional and reset H9 cells. Probes were generated over CGIs and filtered for a minimum of 1 methylation count/CG and at least 5 CGs/CGI. Methylation values represent the mean over each CGI, filtered by chromosome. Note the distinctive intermediate methylation level on the X chromosome of conventional H9 cells that is lost in reset cells.

F. Immunofluorescence staining for H3K27me3. Two representative fields of reset cells in t2iL+Gö and after 2 passages in FGF/KSR. Images are counterstained with DAPI.

F. Immunofluorescence staining for H3K9me3. Intensity and distribution were analysed by Image J. Representative cell analyses shown, with further examples in supplemental information.

FIG. 5 Comparative transcriptome analysis

A. Principal component analysis of RNA-seq and microarray data from this study (parental H9 and reset cells) together with RNA-seq data from Chan et al (standard conditions and 3iL), microarray data from Gafni et al (standard conditions and NHSM), and single-cell RNA-seq data on human embryos and primary cultures from Yan et al. Samples generated in this study from reset H9 and iPS cells were hybridised to the identical array platform (Affymetrix Human Gene 1.0 ST) as used by Gafni et al. to facilitate direct comparison. Data were normalized to conventional human embryo derived PSC cultured in standard conditions in each study (see Methods). Reset PSC comprise a distinct population that shares characteristics with mouse ground state ESC. In contrast alternative PSC reported in previous studies are not fundamentally altered from the standard human PSC identity. The same clustering is apparent when using RNA-seq data alone (FIG. 16), which discounts the influence of platform differences.

B. RNA-seq data from conventional human PSC, reset and 3iL cells reveals two major groups, with reset cells featuring expression patterns most similar to ESC. Expression of core pluripotency genes and repression of various lineage markers can be observed in reset cells, with the inverse trend evident in other PSC samples. Values displayed correspond to the expression in each sample scaled by the mean expression of each gene across samples (see Methods). Only genes for which a difference in expression was observed are displayed (ie scaled expression >1 or <−1 in at least one sample).

C. Reset cells display transcription factor hallmarks of the ground state and express canonical pluripotency markers largely consistent with ESC. Data are normalized to expression from conventional human PSC as above. Alternative culture regimes fail to induce critical ground state pluripotency regulators.

D. Reset cells feature down-regulation of lineage markers characteristic of conventional human PSC and differentiated cells. PSC propagated in 3iL or NHSM express various early lineage markers indicating they reside in a primed state similar to conventional PSC and distinct from ground state ESC.

E. Presence of KLF4 and TFCP2L1 in the human inner cell mass. Expanded blastocysts (day 7) were fixed and immunostained.

F. Co-expression of KLF4, TFCP2L1 and NANOG in reset cells. Combined immunostaining with antibodies raised in different species Scale bar in E and F is 50 μM.

FIG. 6 Functional interrogation of transcription factor circuitry

A. Colony formation after siRNA knockdown. Single siRNAs were transfected to 4000 cells in FGF/KSR or 2000 cells in t2iL+Gö. Resulting colonies were stained with alkaline phosphatase and counted after 7 days. Colony size is variable for conventional PSC, but numbers are relatively consistent. Histogram shows mean colony counts from duplicate assays.

B. Colony formation after shTFCP2L1 knockdown (KD). 4000 cells were seeded per well in of 12 well dishes t2iL+DOX or 2iL+Gö and cultured for 7 days before staining for alkaline phosphatase.

C. Quantification of alkaline phosphatase positive colony formation by shTFCP2L1 or shKLF4 knockdown cells.

D. Rescue of KLF4 knockdown with human KLF4. Knockdown cells maintained by DOX induction of transgenes were transfected with a piggyBac human KLF4 expression vector and transfectant pools established by selection with hygromycin. Cells were then plated at 2000 cells/well in 24 well plates in t2iL+Gö without DOX and stained for alkaline phosphatase after 7 days.

E. Colony formation by shTFCP2L1 knockdown cells transfected with ESRRB expression plasmid. Transfection and assay as in D.

F. Integration into the mouse ICM after morula aggregation. FiPS-derived reset cells expressing Cherry were aggregated with mouse morulae. After 48 hours in vitro culture blastocysts were examined. Six out of 42 embryos contained cherry positive human reset cells. No contribution was detected in 37 embryos injected with convention FiPS cells. Example shows integration of Cherry positive reset cells within the mouse epiblast of the late blastocyst G. Integration into the mouse ICM after blastocyst injection. FiPS-derived reset cells constitutively expressing GFP were injected into mouse blastocysts. After 72 hours of culture most embryos had hatched and begun to outgrow on the substrate. Nine of 32 showed GFP positive cells in the ICM/epiblast. Two examples are shown.

FIG. 7 Resetting by transient transgenesis

A. Time course of transition from conventional PSC to reset status. $1\times10^5$ human embryo-derived PSC stably transfected with inducible NANOG and KLF2 constructs were seeded per well of 6 well plates in FGF/KSR. Dox was added the following day and 24 h later medium was switched to t2iL+Dox. At day 8, each cultures was dissociated to single cells and divided between 6 wells of 12 wells. Three wells were maintained in t2iL+DOX and three changed to t2iL+Gö without DOX. At day 15 cells were analysed by AP staining and KLF4 immunostaining. If Dox exposure is less than six days, few AP+ colonies are obtained. Scale bar is 100 µM.

B. Schema for generation of reset cells by transient transfection with non-linearised plasmids.

C. Phase contrast and EOS-GFP image of reset cells generated by transient transfection of H9 and Shef 6 cells.

D. Detection of transgene free cultures. Nine cultures expanded from colonies picked at passage 4 were analysed using Taqman copy number assay probes. TERT and RNase P were used as reference genes. 20 ng of DNA were used for each assay. Human iPS cells containing a blasticidin transgene provide a positive control (+) and a Dox inducible line serves as negative (−). Four technical replicates were analysed.

E. qRT-PCR assay for ground state transcription factors expression in expanded transgene-free reset cells.

F. Immunofluorescence staining for ground state pluripotency markers in expanded transgene-free reset cells. KLF4, TFCP2L1 and STELLA are up-regulated and TFE3 is translocated to nuclei. Staining was in parallel with H1 conventional PSC staining presented in FIG. 13.

G. Colony forming assays on transgene-free reset cells. Cells maintained in t2iL+Gö were seeded at 2000 cells/well in 24 well dishes in t2iL+Gö plus FGF receptor inhibitor PD17 or TGF-b/activin receptor inhibitor A83-01 and without ROCKi. Colonies were stained for alkaline phosphatase after 7 days.

H. Colony formation after siRNA knockdown in transgene-free reset cells. Single siRNAs were transfected to 2000 transgene-free reset cells in t2iL+Gö. Resulting colonies were stained with alkaline phosphatase and counted after 7 days. Histogram shows mean colony counts from duplicate assays.

I. Schematic representation of the ground state transcription factor circuitry in reset human cells. Ground state mouse ESC are characterised by expression of the essential pluripotency factors Oct4 and Sox2 plus a circuit of transcription factors that act cooperatively to sustain self-renewal but are individually dispensable. Apart from NANOG this circuit is lacking in conventional human PSC. Resetting induces expression of these factors in human cells with the exception of ESRRB. The ground state pluripotent identity is less robust in the absence of ESRRB and knockdown of single components, TFCP2L1 or KLF4, causes collapse. Introduction of ESRRB stabilises the human ground state as in mouse ESC and increases resistance to depletion of other factors.

Figure 8:
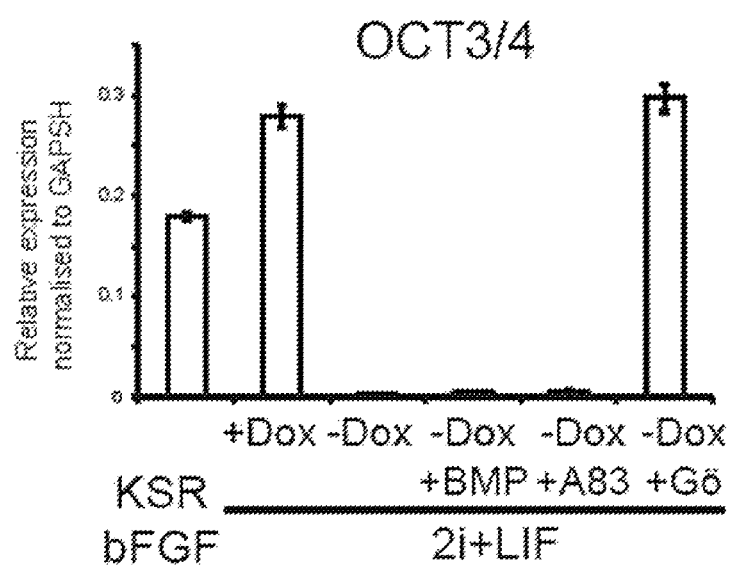

FIG. 8 OCT4 expression after withdrawal of DOX

OCT4 mRNA expression was measured by qRT-PCR

Figure 9:
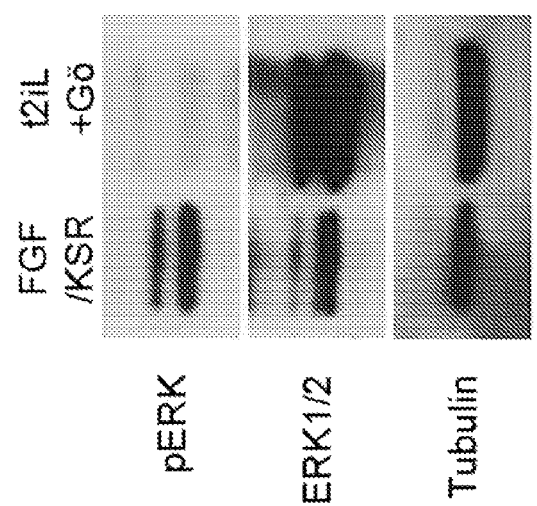

FIG. 9 Immunoblotting for ERK1/2 and pERK1/2.

Figure 10:
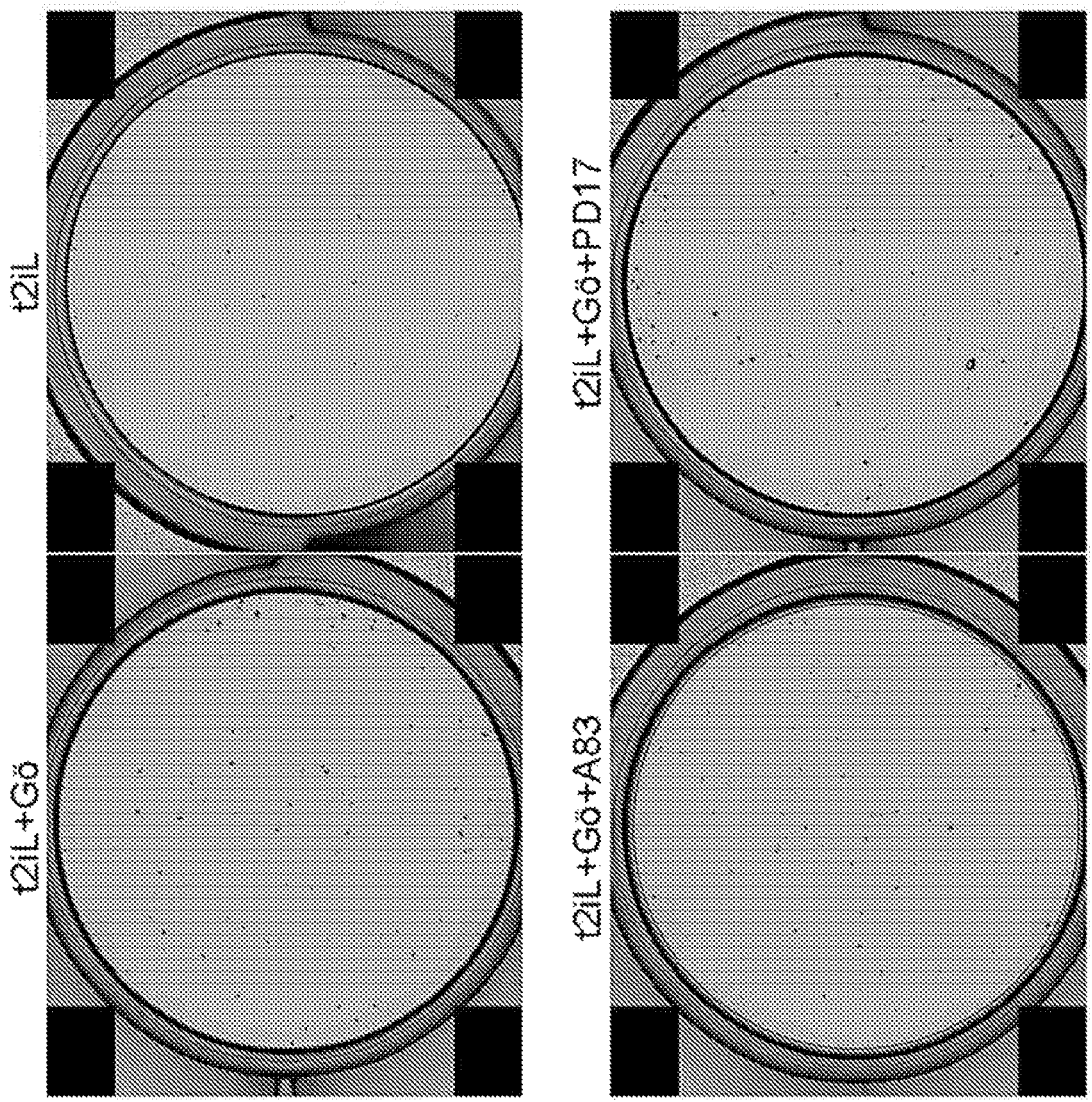

Protein was extracted from H9 cells cultured in FGF/KSR or reset in t2iL+Gö from a single well of 6-well plate ($1\times10^6$ cells) and one fifth of the sample fractionated by SDS electrophoresis, electroblotted and probed with indicated antibodies FIG. 10 Image of colony forming assay quantified in FIG. 1A.

Reset H9 cells maintained in t2iL+Gö were seeded without ROCKi at 2000 cells/well in 12 well dishes in t2iL+Gö. FGF receptor inhibitor PD173074 or TGF-β/activin receptor inhibitor A83-01 were added. Colonies were stained for alkaline phosphatase after 7 days.

Figure 11:
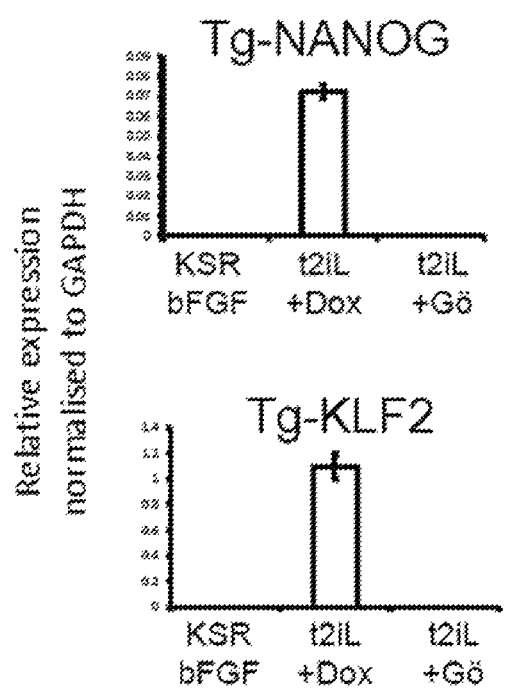

FIG. 11 Transgene specific qRT-PCR assay

H9 cells harbouring DOX-inducible NANOG and KLF2 transgenes were assayed in the indicated culture conditions.

FIG. 12 Up-regulation of ground state transcription factor transcripts.

qRT-PCR assay on reset H1 and Shef6 cells.

Figure 13:
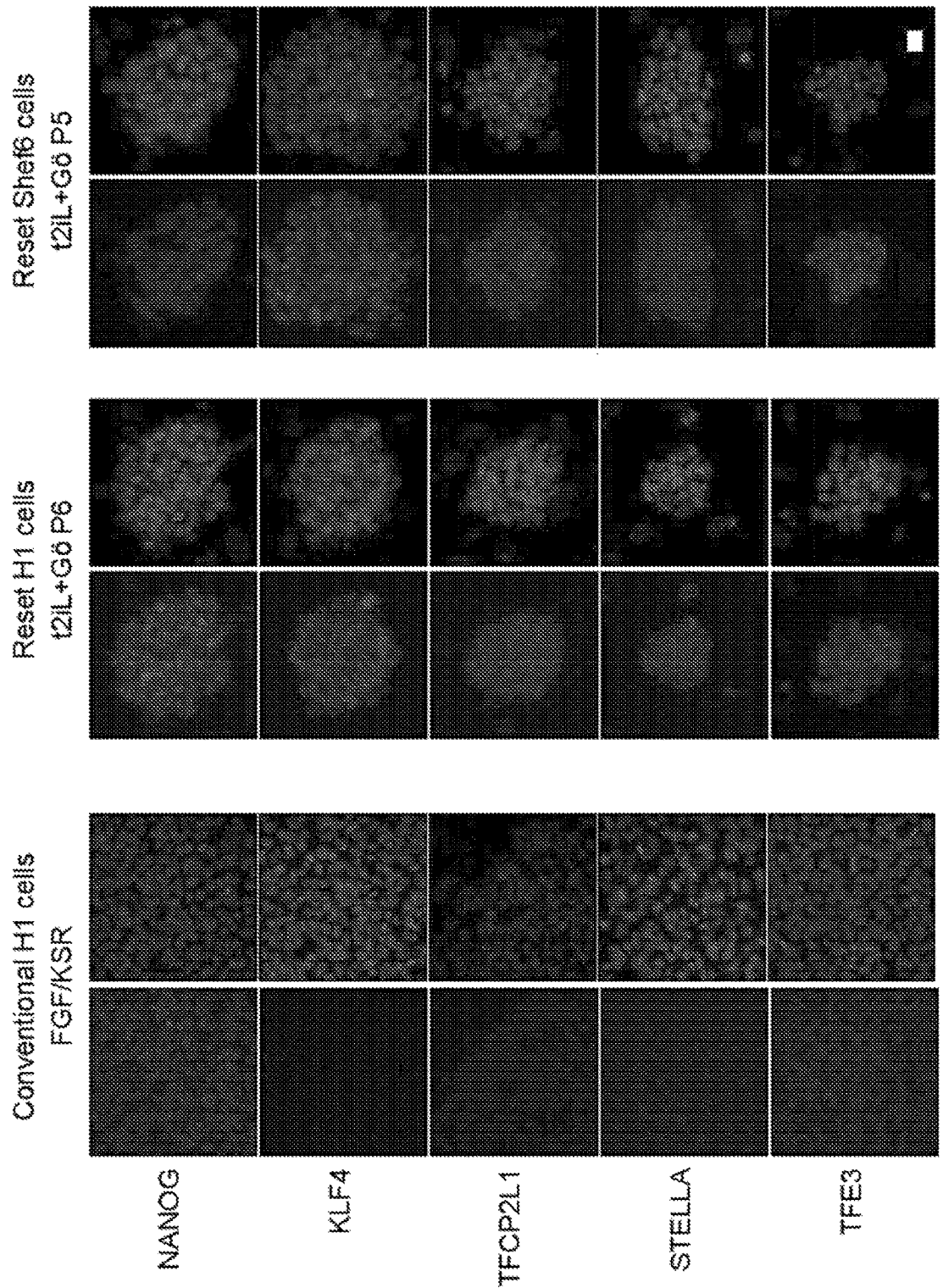

FIG. 13 Immunostaining for ground state pluripotency markers in.

Conventional and reset H1 and Shef 6 cells were stained with antibodies against the indicated markers. Note nuclear localization of TFE3 in reset cells.

Figure 14:
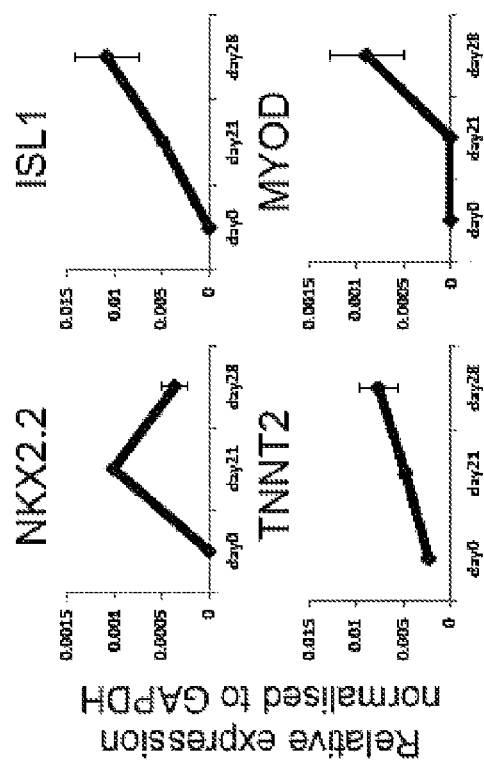

FIG. 14 Cardiac differentiation in embryoid body outgrowths.

H9 reset cells were differentiated according to Moretti et al. (2010). Initial beating cells were observed after three weeks of outgrowth in serum (Supplementary Movie). Cardiac gene expression was assayed by qRT-PCR at day 21 and 28.

Figure 15:
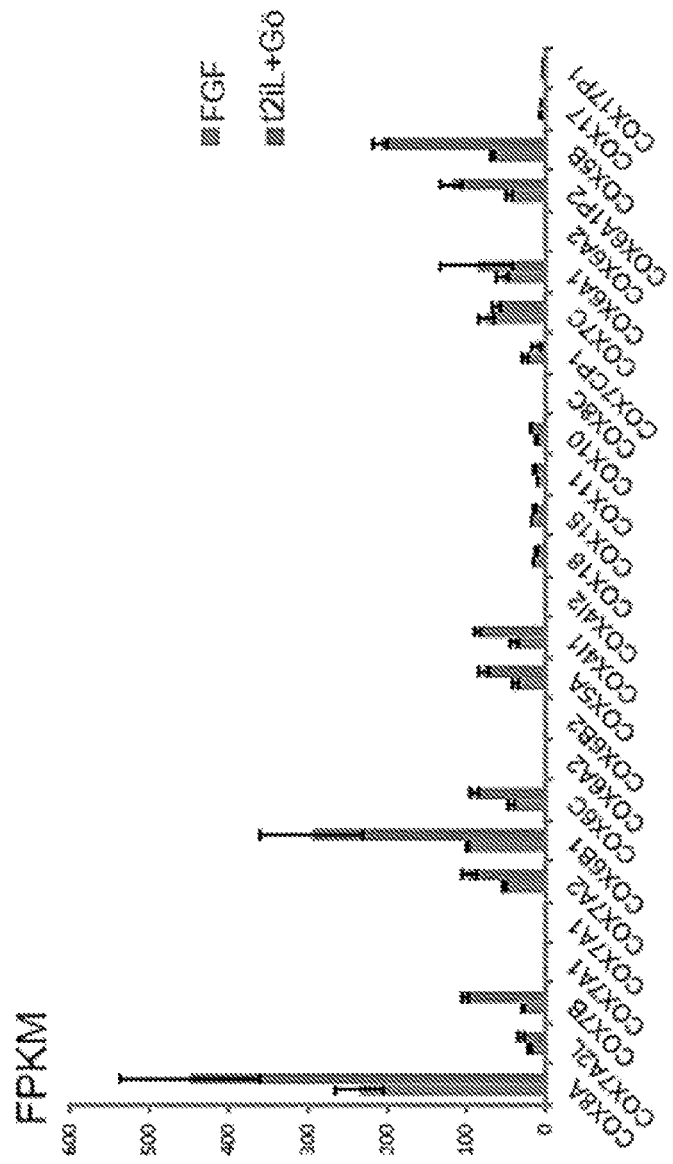

FIG. 15 COX gene expression determined from RNA-seq analysis

Data extracted from sample analysis in FIG. 5

Figure 16:
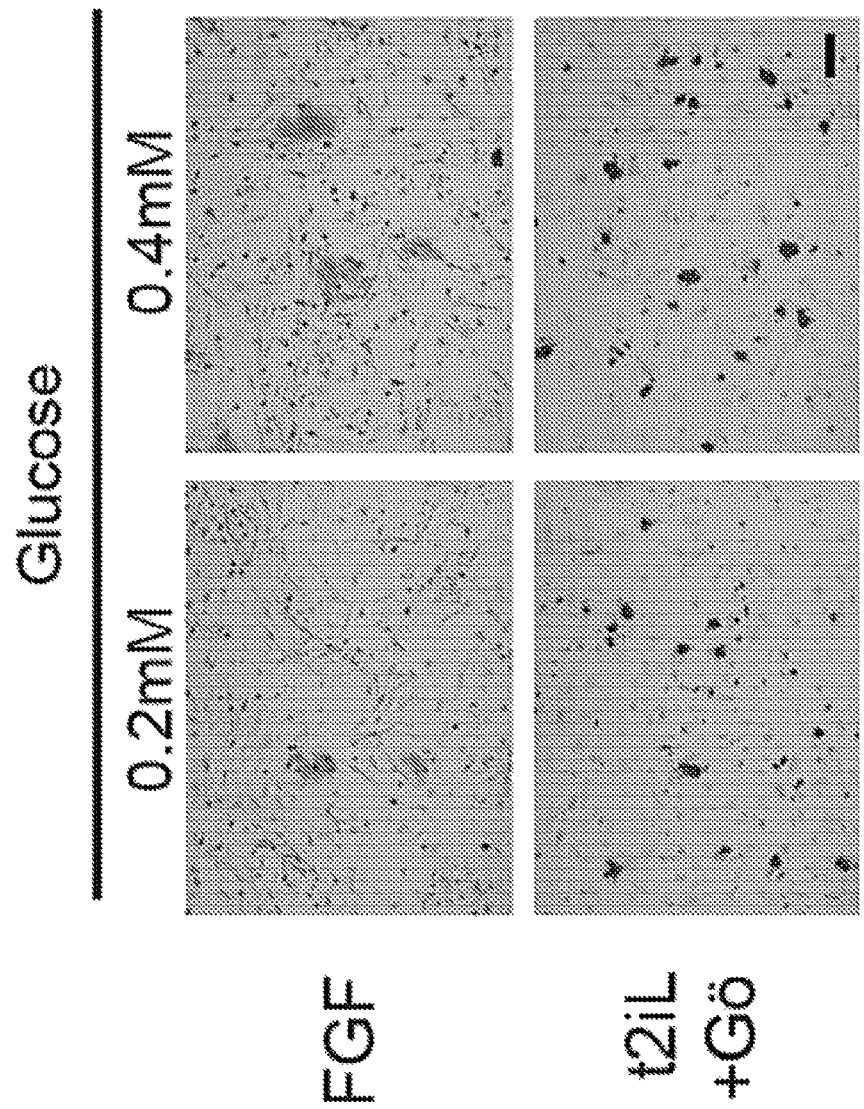

FIG. 16 Proliferation in low glucose.

After single cell dissociation, $3\times10^4$ cells were seeded on 12 wells and cultured for 7 days in the indicated concentrations of glucose. ROCKi was added for seeding conventional PSC. Conventional PSC failed to generate colonies. Reset cells are tolerant against low glucose produce multiple colonies. Scale bar is 200 µM.

FIG. 17 Sequencing coverage of whole-genome bisulfite sequencing libraries.

Figure 18:
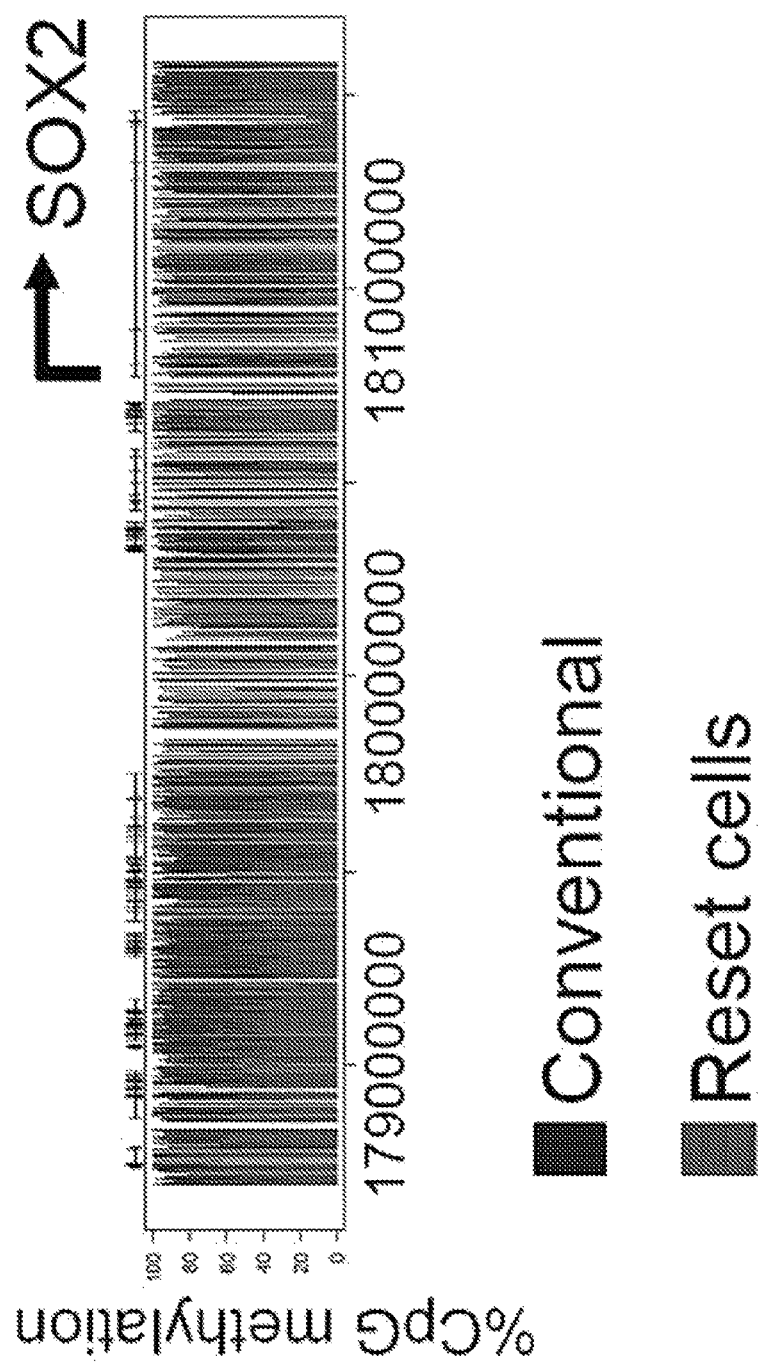
Figure 19A:
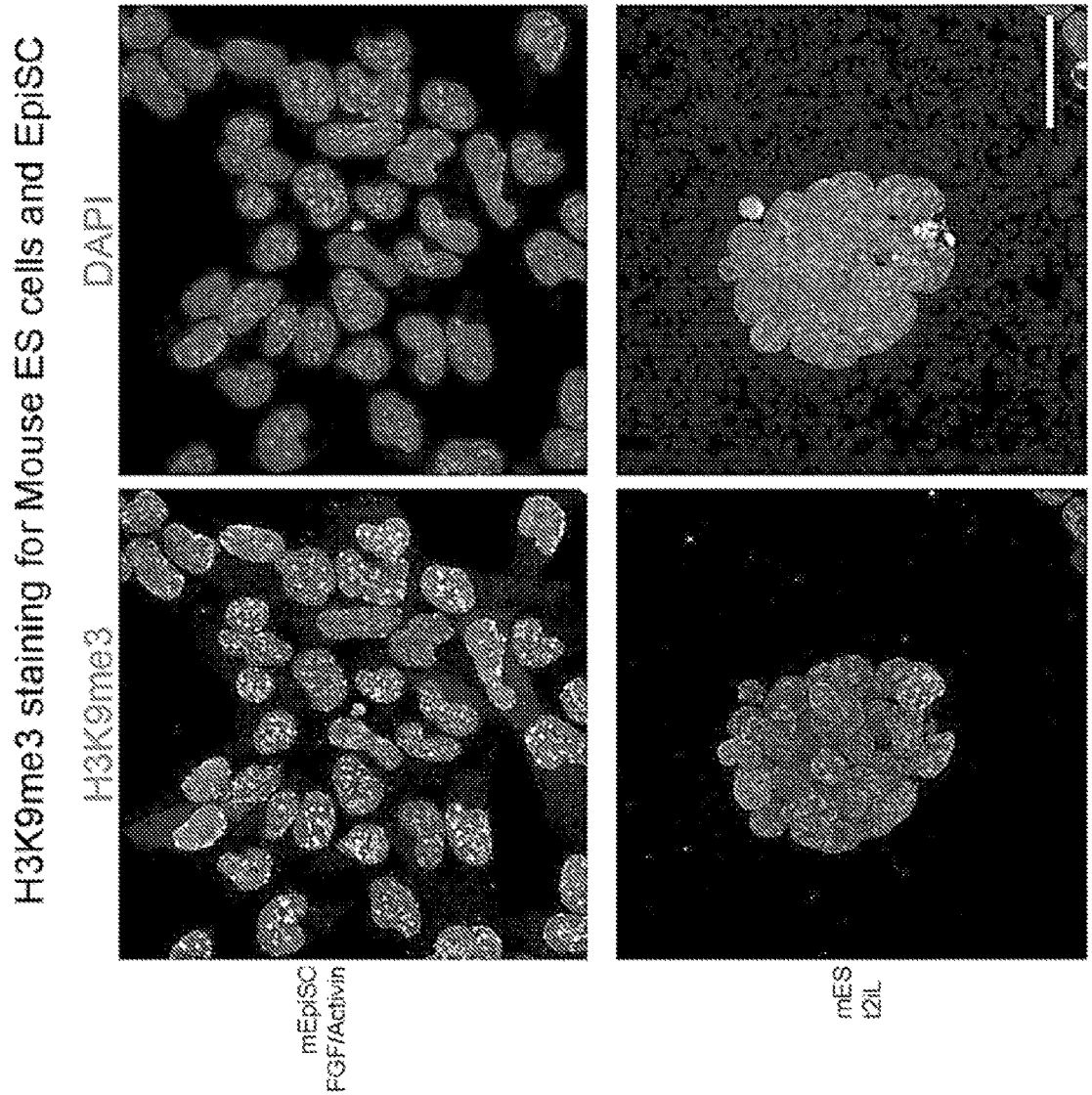
Figure 19B:
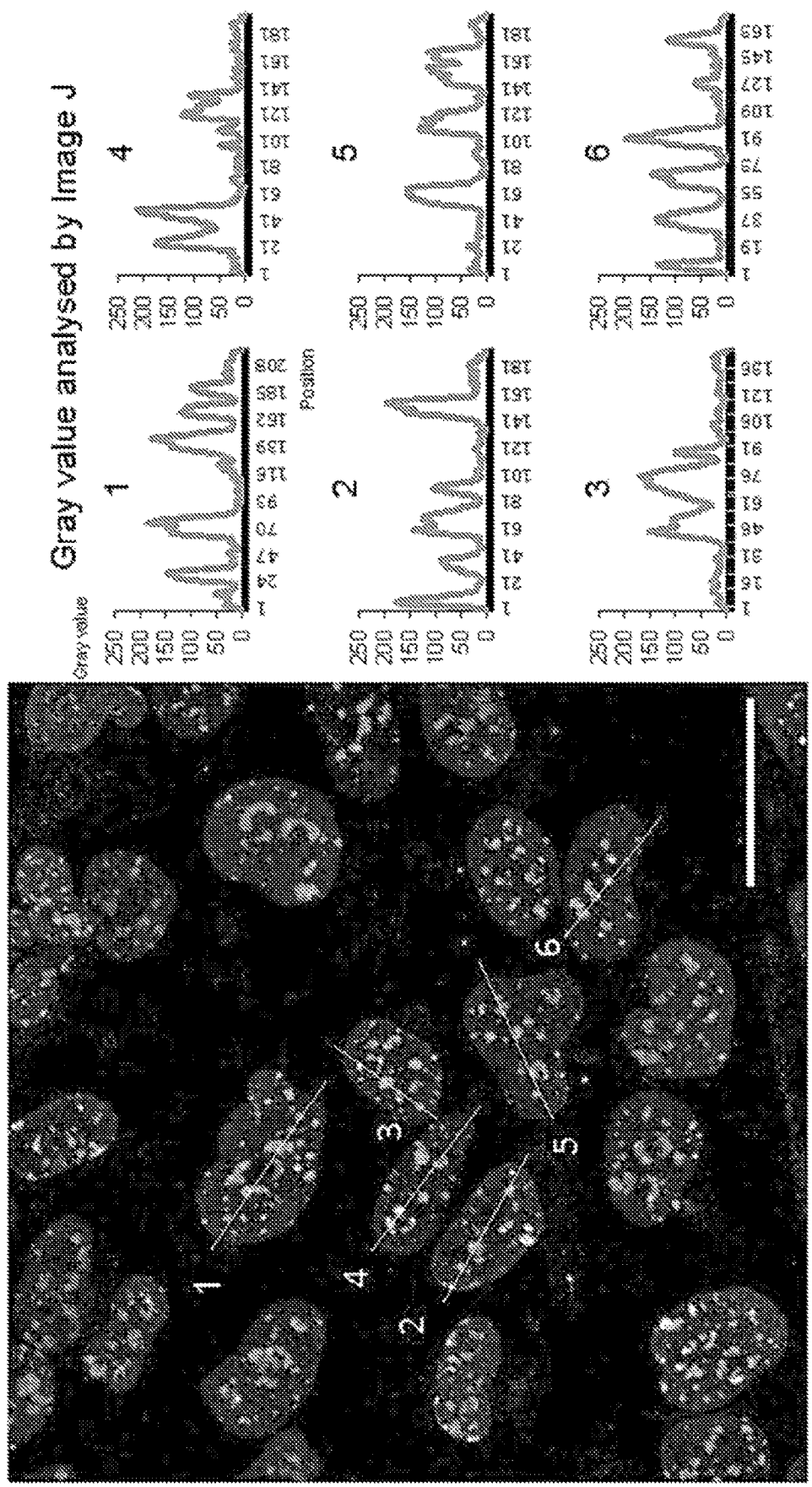
Figure 19C:
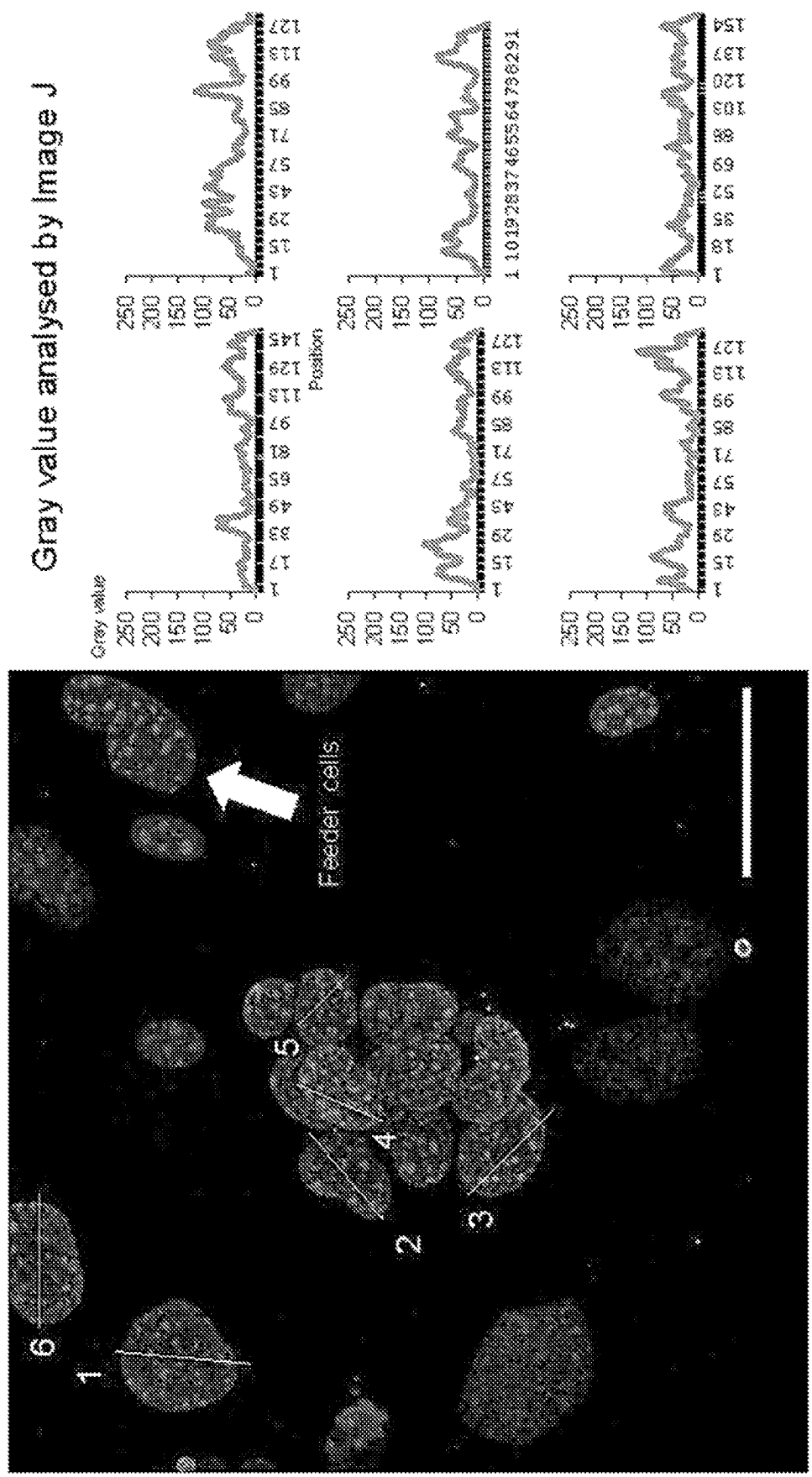
Figure 19D:
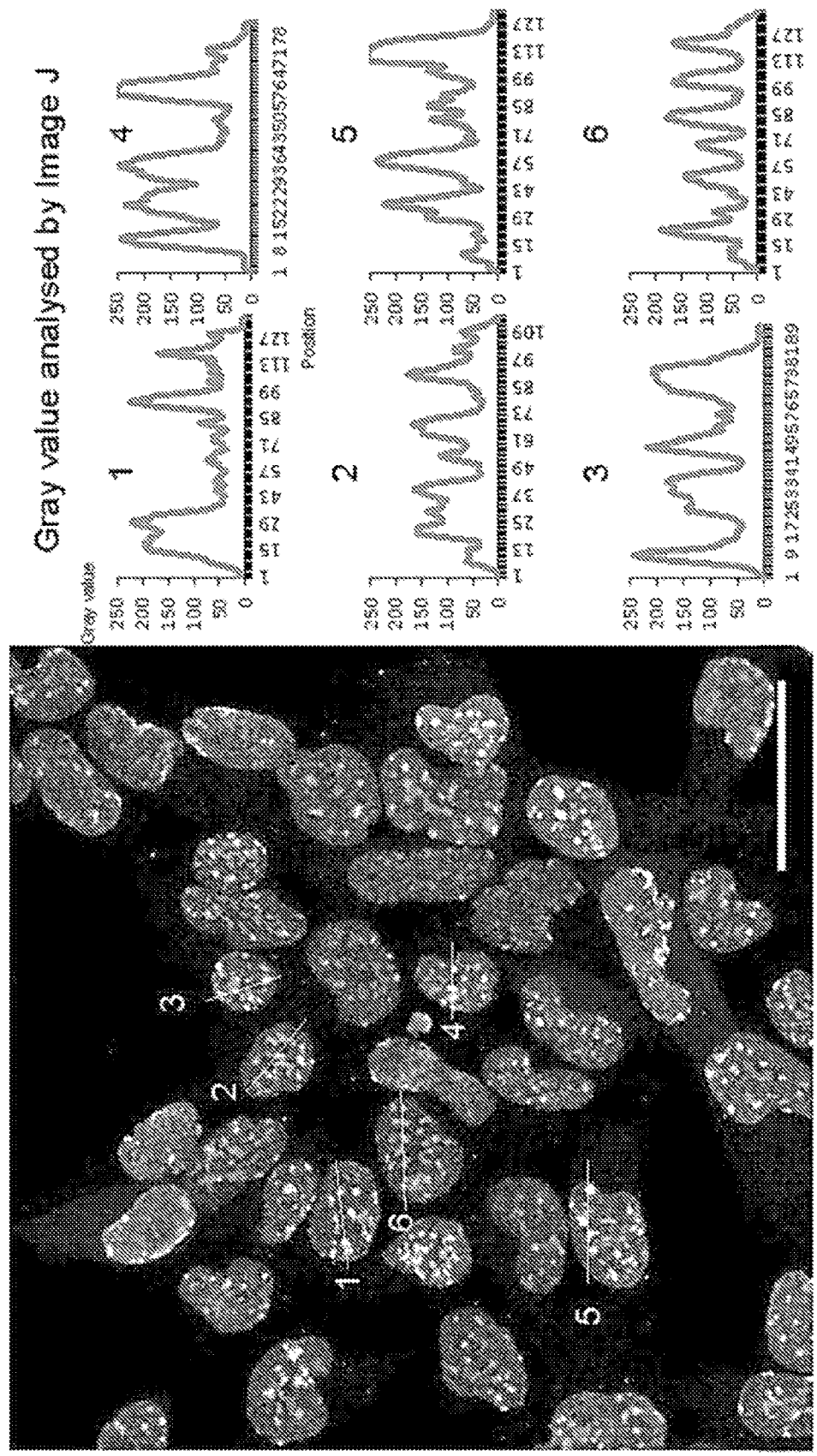
Figure 19E:
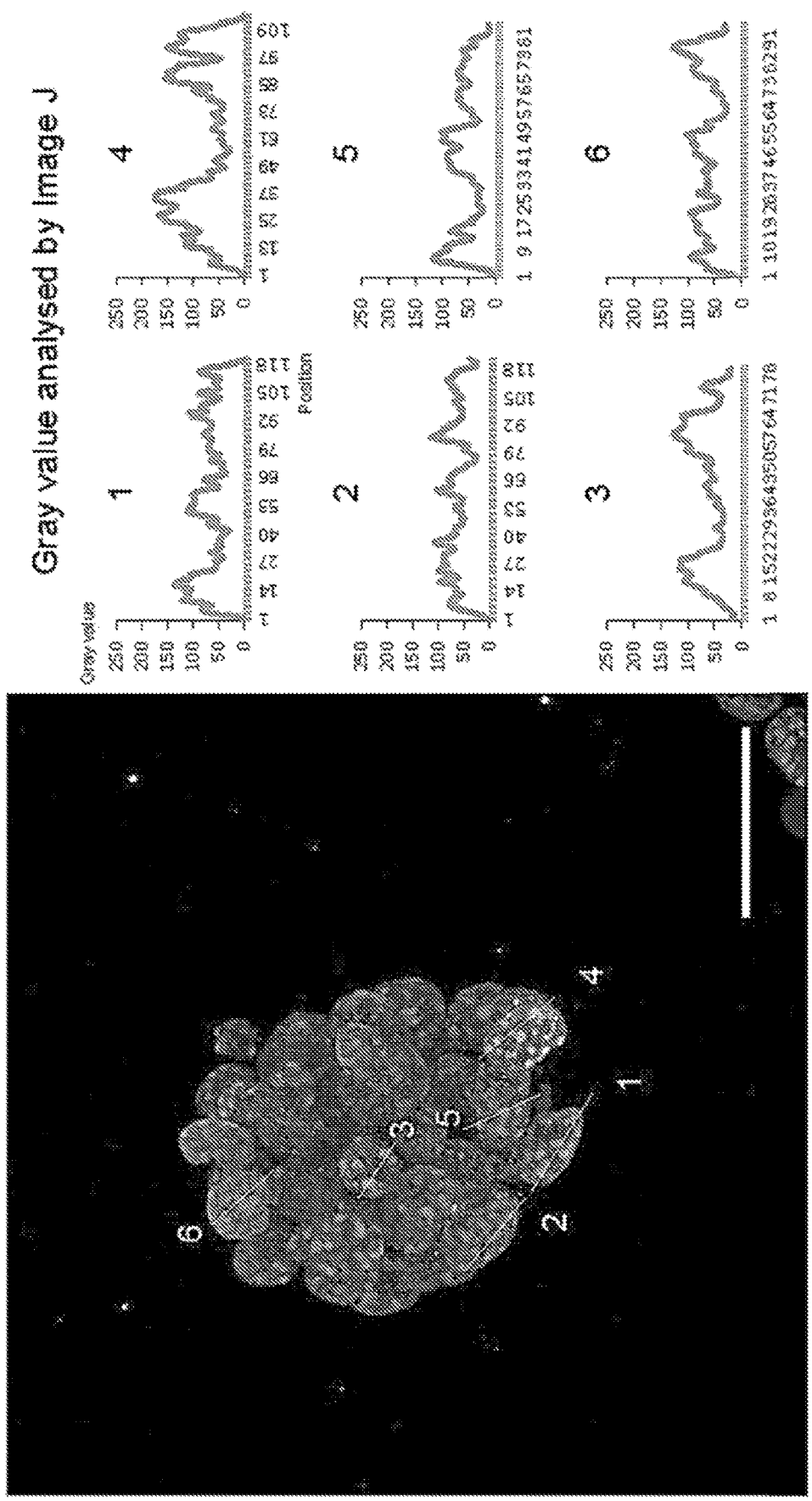

FIG. 18 BS-seq data for methylation at the SOX2 locus in conventional versus reset H9 cells.

FIG. 19 Immunofluorescence staining for H3K9me3.

A. Images of mouse post-implantation epiblast stem cells (EpiSC) in FGF/Activin and mouse ESC in t2iL. H3K9me3 appears in green and DAPI staining in blue.

B. Image analysis of H3K9me3 staining in conventional H9 cells in KSR/FGF-supplemented medium. Six cells were selected at random and intensity and distribution of staining were analysed by Image J.

C. Staining and analysis of H3K9me3 distribution in reset H9 cells t2iL+Gö. Images were analysed as in B.

D. H3K9me3 staining and analysis for mouse EpiSC in bFGF/Activin.

E. H3K9me3 staining and analysis for mouse ESC in t2iL. Scale bars are 20 µM.

Figure 20:
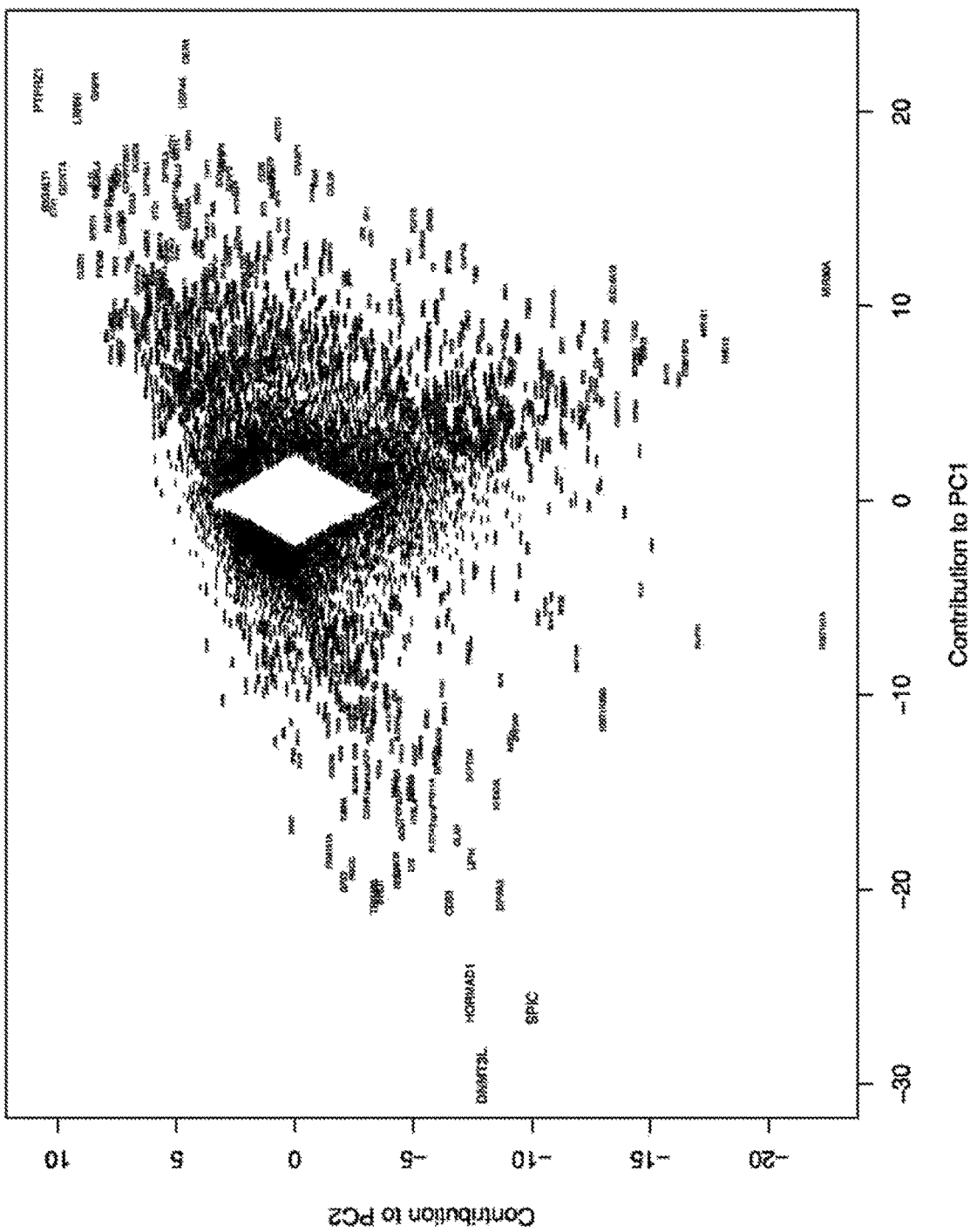

FIG. 20 Genes contributing to principal components distinguishing reset cells from conventional human PSC.

Gene symbols were extracted from the PCA and the labels scaled relative to the magnitude of variance. Pluripotency regulators are present in the leftmost area defining reset cells, whereas numerous lineage-specific genes can be found to the right expressed in conventional human PSC cultures.

Figure 21:
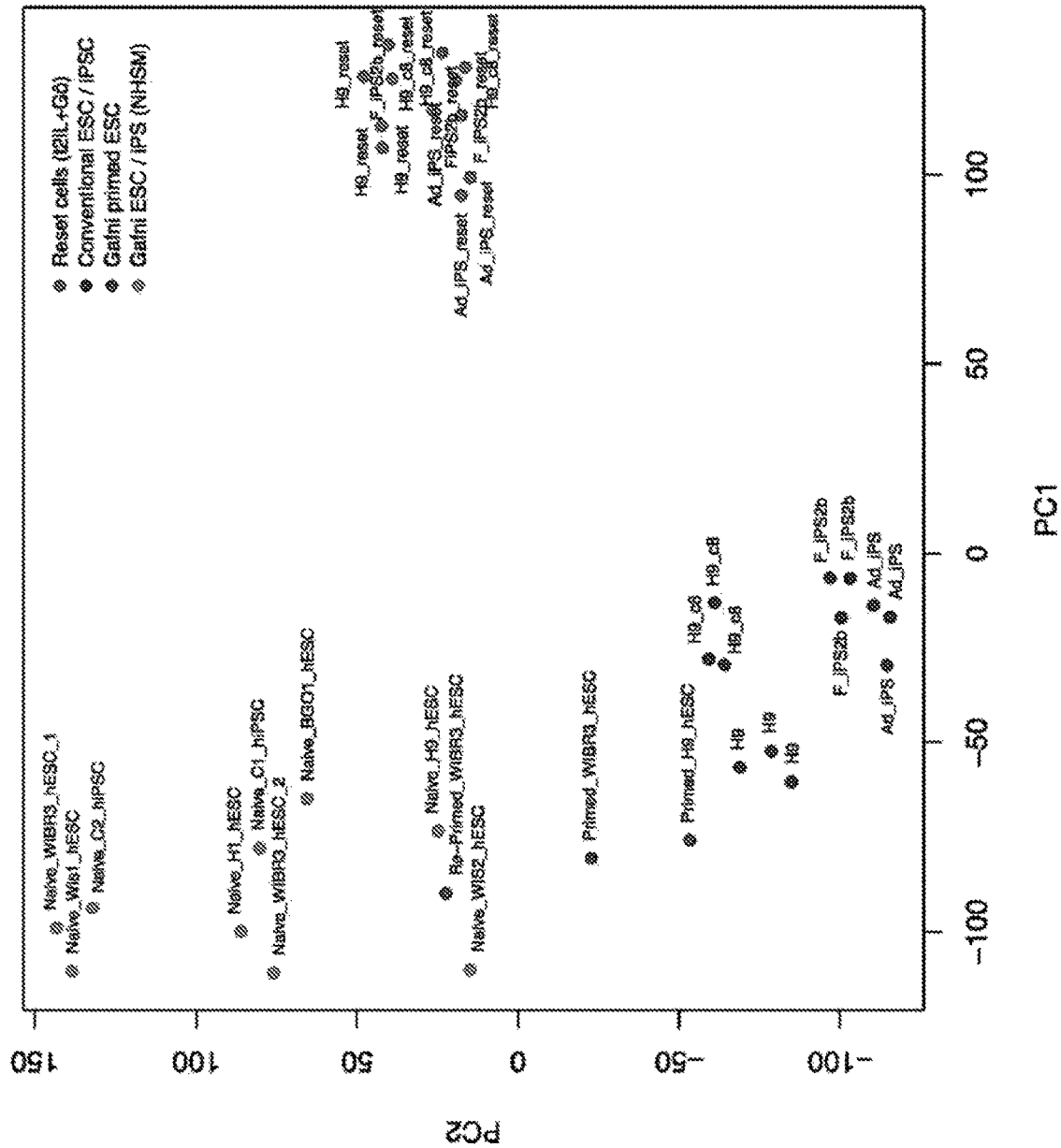

FIG. 21 Principal component analysis of microarray data from this study and those reported in Gafni et al.

Samples were hybridised to the same array platform to allow for direct comparison. Reset cells (light red) occupy a tight cluster to the right and conventional PSC (dark red) toward the bottom. Cells described as naïve in Gafni et al (violet) exhibit wide variation and appear unrelated to ground state cells.

Figure 22:
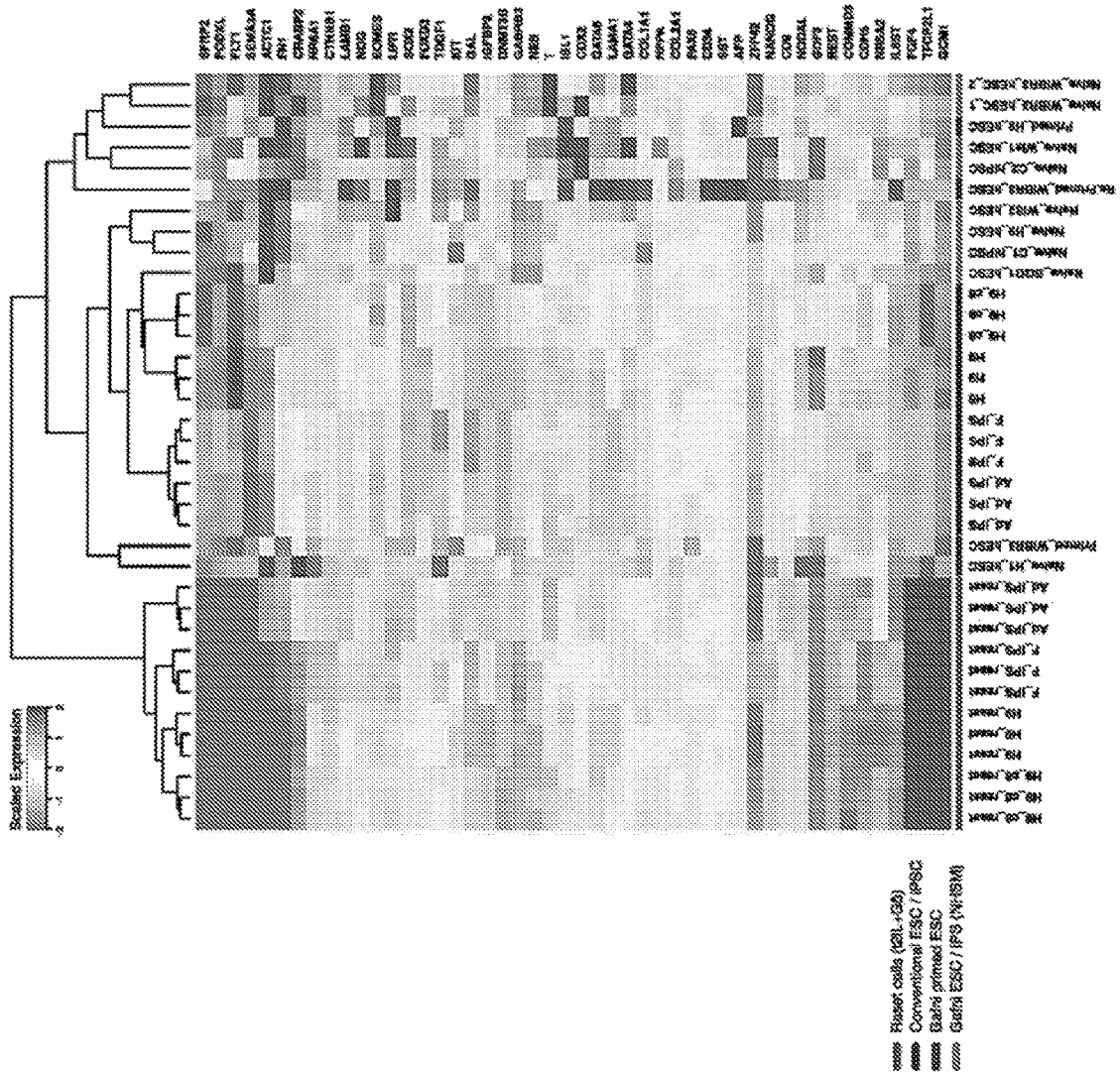

FIG. 22 Marker genes distinguish reset cells from conventional human PSC.

Heatmap comparing the expression of 48 pluripotency and lineage marker genes selected by the International Stem Cell Consortium (Adewumi et al., 2007b) between reset cells, conventional PSC cultures and those reported in Gafni et al, based on Affymetrix Human Gene 1.0 ST data. Reset cells form a distinct, relatively uniform population with robust expression of pluripotency genes and repression of lineage markers. In contrast, reportedly naïve cells from Gafni et al display many of the same traits as conventional PSC with mixed expression of lineage markers and a significant reduction in key pluripotency regulators. Only genes for which a difference in expression was observed are displayed (i.e. scaled expression >1 or <−1 in at least one sample).

Figure 23:
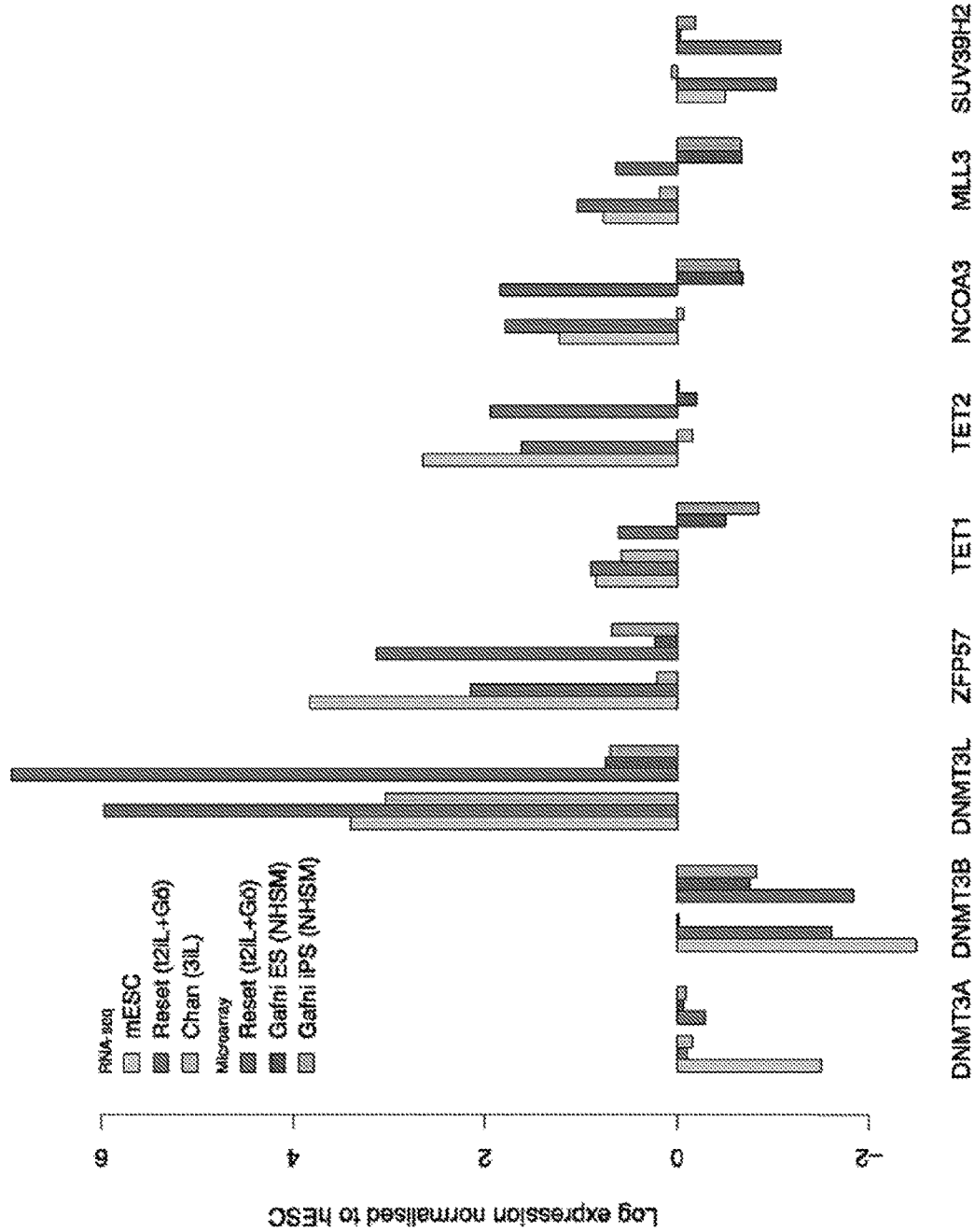

FIG. 23 Panel of chromatin modification genes associated with DNA methylation and demethylation, histone methylation and acetylation.

Expression trends in ground state ESC are recapitulated in reset cells, whereas weaker or divergent transcription is evident in PSC cultured in alternative conditions.

Figure 24:
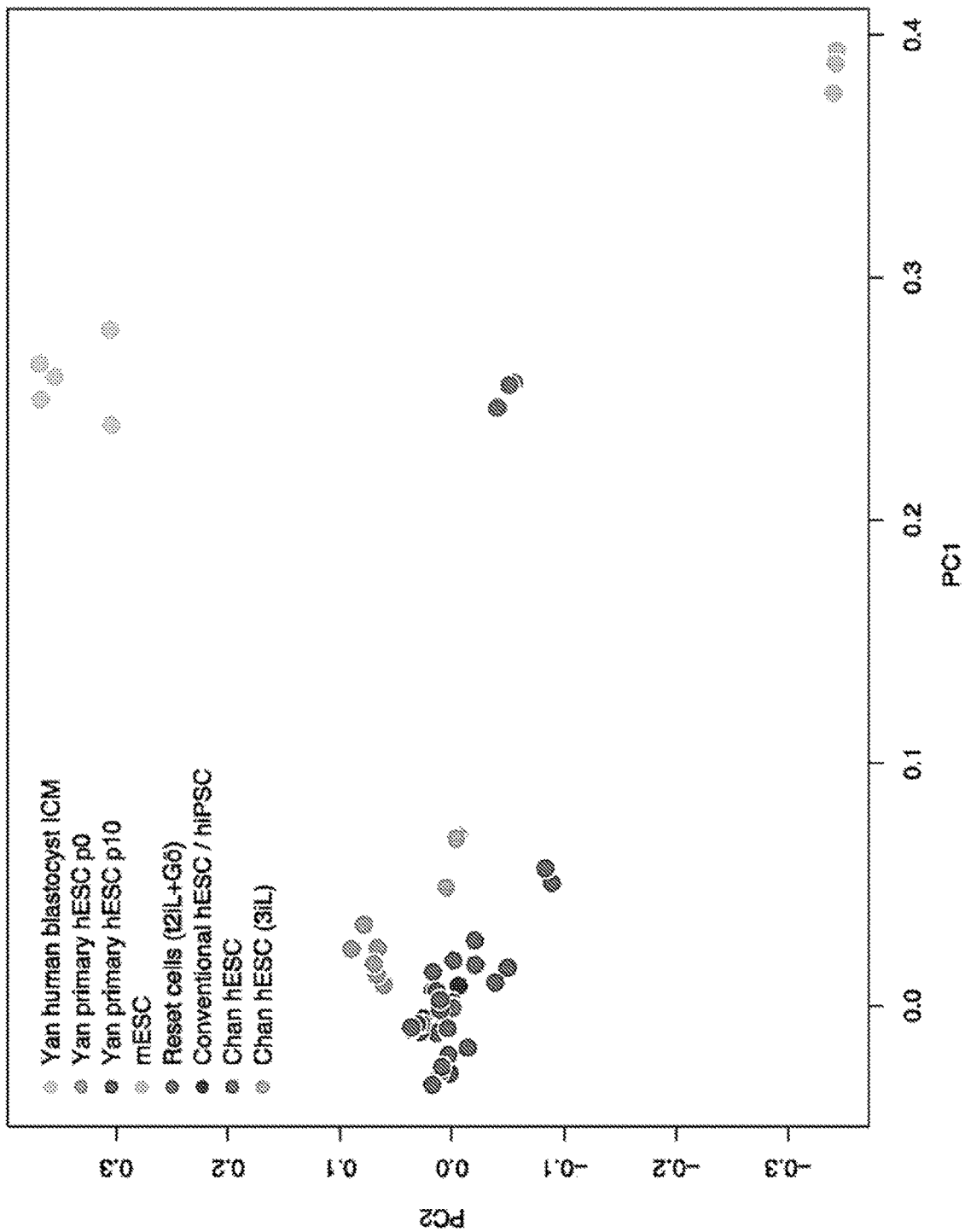

FIG. 24 Principal component analysis of RNA-seq data from reset cells, conventional PSC and 3iL samples from Chan et al.

Figure 5A:
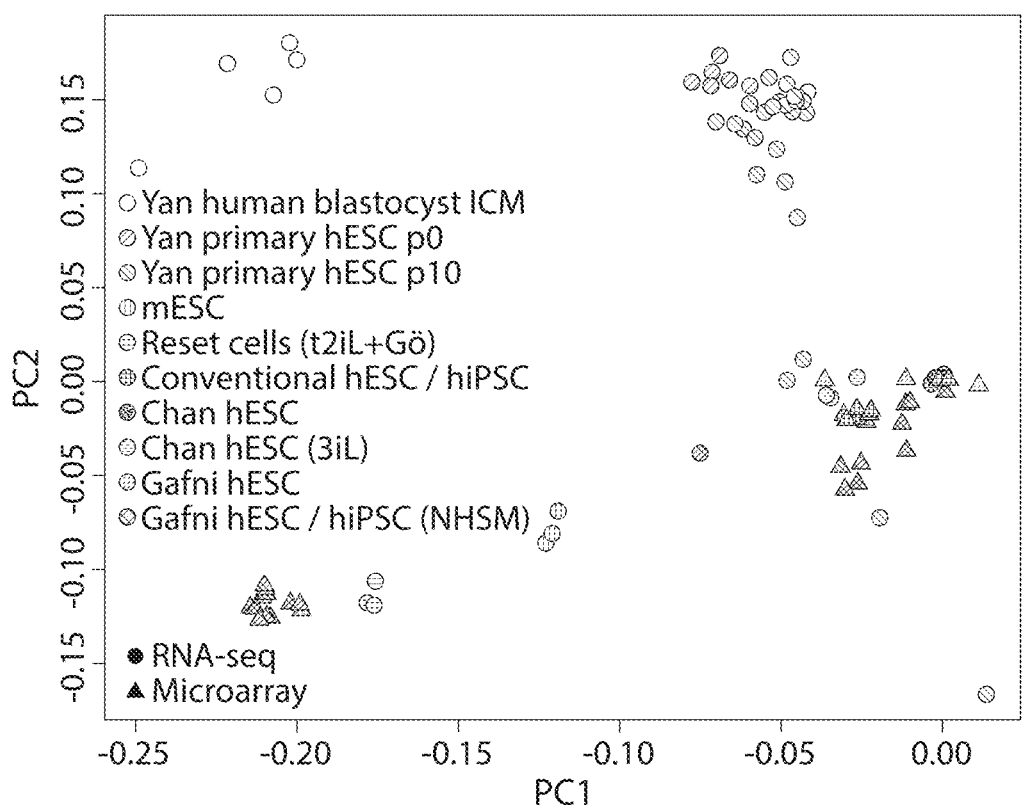

Clustering of each cell type when applied to a single technology recapitulates integrated analysis in FIG. 5A.

Figure 25:
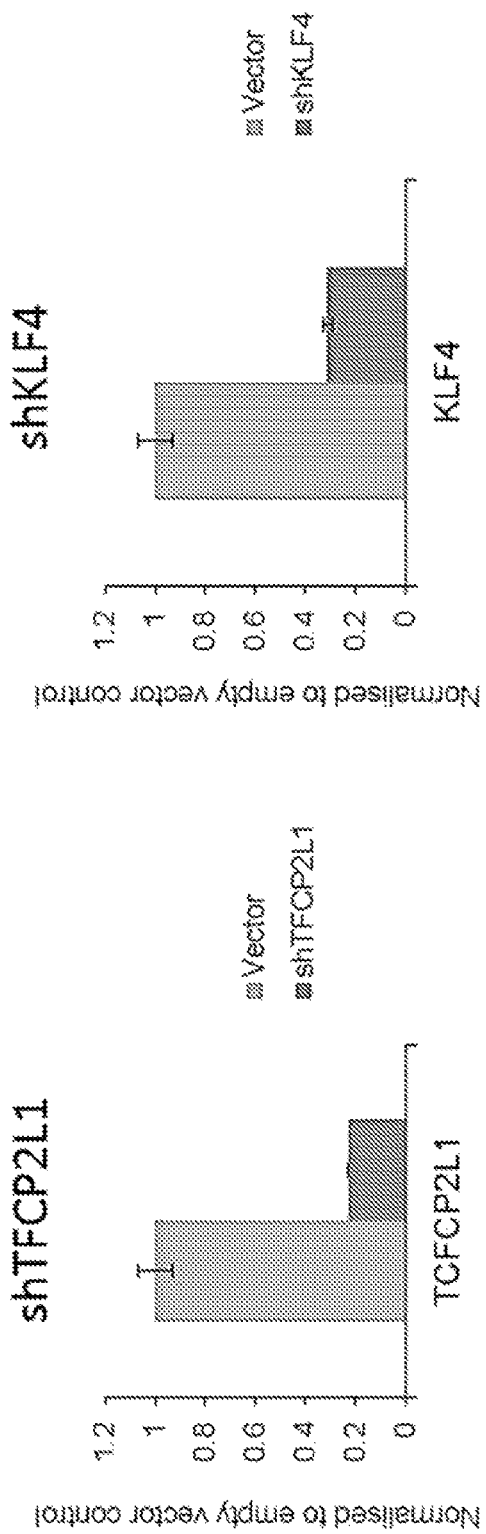

FIG. 25 shRNA knockdown of TFCP2L1 and KLF4

Knockdown cells and empty vector transfected cells were maintained by expression of NANOG and KLF2 transgenes in t2iL+DOX. Knockdown was evaluated by qRT-PCR.

Figure 26:
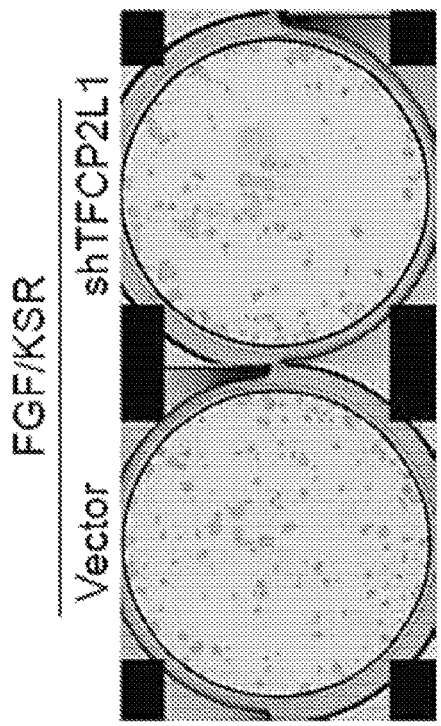

FIG. 26 Colony formation after shTFCP2L1 knockdown (KD) in FGF/KSR.

Parental H9 cells were stably transfected with empty vector or shTFCP2L1 construct and selected in puromycin. 4000 cells were plated in FGF/KSR with ROCKi in 12 well dishes.

Figure 27:
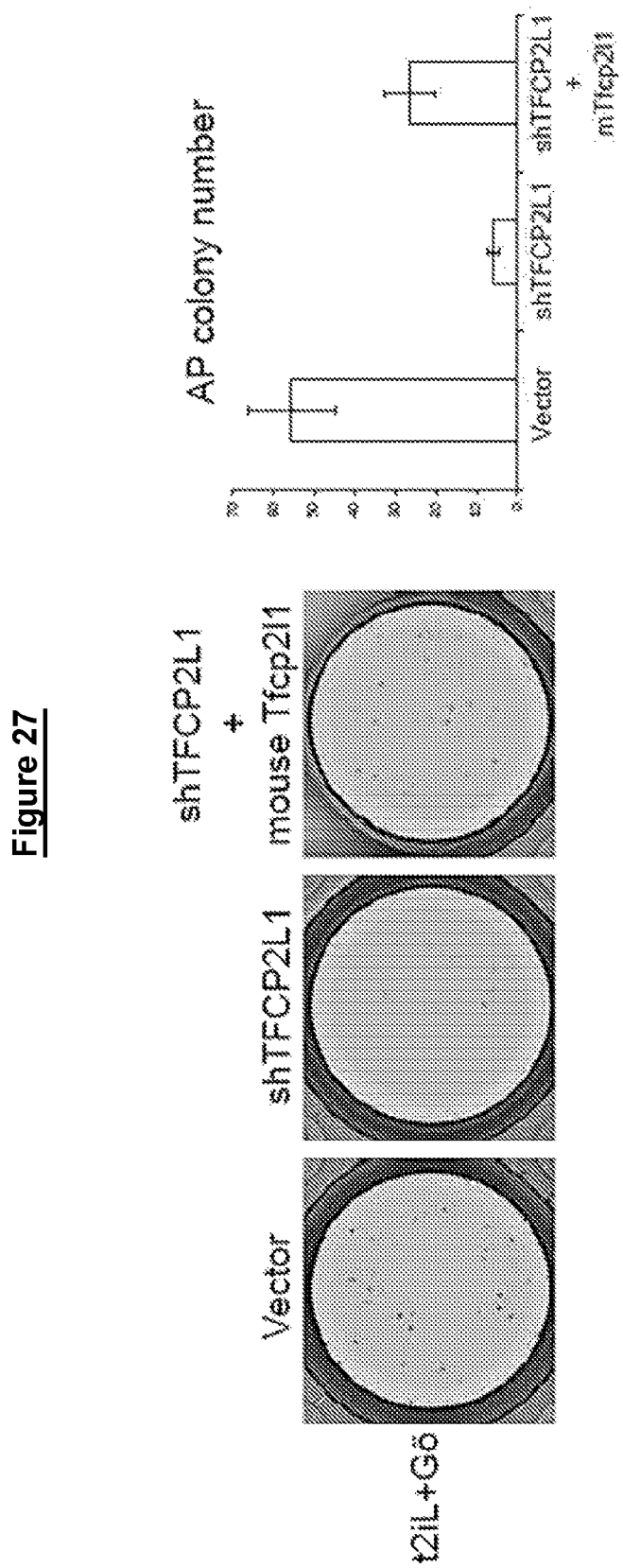

FIG. 27 Rescue of TFCP2L1 knockdown with mouse Tfcp2l1.

Colony formation by shTFCP2L1 knockdown cells transfected with mouse Tfcp2l1 expression vector. Knockdown cells maintained by DOX induction of NANOG and KLF2 were transfected with a piggyBac m Tfcp2l1 expression vector and transfectant pools established by selection in hygromycin. Cells were then plated at 2000 cells/well in 24 well plates in t2iL+Gö without DOX and stained for alkaline phosphatase after 7 days.

Figure 28:
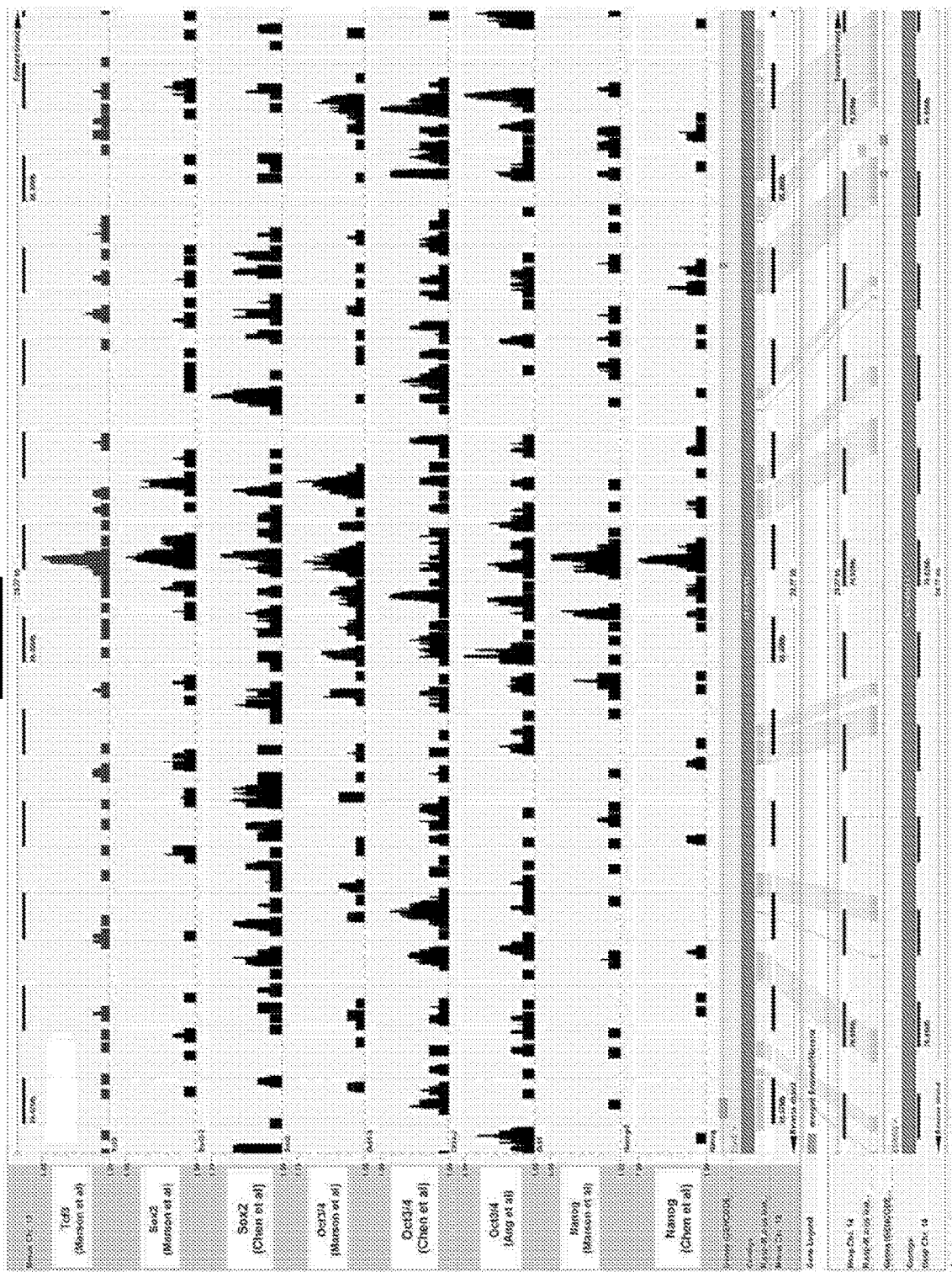

FIG. 28 Mouse Esrrb locus showing Nanog, Oct4, Sox2, and Tcf3 binding sites determined by ChIP-seq with homologous sequences to the equivalent human locus marked.

Signal tracks for ChIP-seq data from Marson et al (Marson et al., 2008), Chen et al (Chen et al., 2008), and Ang et al (Ang et al., 2011) were obtained from the latest version of the ES cell ChIP-seq compendium. (Martello et al., 2012b) (http://lila.results.cscr.cam.ac.uk/ES_Cell_ChIP-seq_compendium_UPDATED.html).

Figure 29:
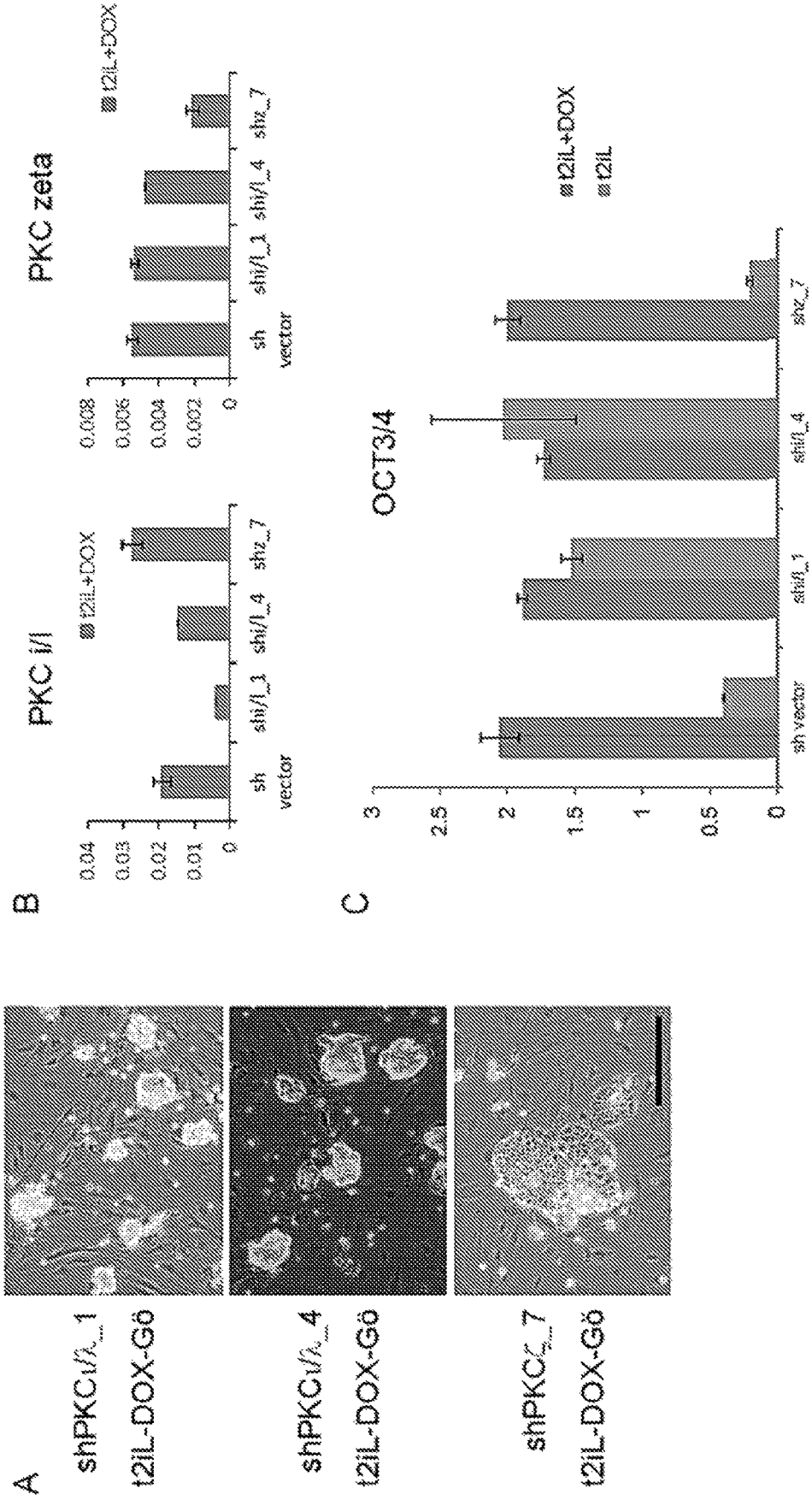

FIG. 29 Knockdown of aPKC iota/lambda and zeta.

Two different shRNA vectors, shPKC iota_1 and shPKC iota_4, were used for knockdown of PKC iota/lambda. shPKCzeta_8 was used for knockdown of PKC zeta. Scale bar is 100 μM.

A. Brightfield images of shPKC iota KD and shPKC zeta KD cells cultured in t2iL. shPKC iota KD cell retain undifferentiated morphology whereas shPKC zeta cells progressively differentiate.

B. knockdown efficiency of each shRNA.

C. OCT3/4 expression at passage 10 (KD lines) or 3 (control).

Figure 30:
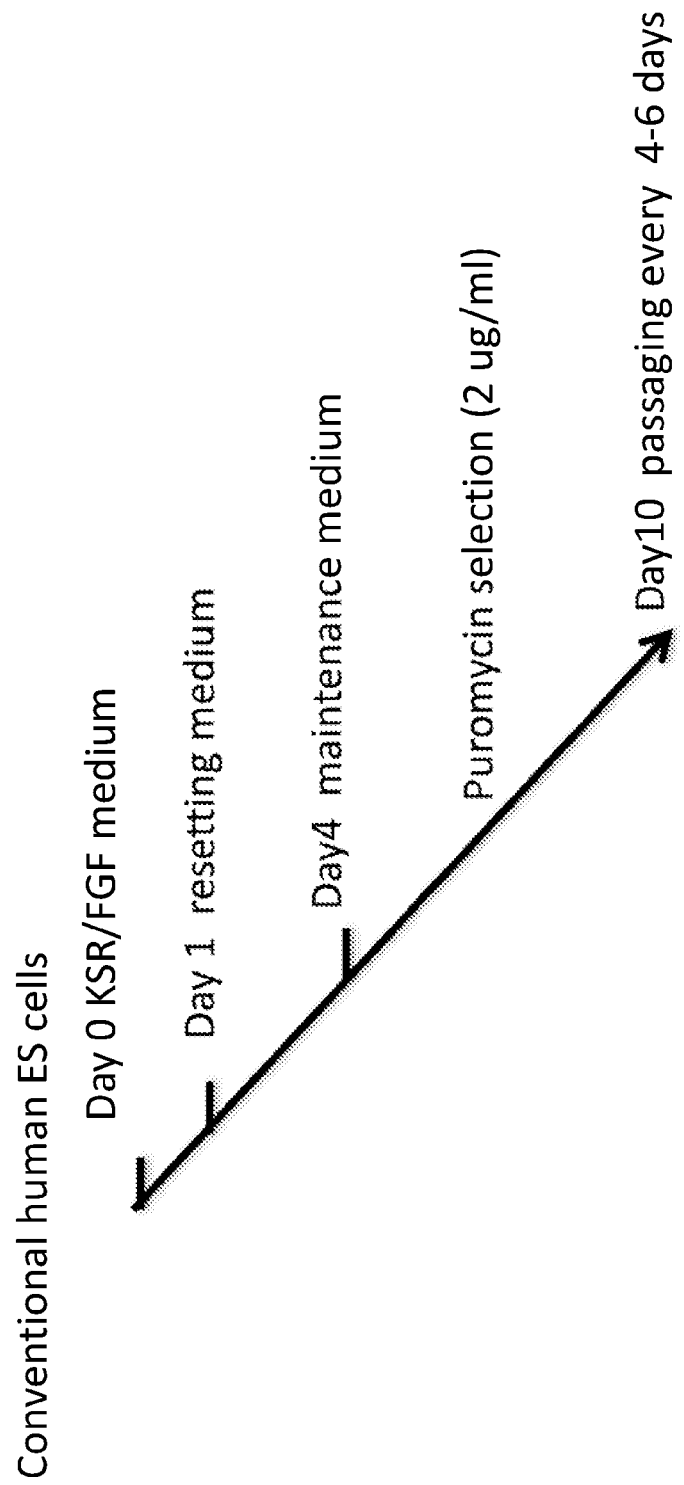

FIG. 30 Time line of resetting human ground state without transgene

Figure 31:
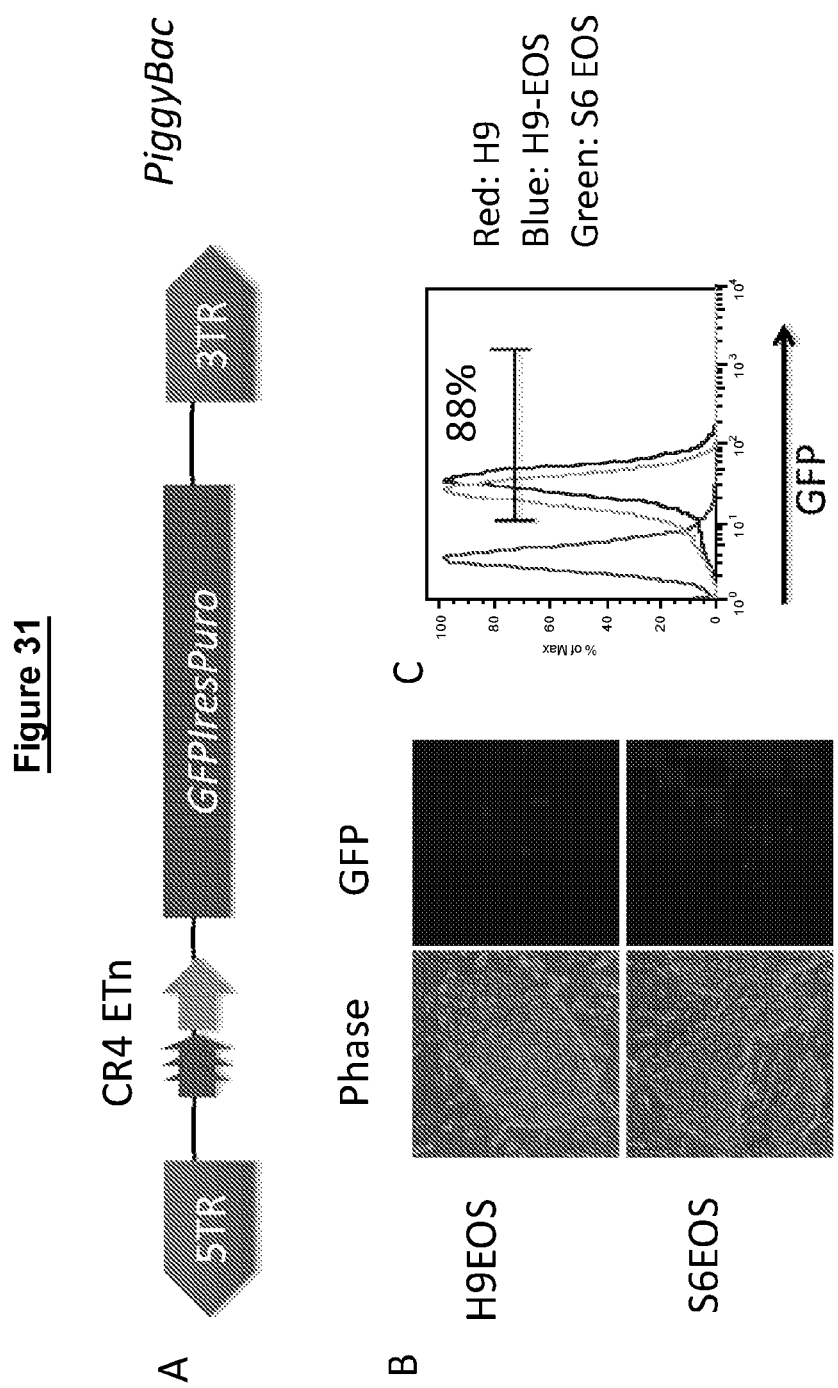

FIG. 31 Conventional human ES cells with PB-EOS reporter

A. Structure of PB-EOS reporter

Red (stacked) Arrows: Trimer of Oct4 regulatory element CR4; Etn: LTR of Early Transposon B. Images showing conventional human ES cells with EOS reporter. H9EOS, H9 cells with EOS reporter; 56EOS, Shef6 cells with EOS reporter. Note: GFP expression in most cells are not detectable under fluorescence microscope.

C. FACS analysis showing expression of GFP in more than more than 80% cells. Red: far left peak; green: pale middle peak; blue dark right peak.

Figure 32:
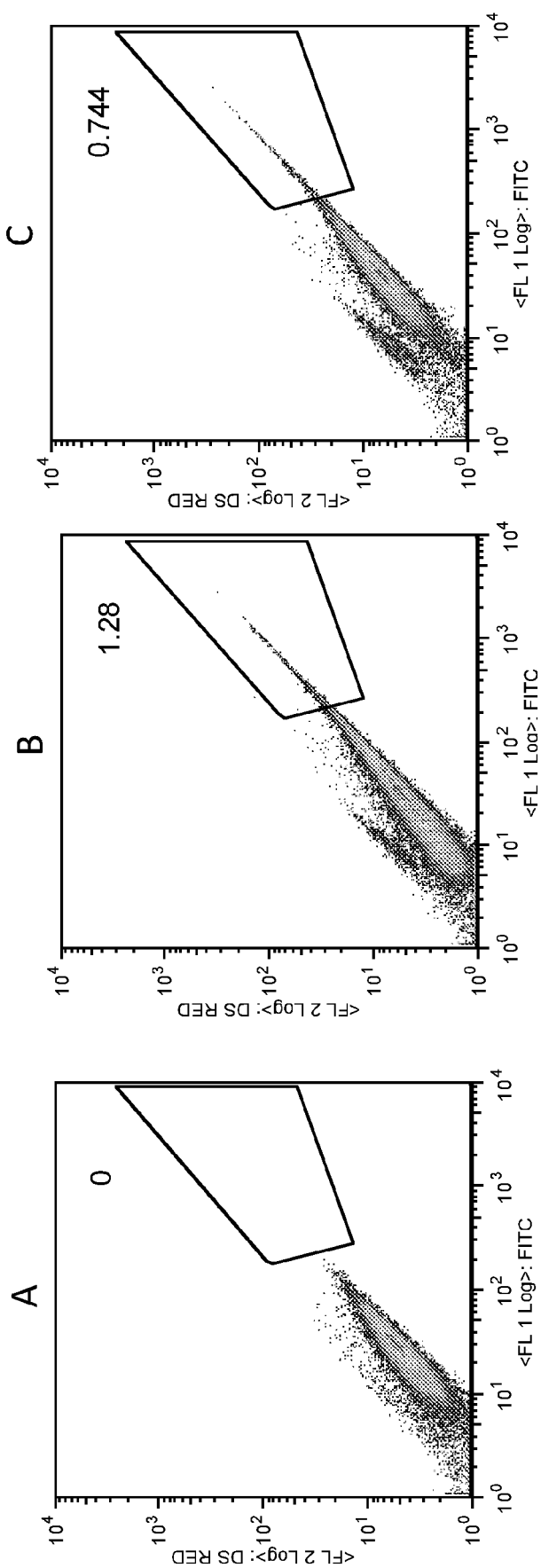

FIG. 32 FACS analysis of expression after 7 days in resetting

A: PDXL without HDAX inhibitor Vaproic acid (VPC) treatment

B: PDXL with VPC treatment from Day2 to Day3

C: PDXL with VPC treatment from Day3 to Day5

Figure 33:
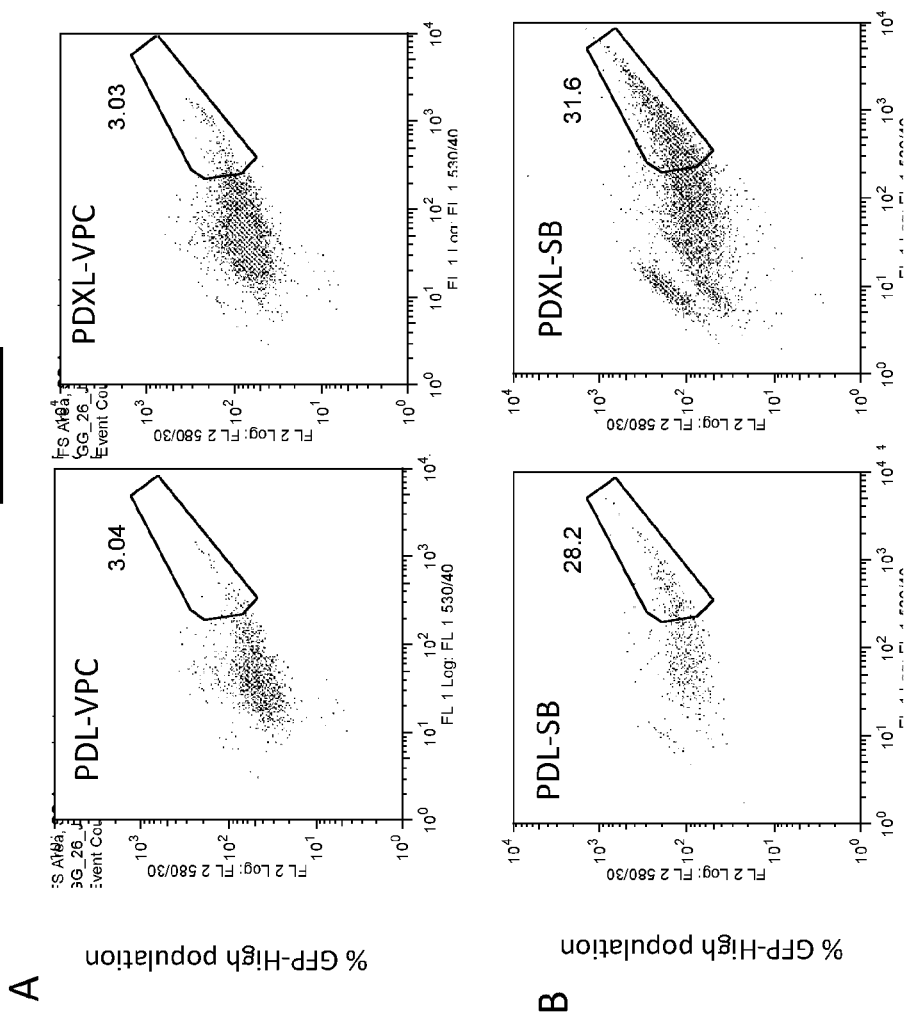

FIG. 33 FACS analysis of GFP expression 7 days after resetting

A. Three days VPC treatment increase resetting efficiency from around 1% to 3% (compare to FIG. 3)

B. An alternative HDAC inhibitor Sodium butyrate (SB) is also a potent resetting inducer.

Figure 34:
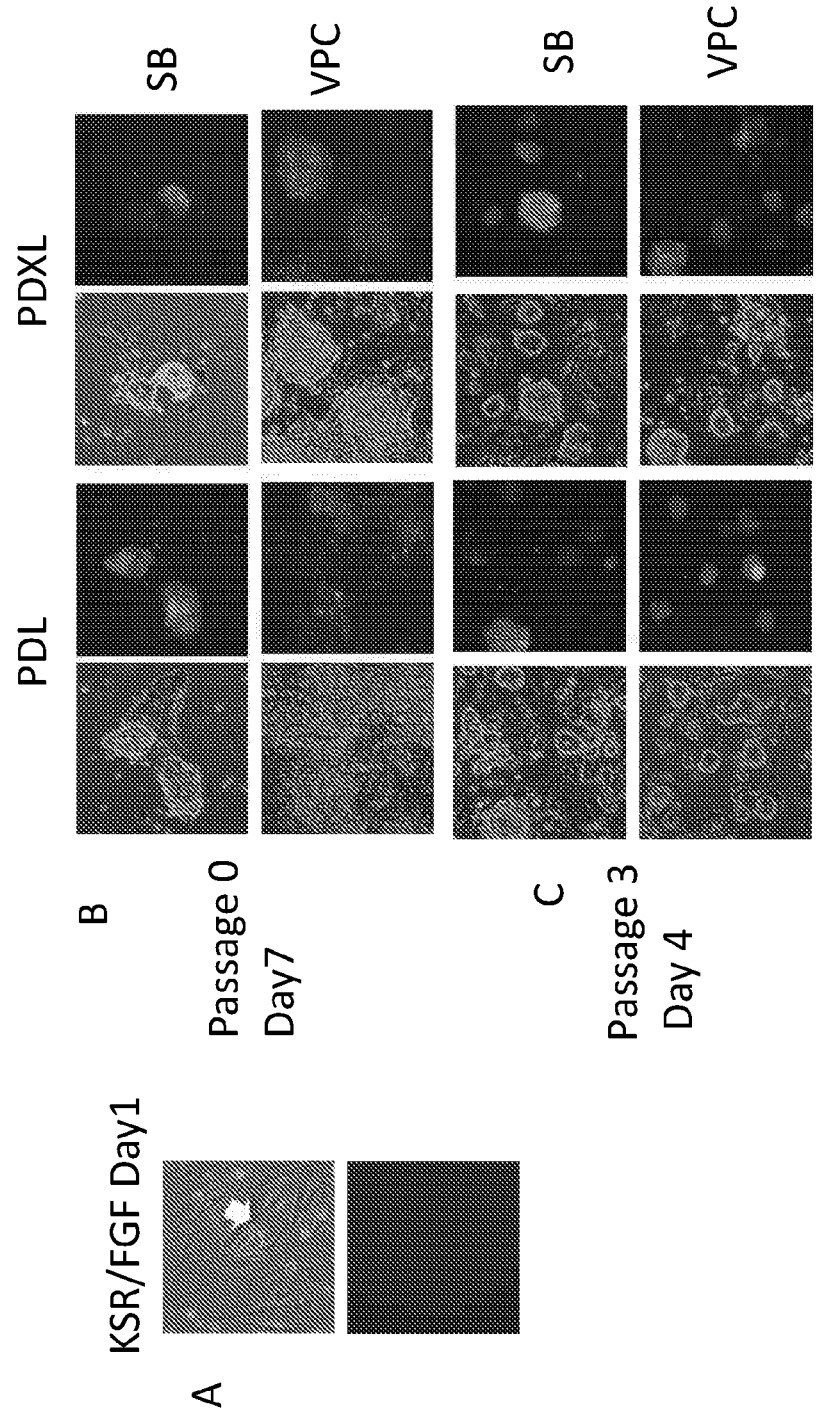

FIG. 34 GFP positive colonies after resetting

A. White arrow indicates GFP negative conventional ES cells one day after plating B. GFP positive colonies after 7 days in resetting medium C. GFP positive colonies after three passages. Puromycin selection was applied for 6 days at passage 1

Figure 35:
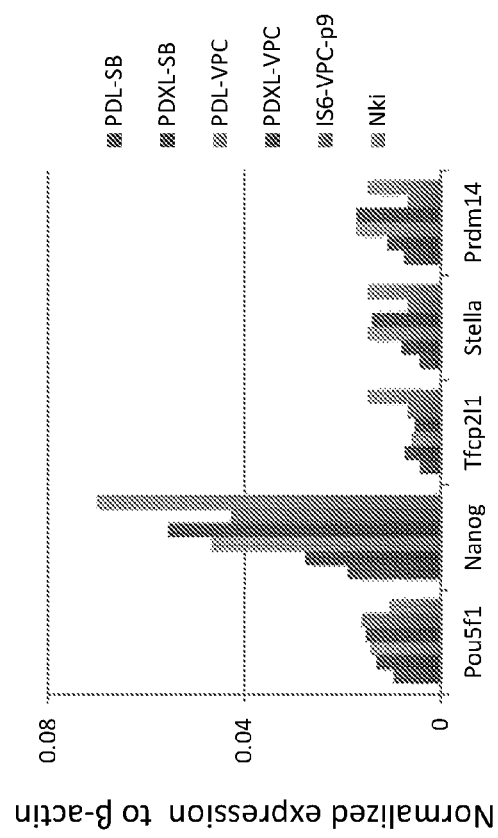

FIG. 35 Quantitative RT-PCR analysis of Naïve pluripotency markers

PDL-SB, PDXL-SB, PDL-VPC, PDXL-VPC represent the resetting medium the cells are from. Cells for PCR are FACS sorted GFP high population 7 days after resetting. 156-VPC-P9: Naïve cells converted with PDXL-VPC medium and maintained for 9 passages in T2i1Go+Y.

Nki: Naïve cells converted using inducible Klf2 and Nanog transgene.

FIG. 36

A. Image shows the morphology of EB after 7 days culture

B. Quantitative RT-PCR shows the expression of differentiation markers in EB compared to the conventional human ES cells FIG. 37 Reset FiPS to ground state A. Images show human iPS cells, FiPs-2b, form compact colonies after resetting. The reset medium contains either PD03, LIF (PDL), PDL with XAV939 or PDL with Go6983. VPC is added in all three conditions for 3 days.

B Higher magnification images showing the colony morphology of reset cells

Figure 38:
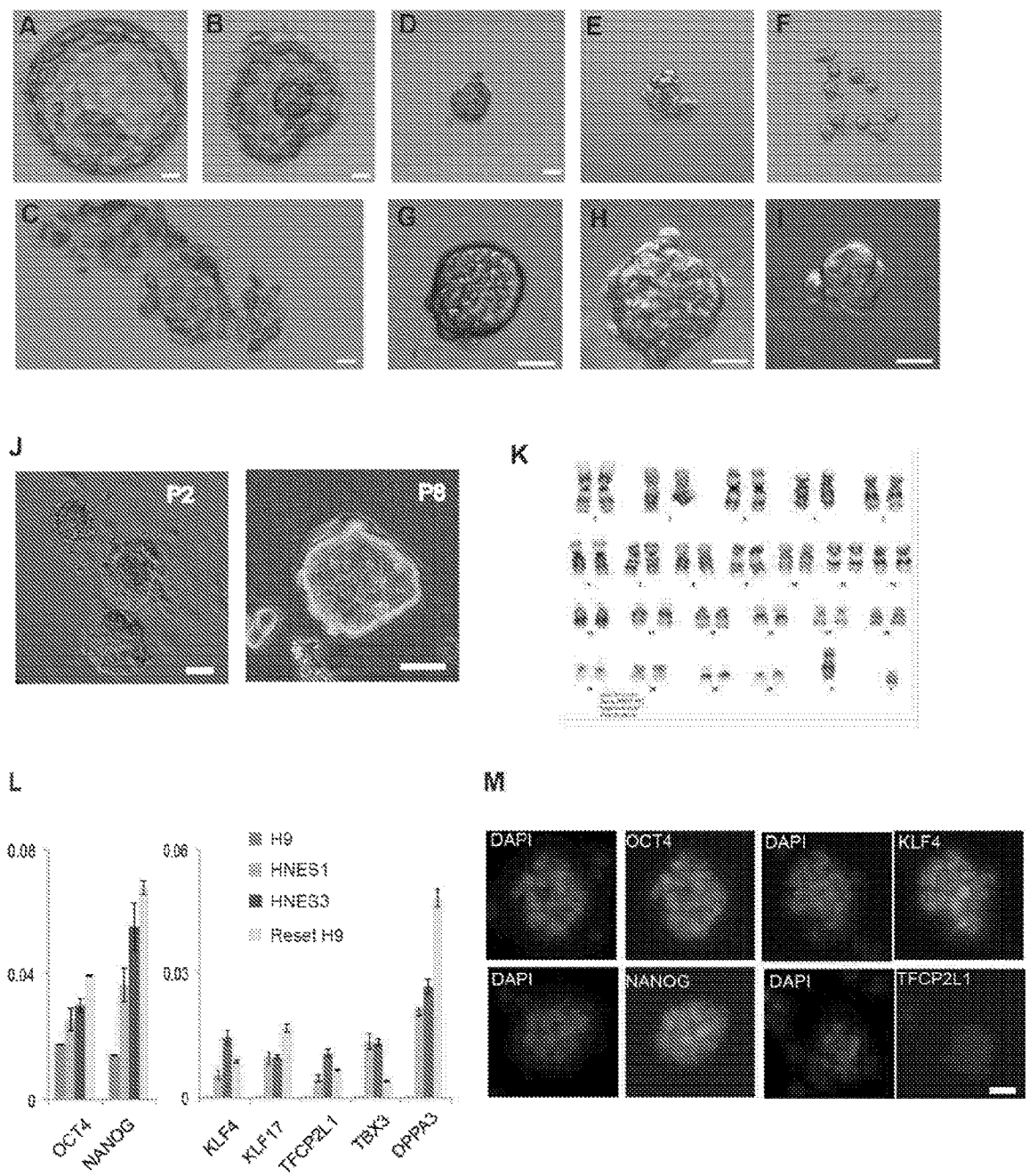

FIG. 38 Cell line derivation from dissociated human inner cell mass cells (A) Day 6 Blastocyst (B) Trophoblast lysis (C) Discarded trophoblast (D) Isolated inner cell mass (E&F) Dissociated ICM. (G-I) primary stem cells clones grown from individual dissociated ICM cells. (J) Colonies at Passage 2 and Passage 8. (K) G-banded metaphase analysis of HNES1 at passage 21. (L) Quantitative (q) RT-PCR analysis of naïve marker expression in HNES cells, conventional human PSC (H9) and in vitro reset PSC (reset H9).

Error bar indicates standard deviation (s.d.) of two PCR reactions. (M) Immunofluorescence staining of pluripotency markers in HNES1 cells. Scale bar represents 50 µm in A-C and 25 µm in G-M.

FIG. 39 Differentiation; (A) Colonies of naïve HNES1 cells in t2iLGöY and primed HNES1 cells after 12 passages in KSR/FGF. (B) qRT-PCR analysis of naïve marker expression in naïve HNES1 cells and derivatives after 3 passages in KSR/FGF. (C) qRT-PCR analysis of embryoid bodies formed from HNES1 and HNES1-primed cells. Error bars indicate s.d. of two PCR reactions. (D) Immunofluorescence staining of embryoid body outgrowths: TuJ1, beta-III Tubulin; AFP, alpha foetoprotein and SMA, alpha smooth muscle actin (green); FOXA2 (red). Nuclei are stained with DAPI in blue. Scale bar, 100 µm.

Figure 40:
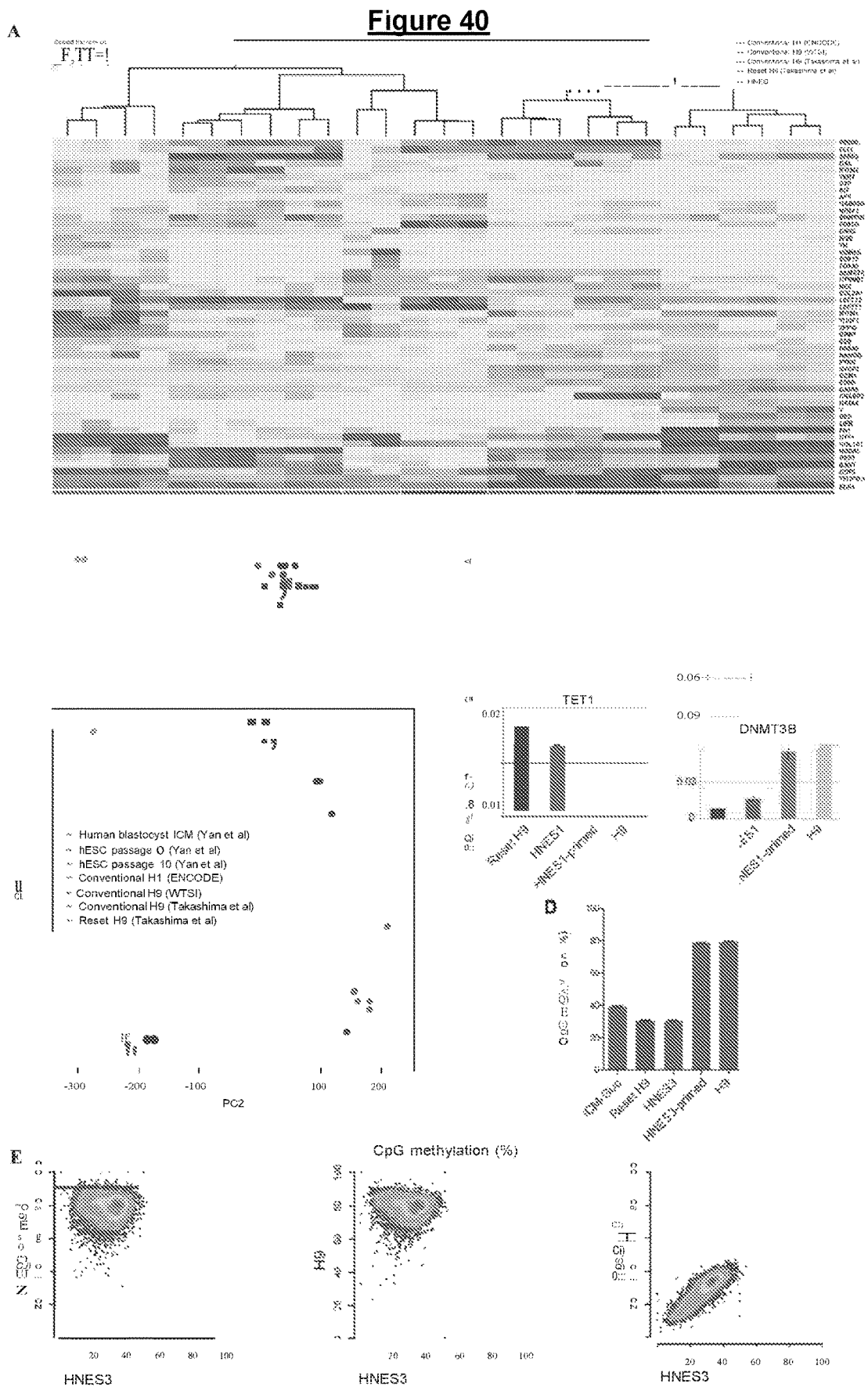

FIG. 40 Transcriptome and methylome analyses (A) Clustered expression data from HNES, reset and conventional hPSC for a panel of pluripotency and lineage markers selected by the International Stem Cell Initiative.

Displayed are $\log_2$ FPKM values scaled by the mean expression of each gene across samples. Published data are labelled with ENA accession codes. (B) Principal component analysis of HNES, reset and conventional hPSC along with single cell RNA-seq data for early human ICM and PSC explants (Yan et al., 2013). (C) qRT-PCR analysis showing increased TET1 and reduced expression of DNMT3B in HNES cells. Error bar indicates s.d. of two reactions. (D) Proportion of whole genome CpG methylation by bisulfite sequencing (BS-seq) analysis. ICM-Guo is extracted from Guo et al., 2014. (E) Scatter plots comparing global methylation by averaging 500 kb window methylation levels of CpGs in HNES cells with primed derivatives, reset H9 and conventional H9 cells.

Figure 41:
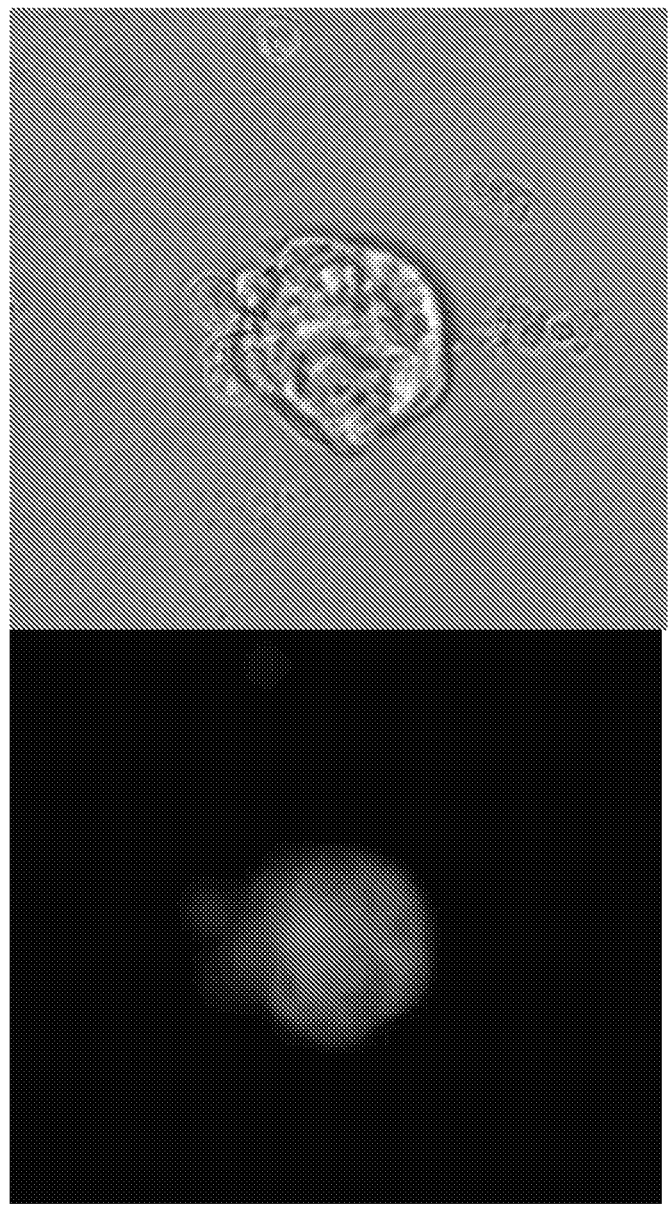

FIG. 41 Bright field and fluorescence images of reset iH9-EOS cells after culture for 25 days (7 passages) in t2iL with Ro-31-8425 (0.1 µM) replacing Gö6983.

EXAMPLES

Example 1

Experimental Procedures
Cell Culture

Human embryo derived cells, HI, H9 (WiCell Research Institute) (Thomson et al., 1998) and Shef6 (Aflatoonian et al., 2010) and human iPS cells generated from adult keratinocytes (Invitrogen), fibroblasts (Invitrogen), or adipose-derived stem cells (Invitrogen) were cultured on mouse embryonic fibroblast (MEF) cells. Conventional PSC cell medium (FGF/KSR) comprised DMEM/F12 (Sigma-Aldrich) with 10 ng/ml bFGF (prepared in-house) and 20% KSR (Invitrogen) supplemented with 100 mM 2-mercaptoethanol (Sigma-Aldrich, cat. M7522), MEM nonessential amino acids (Invitrogen, cat. 11140050), 2 mM L-glutamine (Invitrogen, cat. 25030024). Conventional PSC were passaged every five to seven days as small clumps by dissociation with 0.025% Trypsin, 1 mg/ml Collagenase IV (Invitrogen 17104-019), KSR (final 20%), 1 mM $CaCl_2$. Throughout this study cells were maintained in incubators at 5% oxygen.

piggyBac vectors (2 µg) carrying doxycycline-inducible KLF2 or NANOG coupled to Venus were co-transfected together with an rtTA expression construct (2 µg) and pBase helper plasmid (4 µg) into dissociated cells in the presence of ROCK inhibitor (Y-27632, Calbiochem) using the Neon Transfection System (Program 14; Invitrogen). Two days later, G418 was applied (100 µg/ml). After selection for two weeks, Venus negative cells were isolated by flow cytometry to purify from cells with leaky transgene expression.

To induce resetting, transfected PSC were dissociated with trypsin and replated as single cells in the presence of ROCK inhibitor. Doxycycline (DOX, 1 µM) was added the next day and 24 h later medium was changed to N2B27 medium (Ndiff227, StemCells Inc., SCS-SF-NB-02) with 1 µM PD0325901 (PD03), human LIF (prepared in-house), DOX and either 3 µM CHIR99021 (2iL+DOX) or 1 µM CHIR99021 (t2iL+DOX). Medium was changed every day. Cells were split every five to seven days after dissociation to single cells with Accutase (Life Technologies) for 10 minutes. Around two weeks after DOX induction, cells were transferred to t2iL+5 µM PKC inhibitor Gö6983 (Sigma-Aldrich) (t2iL+Gö). Reset cells cultured in t2iL+Gö were also passaged every five to seven days as single cells. Cells transferred to t2iL+Gö proliferate slowly for the initial couple of passages after withdrawal of DOX. Cells were maintained on MEF feeders throughout.

For transient expression and resetting we first generated H9 and Shef6 cells with an EOS-GFP/puro$^R$ reporter (Hotta et al., 2009) introduced in a piggyBac vector. We have observed that in the PB rather than lentiviral vector context this reporter is initially expressed heterogeneously in conventional PSC and progressively silenced, but is re-expressed during resetting. We used NANOG and KLF2 expression constructs driven by the CAG promoter harbouring a blasticidin resistance gene. One well of a 6-well plate was transfected as above with 3 µg of non-linearised NANOG and KLF2 plasmids. Two days later, medium was switched to N2B27 with PD173074 (PD17, 0.5 µM), PD03 (0.5 µM) and hLIF. At day 4, cells were retransfected and on day 8 medium was changed to t2iL+Gö. Puromycin selection (0.5 µg/ml) was applied from day 12 onwards for two passages. Single colonies were picked on passage 4 or 5. Primers for genomic PCR to detect the CAG promoter are in Table S5 and TaqMan Copy Number Assays against the blasticidin resistance gene were performed as described in the manufacturer's protocol using RNase P and TERT as independent copy number reference Assays.

TABLE S5

TaqMan and UPL probes used for qPCR assays Taqman

| Gene | Taqman probe |
| --- | --- |
| NANOG | Hs02387400_g1 |
| KLF2 | Hs00360439_g1 |
| OCT3/4 | Hs03005111_g1 |
| TBX3 | Hs00195612_m1 |
| REX1 | Hs00399279_m1 |
| TFCP2L1 | Hs00232708_m1 |
| KLF4 | Hs00358836_m1 |
| GBX2 | Hs00230965_m1 |
| SALL4 | Hs00360675_m1 |
| ESRRB | Hs01584024_m1 |

TABLE S5-continued

TaqMan and UPL probes used for qPCR assays Taqman

| Gene | Taqman probe |
|---|---|
| SOX17 | Hs00751752_s1 |
| CXCR4 | Hs00607978_s1* |
| FOXA2 | Hs00232764_m1 |
| T | Hs00610080_m1 |
| PDGFRA | Hs00998018_m1 |
| PDGFRB | Hs01019589_m1 |
| SOX1 | Hs01057642_s1 |
| PAX6 | Hs01088112_m1 |
| MAP2 | Hs00159041_m1 |
| NKX2-2 | Hs00159616_m1 |
| TNNT2 | Hs00165960_m1 |
| MYOCD | Hs00538071_m1 |
| PRKCZ | Hs00177051_m1 |
| PRKCI | Hs00995854_g1 |
| hCMVlNANOG | Custom TaqMan Assays* |
| hCMV1KLF2 | Custom TaqMan Assays* |
| KLF2 endo | Custom TaqMan Assays* |
| NANOG endo | Custom TaqMan Assays* |

Custom TaqMan Assays*: Probes were made by Custom Taqman Assays. Endo probes detect UTR region of NANOG and KLF2. Transgene specific probes were made on the junction of Dox-inducible vector and genes.

| | | UPL | |
|---|---|---|---|
| Gene | Primer | sequence | UPL probe |
| STELLA | U_STELLA R | tggtagcaatttgaggctctg | #80 |
|  | U_STELLA L | atcggcgtcttgacacaac |  |
| ISL1 | U_ISL1 L | aaggacaagaagcgaagcat | #66 |
|  | U_ILS_1 R | ttcctgtcatcccctggata |  |

| genomic PCR | |
|---|---|
| CAG R | ATTACCATGGGTCGAGGTGA |
| CAG L | AGAAAAGAAACGAGCCGTCA |

| Copy Number Assay (Taqman) | |
|---|---|
| BsdR | Mr00733720_cn |
| Reference Assay, hRNase P | 4403326 |
| Reference Assay, hTERT | 4403316 | differentiation media: GMEM with L-glutamine, pyruvate, 2ME and 10% serum; or N2B27 with 10% KSR. Medium was changed every other day. RNA was prepared at day0, day5 and day10. For endoderm differentiation, reset cells were seeded on Matrigel (growth factor reduced, BD, 356230) coated plates in mTeSR medium for one week and then transferred into RPMI with 100 ng/ml Activin A (prepared in-house) and 25 ng/ml mWnt3A (R&D Systems) (Kroon et al., 2008). The following day medium was changed to RPMI with 100 ng Activin A and 0.2% serum. Flow cytometry for CXCR4 and E-cadherin was performed at day 3 and immunofluorescence for SOX17 and FOXA2 was performed at day 4. For cardiomyocyte differentiation, reset cells were cultured in FGF/KSR medium for 6 days or more on MEF feeder cells. 10,000 cells were plated per V bottom well in MEF-conditioned FGF/KSR medium containing 10 µM ROCKi. At day 3 medium was changed to DMEM/F12 with 20% FBS, L-Glutamine, MEM-AA, 2ME, and 50 µg/ml Ascorbic acid (Moretti et al., 2010). At day 7, aggregates were seeded on gelatin-coated wells. Differentiation medium was changed every two days. Beating foci appeared from 21 days. For neural induction, reset cells were first cultured in FGF/KSR for a minimum of 6 days.

Colony forming assays were carried out on MEF feeder cells by plating 1000 cells per well in 24-well plates, 2000 cells for 12-well plates and 5000 cells for 6-well plates. ROCKi was used for conventional but not reset cells. Activin/TGF β receptor inhibitor A83-01 was used at 0.25 µM where indicated. Plates were fixed and stained for alkaline phosphatase (Sigma-Aldrich, cat. 86R-1KT). Plates were scanned using a CellCelector (Aviso) or cellSens Dimension (Olympus).

For feeder-free culture plates were coated overnight at 4° C. with either diluted BD Matrigel hES-qualified Matrix (1:30) or Laminin 511-E8 (iMatrix-511; Nippi) at 0.5 mg/cm$^2$ (Nakagawa et al., 2014). Cells were dissociated in the presence of ROCKi and plated in t2iL with Gö reduced to 2 µM.

Differentiation

For embryoid body formation, 10,000 reset cells dissociated with Accutase were plated per well of a PrimeSurface 96V cell plate (Sumitomo Bakelite, MS-9096V) in two Dissociated cells were then seeded on Matrigel (growth factor reduced, BD 356230) coated plates in mTeSR for two days before medium was changed to Ndiff227 (StemCells Inc.) with 10 ng/ml FGF, 20 µM SB431542 and 260 ng/ml Noggin (R&D) (Chambers et al., 2009). At day 5, medium was changed to Ndiff227 with 10 ng/ml FGF, 20 µM SB431542. At day 10, cells were fixed and stained for TUJ1 and NEUN.

Teratoma Formation

Studies were carried out in a designated facility under licenses granted by the UK Home Office. Approximately 10$^5$ cells were injected under renal capsules of NOD/SCID mice. After 12 weeks teratomas were excised, fixed with 4% PFA, sectioned and stained with haematoxylin and eosin.

Marker Analysis by qRT-PCR

Total RNA was isolated using the RNeasy Kit (QIAGEN) and complementary DNA (cDNA) made from 1000 ng of RNA using SuperScriptIII (Invitrogen) and oligo-dT primers. For real-time PCR, we used TaqMan Fast Universal Master Mix and TaqMan probes (Applied Biosystems) or the Universal Probe Library (UPL, Roche) system. Primers and UPL probe numbers are detailed in Table S5. Two or three technical replicates and at least two independent cultures were assayed for all quantitative PCR reactions. An endogenous control (Human GAPD, Applied Biosystems 4352934E) was used to normalise expression.

Immunostaining

Cells were fixed in 4% paraformaldehyde for 10 minutes, and then blocked with 2% donkey serum/PBS+0.1% BSA+ 0.1% Triton (PBSBT) for 2 hours. Primary antibodies were diluted in PBSBT and incubated at 4° C. overnight. Details of antibodies are provided in Table S6. Secondary antibodies were diluted 1:1000 and incubated at room temperature for 1 hour. Nuclei were counterstained with DAPI. Staining of methylated DNA was performed as previously described (Ficz et al., 2013). Cells were fixed by 4% PFA for 10 minutes. After permeabilisation by PBS+0.5% Triton for 1 hour, fixed cells were incubated in 2N HCl for 30 minutes, washed and then and then blocked in PBSBT for 2 hours. Cells were incubated in 1:250 5mC (Eurogentec, BI-MECY) and 1:500 5hmC (Active Motif, 39769)/PBSBT. Nuclei were stained with DAPI. Human embryos donated from in vitro fertilisation programmes with informed consent were thawed and cultured to day 7 post fertilisation, fixed in 4% PFA and immunostained and imaged as described previously (Roode et al., 2012).

TABLE S6

Antibodies used for immunostaining, immunoblotting and flow cytometry Analysis

| Table S5 Antibody | Company | Cat NO | concentration |
|---|---|---|---|
| NANOG | Abcam | ab21624 | 1:200 |
| NANOG | eBioscience | 14-5769-82 | 1:200 |
| KLF4 | Santa Cruz | sc-20691 | 1:400 |
| TFCP2L1 | R and D | AF5726 | 1:500 |
| TFE3 | SIGMA | HPA023881-100 UL | 1:500 |
| STELLA | Millipore | MAB4388 | 1:200 |
| ECAD | BECKMAN COULTER | IM1763 | 1:100 |
| CXCR4 | BD Pharmingen | 555974 | 1:100 |
| SOX17 | R and D | AF1924 | 1:200 |
| FOXA2 | Abnova | H00003170 | 1:200 |
| TuJ1 | R and D | MAB1195 | 1:200 |
| NEUN | Millipore | MAB377 | 1:100 |
| 5-hmC | ACTIVE MOTIF | 39769 | 1:500 |
| 5-mC | Eurogentec | BI-MECY-0100 | 1:250 |
| H3K9me3 | active motif | 39765 | 1:500 |
| ERK1/2 | Cell Signaling | #9107 | 1:1000 |
| pERK1/2 | Cell Signaling | #4376 | 1:1000 |
| alpha Tublin | Abcam | ab7291 | 1:5000 |

Karyotype Analysis

KaryoMAX (Invitrogen, final concentration 0.06 μg/ml) was added to the culture medium. And cells incubated more around 6 hours at 37° C. Cells collected in a single cell suspension and washed by PBS were incubated in 5 ml of a pre-warmed (37° C.), 0.075M potassium chloride for 10 minutes (37° C.). After centrifugation, 4 ml fixative (3:1 methanol:acetic acid) was added. This fixation step was repeated twice. Fixed samples were analysed as G banded karyotypes at Medical Genetics Laboratories Cambridge University Hospitals NHS Foundation Trust.

Flow Cytometry

After treatment with Accutase or trypsin/EDTA, cells were blocked in donkey serum, on ice, for 20 minutes. Cells were stained on ice with E-cadherin antibody and CXCR4 antibody conjugated with PE in HBSS (Invitrogen) with 1% BSA for 20 minutes. After washing, secondary antibody, APC Rat Anti-Mouse IgG1 (BD Pharmingen, 550874) was applied. Flow cytometry analyses were performed using a Dako Cytomation CyAn ADP high-performance cytometer with Summit software.

Cell Metabolism

Oxygen consumption was measured using an $XF^e24$ Analyzer (SeaHorse Bioscience) according to the manufacturer's protocol. In brief, SeaHorse plates were pre-treated by coating with laminin and 80,000 cells were seeded on each well the night before the experiment. Culture media were exchanged for XF Base Medium (SeaHorse bioscience) supplemented with 2 mM pyruvate and 20 mM glucose with an adjusted pH of 7.4 and cells incubated at 37° C. in atmospheric $CO_2$ for one hour. Oligomycin (2 μM), FCCP (500 μM), Antimycin (1 μM) and Rotenone (1 μM) were injected during assay (XF cell mito stress test kit, Seahorse Bioscience). Mitochondria were stained with Mito Tracker Green FM (final concentration 50 nM, Life Technologies) or Tetramethylrhodamine, ethyl ester (TMRE, final concentration 20 nM, Life Technologies) in the relevant medium for 10 minutes and analysed by confocal microscopy.

Mass Spectrometry of Nucleosides

Genomic DNA was digested using DNA Degradase Plus (Zymo Research) according to the manufacturer's instructions and analyzed by liquid chromatography-tandem mass spectrometry on a LTQ Orbitrap Velos mass spectrometer (Thermo Scientific, Hemel Hempstead, UK) fitted with a nanoelectrospray ion-source (Proxeon, Odense, Denmark). Mass spectral data for C, 5mC and 5hmC were acquired in high resolution full scan mode (R>40,000 for the protonated pseudomolecular ions and >50,000 for the accompanying protonated base fragment ions), and also in selected reaction monitoring (SRM) mode. SRM data, monitoring the transitions 228→112.0505 (C), 242→126.0662 (5mC) and 258→142.0611 (5hmC), were generated by HCD fragmentation using a 10 mass unit parent ion isolation window, a relative collision energy of 20% and R>14,000 for the fragment ions. Peak areas for the fragment ions were obtained from extracted ion chromatograms of the relevant scans and quantified by external calibration relative to standards obtained by digestion of nucleotide triphosphates.

BS-Seq Library Preparation and Analysis

Genomic DNA was prepared using AllPrep DNA/RNA mini kit (QIAGEN), fragmented by sonication (Covaris) and adaptor ligated using Illumina supplied methylated adaptors and NEBnext library preparation kit. Subsequently DNA was bisulphite-treated using the Sigma Imprint kit according to the manufacturer's instructions (one step protocol). Final library amplification (11 cycles) was done using KAPA Uracil+ (KAPA Biosystems), after which the libraries were purified using Ampure beads (×1). Raw sequence reads were trimmed to remove both poor quality calls and adapters using Trim Galore (www.bioinformatics.babraham.ac.uk/projects/trim_galore/) (v0.2.2, default parameters). Remaining sequences were mapped to the human GRCh37 genome using Bismark (Krueger and Andrews, 2011) (v0.7.4, default parameters), and CpG methylation calls were extracted and analysed using SeqMonk (www.bioinformatics.babraham.ac.uk/projects/seqmonk/) and custom R scripts. Global methylation comparison was calculated by averaging 1 kb window methylation levels of CpGs covered by at least 30 reads.

RNA Processing

Total RNA was extracted with the TRIzol/chloroform method (Invitrogen), followed by resuspension in RNAsecure (Ambion), incubation with TURBO DNase (Ambion) at 37° C. for 1 h, further phenol/chloroform extraction and ethanol precipitation. RNA integrity was assessed with the RNA 6000 Nano assay on the 2100 Bioanalyzer (Agilent).

Transcriptome Sequencing

Ribosomal RNA was depleted from 5 µg of total RNA using Ribo-Zero capture probes (Epicentre). RNA samples were sheared by ultrasonication on a Covaris S2 for 80 s set at Duty Cycle 10, Cycles per Burst 200 and Intensity 4. Fragmented RNA was reverse-transcribed with a combination of random hexamer and oligo-dT primers (New England Biolabs) by SuperScript III (Invitrogen) at 50° C. for 2 h in the presence of 6 µg/ml actinomycin D (Sigma) to inhibit second-strand products. Second-strand cDNA was synthesized by DNA Polymerase I in the presence of RNase H with dUTPs substituted for dTTPs at 16° C. for 2 h. Sequential end repair and 3'-adenylation of cDNA products was carried out with T4 DNA polymerase and T4 polynucleotide kinase (20° C.), and with exo⁻ Klenow fragment (65° C.) in the presence of dATPs (New England Biolabs). These were ligated to barcoded adapters (NEXTflex-96, Bioo Scientific) by T4 DNA ligase (New England Biolabs) at 20° C. for 30 min. Second-strand DNA was digested with uracil DNA glycosylase (UDG) and Endonuclease VIII at 37° C. for 30 min. PCR amplification of first-strand library constructs was carried out with KAPA HiFi DNA polymerase (Kapa Biosystems) for 13 cycles. Purification of reaction products at each step was performed with Ampure XP paramagnetic beads (Beckman Coulter). Library size distribution and molarity was assessed by the DNA 1000 assay on the 2100 Bioanalyzer (Agilent). Sequencing was performed on the Illumina HiSeq 2000 in 100 bp paired-end format.

RNA-Seq Data Analysis

Sequencing reads were aligned to the human genome build hg19/GRCh37 with the STAR spliced aligner (Dobin et al., 2013). Transcript quantification was performed using htseq-count, part of the HTSeq package (Anders et al., 2014), based on GENCODE v15 (Harrow et al., 2012) (Ensembl release 70) (Flicek et al., 2014)) human gene annotation. Sequencing reads from published RNA-seq experiments were obtained from the European Nucleotide Archive (ENA). To ensure maximal compatibility between datasets, raw counts were generated in the manner described above, and all RNA-seq samples were processed together. The mouse and human samples were related via one-to-one orthologous genes annotated in Ensembl v70. Libraries were corrected for total read count using the size factors computed by the Bioconductor package DESeq (Anders and Huber, 2010), and normalised for gene length to yield FPKM values. To generate expression heatmaps, FPKM values were scaled relative to the mean expression of the gene across all samples. Heatmaps include genes for which a difference in expression was observed are displayed (i.e. scaled expression >1 or <−1 in at least one sample). Principal components were computed by singular value decomposition with the princomp function in the R stats package, using expression levels that were normalised relative to the human embryo-derived PSC samples in each study.

Microarray Processing

Total RNA was processed for microarray analysis using the Ambion WT Expression Kit. Briefly, double-stranded cDNA was synthesized from 500 ng of RNA with random hexamers tagged with a T7 primer. Products were subjected to in vitro transcription by T7 RNA polymerase to generate antisense cRNA. Samples were reverse-transcribed by SuperScript III (Invitrogen) in the presence of dUTPs to yield single-stranded DNA. The template cRNA was then degraded by RNase H and cDNA products were fragmented by uracil DNA glycosylase (UDG) and apurinic/apyrimidinic endonuclease 1 (APE 1) (Ambion). Fragmented cDNA was then biotin-labelled by terminal deoxynucleotidyl transferase (TdT). Affymetrix Human Gene Array 1.0 ST arrays were hybridised for 16 h at 45° C., washed, stained with streptavidin-phycoerythrin (SAPE) conjugate on a FS450 automated fluidics station (Affymetrix), and imaged on a GCS3000 7G scanner (Affymetrix).

Microarray Data Analysis

Affymetrix Human Gene Array 1.0 ST arrays were processed with the oligo Bioconductor package (Carvalho and Irizarry, 2010) to summarize probeset transcript clusters. Microarray data from this study were normalized together with those from Gafni et al. (2013) using the Robust Multi-Array Average (RMA) method (Irizarry et al., 2003) applied through the oligo package. Principal components were calculated from the centred and scaled expression covariance matrix by singular value decomposition, computed by the prcomp function in the R stats package. Transcript clusters were associated with targeted genes based on GENCODE v15 human genome annotation (Ensembl release 70). Where multiple probesets for a given gene were present on the array, these were summarised using the maximal expression value. Expression data for heatmaps were scaled relative to the mean expression of each gene across all samples. Illumina sequencing and microarray processing were carried out by the EMBL Genomics Core Facility, Heidelberg.

Integrated Expression Analysis

RNA-seq data were cross-referenced with the microarray data, restricting the analysis to the genes interrogated by the array. To account for technical differences between studies and platforms, expression levels were computed relative to the human embryo-derived PSC samples from each study. These values were used as the basis for the global principal component analysis and the comparative analysis of marker genes.

RNAi Experiments siRNAs (QIAGEN, Table S7) were transfected at a final concentration of 40 nM using Dharmafect 1 (Dharmacon, cat. T-2001-01), following the manufacturer's protocol. For a 24-well plate (2 cm²), we used 1 µl of transfection reagent in 50 µl of Opti MEM (Invitrogen), 1 µl of 20 µM siRNA solution in 50 µl of OptiMEM, and 4000 conventional PSC in 0.4 ml of FGF/KSR medium or 2000 reset cells in 0.4 ml of t2iL+Gö. Medium was changed after overnight incubation. See Table S7 for siRNA details. shRNAs (Thermo Scientific, Table S8) were introduced using the Neon Transfection System (Invitrogen), program 14 for conventional PSC and Neon program 20 for reset cells with 2 µg of shRNA vector. Two days after electroporation, cells were selected in puromycin. For rescue experiments, shRNA knockdown cells were transfected using Neon program 14 with 1.5 µg of piggyBac vector carrying a Tfcp2l1, KLF4 or ESRRB expression cassette plus 1.5 µg of pBase and selected in hygromycin.

TABLE S7 siRNA sequences used for transient knockdown
experiments si RNA List (QIAGEN)

| Gene | No | siRNA | Cat No |
|---|---|---|---|
| GFP |  | GFP-22 siRNA | 1022064 |
| TFCP2L1 | 1 | Hs_TFCP2L1_5 | SI04206111 |
|  | 2 | Hs_TFCP2L1_3 | SI00743253 |
|  | 3 | Hs_TFCP2L1_7 | SI04312217 |
|  | 4 | Hs_TFCP2L1_6 | SI04230625 |
| REX1 | 1 | Hs_ZFP42_7 | SI04280241 |
|  | 2 | Hs_ZFP42_6 | SI04221385 |
|  | 3 | Hs_ZFP42_9 | SI04306974 |
|  | 4 | Hs_ZFP42_8 | SI04304440 |
| STELLA | 1 | Hs_DPPA3_1 | SI00373233 |
|  | 2 | Hs_DPPA3_3 | SI00373247 |
|  | 3 | Hs_DPPA3_8 | SI04177642 |
|  | 4 | Hs_DPPA3_7 | SI03204705 |
| KLF4 | 1 | Hs_KLF4_5 | SI03176733 |
|  | 2 | Hs_KLF4_6 | SI03649191 |
|  | 3 | Hs_KLF4_4 | SI00463253 |
|  | 4 | Hs_KLF4_7 | SI04144049 |

No 1 and 2 of were used for single siRNA kncok down based on the measurement of knock down efficiency by qPCR.

TABLE S8 shRNA sequences used for stable knockdown
experiments si RNA List (QIAGEN)

| Gene | No | siRNA | Cat No |
|---|---|---|---|
| GFP |  | GFP-22 siRNA | 1022064 |
| TFCP2L1 | 1 | Hs_TFCP2L1_5 | SI04206111 |
|  | 2 | Hs_TFCP2L1_3 | SI00743253 |
|  | 3 | Hs_TFCP2L1_7 | SI04312217 |
|  | 4 | Hs_TFCP2L1_6 | SI04230625 |
| REX1 | 1 | Hs_ZFP42_7 | SI04280241 |
|  | 2 | Hs_ZFP42_6 | SI04221385 |
|  | 3 | Hs_ZFP42_9 | SI04306974 |
|  | 4 | Hs_ZFP42_8 | SI04304440 |
| STELLA | 1 | Hs_DPPA3_1 | SI00373233 |
|  | 2 | Hs_DPPA3_3 | SI00373247 |
|  | 3 | Hs_DPPA3_8 | SI04177642 |
|  | 4 | Hs_DPPA3_7 | SI03204705 |
| KLF4 | 1 | Hs_KLF4_5 | SI03176733 |
|  | 2 | Hs_KLF4_6 | SI03649191 |
|  | 3 | Hs_KLF4_4 | SI00463253 |
|  | 4 | Hs_KLF4_7 | SI04144049 |

No 1 and 2 of were used for single siRNA kncok down based on the measurement of knock down efficiency by qPCR.

Results

NANOG and KLF2 Reset the Human PSC Phenotype

Transgenic expression of Nanog or Klf2 can convert mouse EpiSC to ground state ESC in the presence of 2i and LIF (2iL) (Hall et al., 2009; Silva et al., 2009). We tested the effect of expressing this pair of factors in human embryo-derived H9 cells. We introduced doxycycline (DOX)-inducible KLF2 and NANOG/Venus piggyBac constructs along with an rtTA vector into human embryo derived PCS. Transfectant pools were selected with G418 in conventional human PSC culture medium containing FGF and serum replacement (FGF/KSR) without DOX. Cultures were then dissociated and replated in the presence of Rho-associated kinase inhibitor (ROCKi) (Watanabe et al., 2007) prior to addition of DOX. We observed that DOX-induced cells differentiated or died if maintained in FGF/KSR. In contrast, when medium was changed to 2iL after exposure to DOX, undifferentiated cells persisted and formed multiple colonies that could readily be expanded by subsequent passaging. These colonies were strongly positive for Venus, indicating robust transgene expression, and displayed the tightly packed domed appearance typical of ground state mouse ESC (FIG. 1A). Cultures could be propagated continuously in 2iL plus DOX by enzymatic dissociation to single cells without using ROCKi. On withdrawal of DOX, however, cultures degenerated. DOX-withdrawn cultures could be rescued by transfer into KSR and FGF2 upon which the cells reverted to conventional flat PSC colony morphology and became sensitive to dissociation. Cells could be cycled between these two exclusive conditions by withdrawal and re-addition of DOX (FIG. 1A).

Figure 1B:
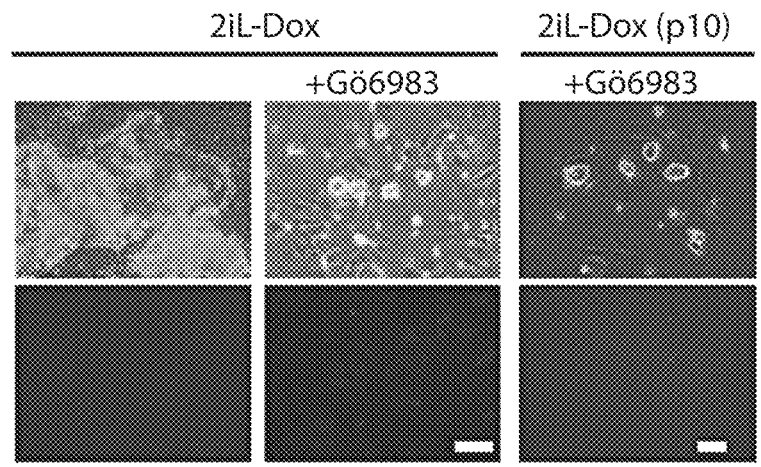

We investigated candidate pathways for the ability to support continued propagation in 2iL upon DOX withdrawal and found that addition of the protein kinase C (PKC) inhibitor Gö6983 (5 µM), which can suppress mouse ES cell differentiation (Dutta et al., 2011), allowed maintenance of compact refractile colonies without Venus expression (FIG. 1B). These cultures expressed OCT4 (FIG. 8) and expanded continuously, although proliferation was reduced and morphology less consistent compared to DOX-maintained cells. FIG. 41 shows that the PKC inhibitor Ro-31-8425 (0.1 µM) can be used as an alternative to Gö6983.

Figure 1C:
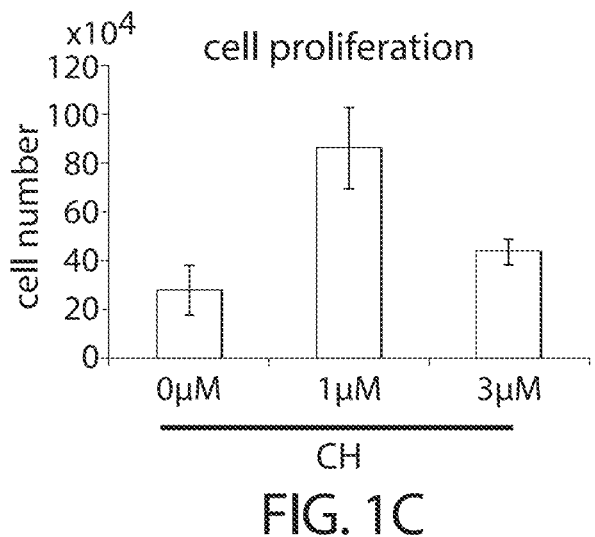

Moderating GSK3 inhibition improves self-renewal of rat ES cells (Chen et al., 2013a; Meek et al., 2013) and we have also observed that combination of Gö6983 with the GSK3 inhibitor CH is unfavourable for mouse ESC propagation (J. Wray and A S, unpublished). We therefore titrated CH. We observed that colony morphology improved in the complete absence of CH, but growth rate was reduced. An intermediate concentration of 1 µM restored growth rate while maintaining morphology (FIG. 1C). Henceforth cells were maintained in titrated 2i with LIF and Gö6983 (t2iL+Gö). Immunoblotting confirmed that Erk signalling was fully blocked in this condition (FIG. 9).

Figure 1D:
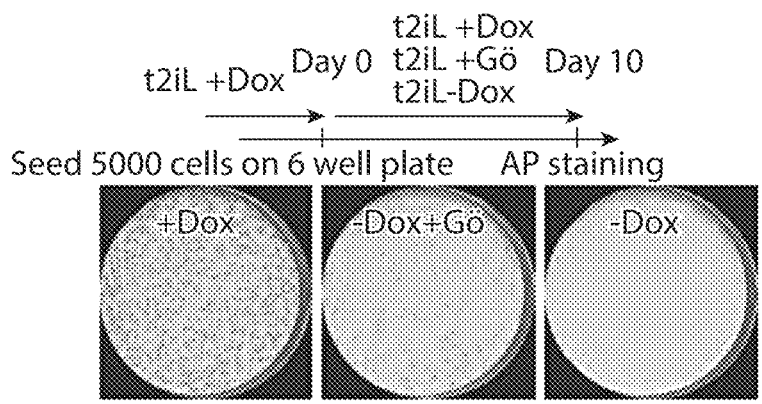
Figure 1E:
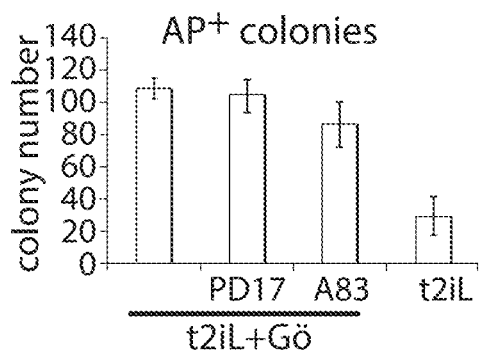

Alkaline phosphatase positive colonies formed from single cells in t2iL+Gö without ROCKi in absence of DOX, although numbers were fewer and size smaller than with DOX (FIG. 1D). Colony formation was not suppressed by inhibitors of TGF-β/activin or FGF receptors (FIG. 1E and FIG. 10).

Figure 1F:
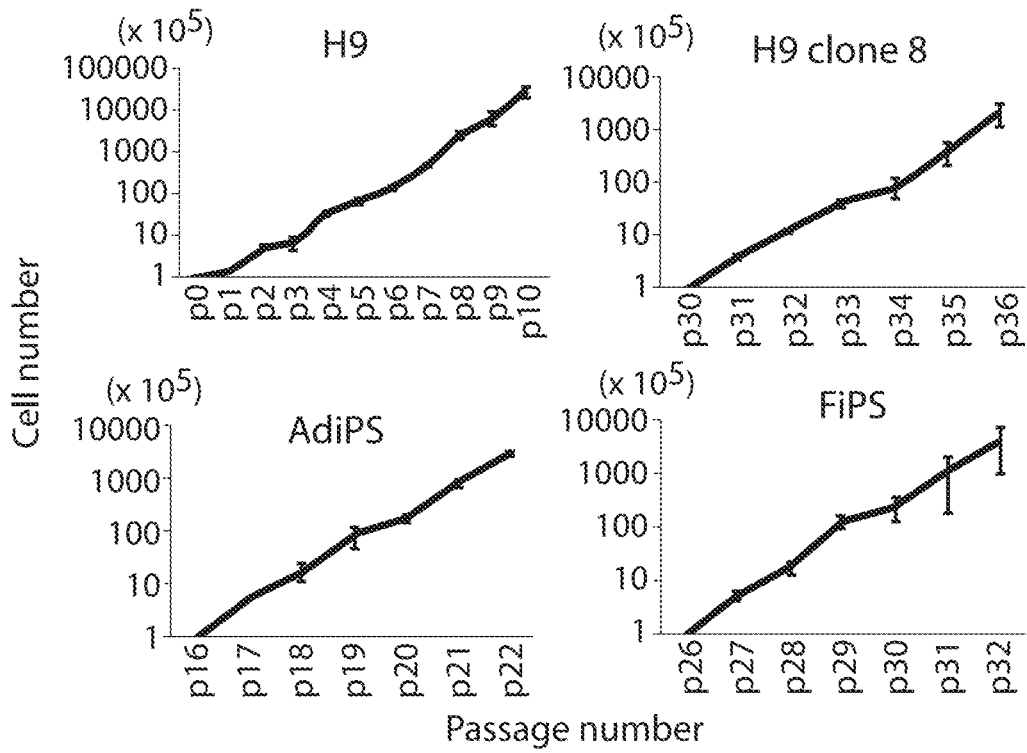
Figure 1G:
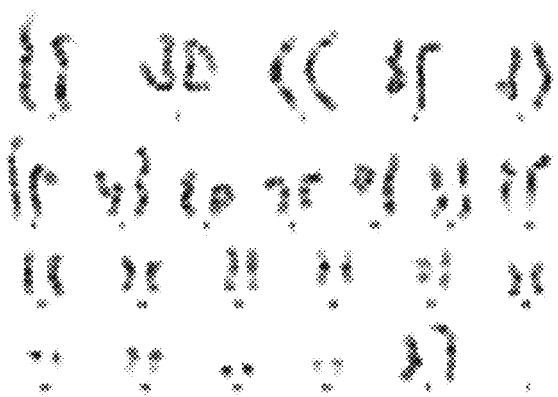

We repeated NANOG and KLF2 induced conversion more than 10 times using different embryo-derived and induced human PSC lines (Table 1) and in all cases obtained abundant tightly packed colonies in the presence of DOX. On DOX withdrawal and switch to t2iL+Gö the phenotype was generally maintained, although cultures initially exhibited some heterogeneity. Cultures stabilised after 2-4 passages and thereafter were readily maintained over multiple passages by enzymatic dissociation every 4 to 6 days and replating at a split ratio of 1:3 to 1:5. Independent cultures were continuously expanded over more than 20 passages (4 months) with no deterioration in morphology or doubling time (FIG. 1F and Table 1). Selective pressure for genetic deviation is a critical consideration in PSC propagation. We therefore analysed metaphase spreads at regular intervals. Diploid populations could be maintained over multiple passages (FIG. 1G), although occasional cultures showed trisomies, as frequently observed with conventional PSC (Amps et al., 2011), and were discarded.

TABLE 1a

|  | ES/iPS cells | Origin | Cumulative passages in t2iL + Gö | Chromosome count (Passage No) |
|---|---|---|---|---|
| H9 | ES | WiCell Research Institute | 37 | 46 XX (P15) |

TABLE 1a-continued

| ES/iPS cells | | Origin | Cumulative passages in t2iL + Gö | Chromosome count (Passage No) |
|---|---|---|---|---|
| KiPS c1 | iPS* | Keratinocyte derived | >20 | 46XX (P17) |
| FiPS 2a | iPS* | Fibroblast derived | 28 | 46XX (P5) |
| FiPS 2b | iPS* | Fibroblast derived | 32 | 46XX (P11) |
| FiPS 2c | iPS* | Fibroblast derived | >20 | 46XX (P5) |
| AdiPS 1 | iPS* | Adipose cells derived | 22 | 46XX (P11) |
| NOK | iPS** | Neural stem cell derived | >20 | 46XX (ND) |
| 201B7 | iPS*** | Fibroblast derived | 17 | 46XX (P8) |
| H1 | ES | WiCell Research Institute | 8 | 46XY (ND) |
| Shef6 | ES | University of Shefield | 7 | 46XX (ND) | iPS cells were generated in-house except for 201B7 generously gifted by Dr Shinya Yamanaka.
*Sendaivirus (4 Factors),
**PiggyBac (NANOG + OCT3/4 + KLF4),
***Retrovirus 4 Factors.
Chromosome counts were determined from 20 G-banded metaphase spreads.
ND: not performed

TABLE 1

B
Cytoscan HD array analysis

| | FGF/KSR | t2iL + Gö |
|---|---|---|
| H9 | P63 Amplification 14q23.2 14q23.3 20q11.21 | P11 Amplification 14q23.2 14q23.3 |
| H9 clone8 | P66 Amplification 14q23.2 14q23.3 | P12 Amplification 14q23.2 14q23.3 |
| FiPS2b | P19 No amplification No deletion | P6 No amplification No deletion |
| FiPS2c | P37 No amplification No deletion | P11 No amplification No deletion |
| FiPS c1 | ND | P18 Deletion 9p24 20p12.1 |

Cytoscan HD array analysis was used to detect copy number changes. Passage number in t2iL+Gö indicates passages since resetting. All samples are euploid and only minor deletions and amplifications were detected. Note these amplifications in H9 were already detected in parental PSC (FGF/KSR).

Figure 1H:
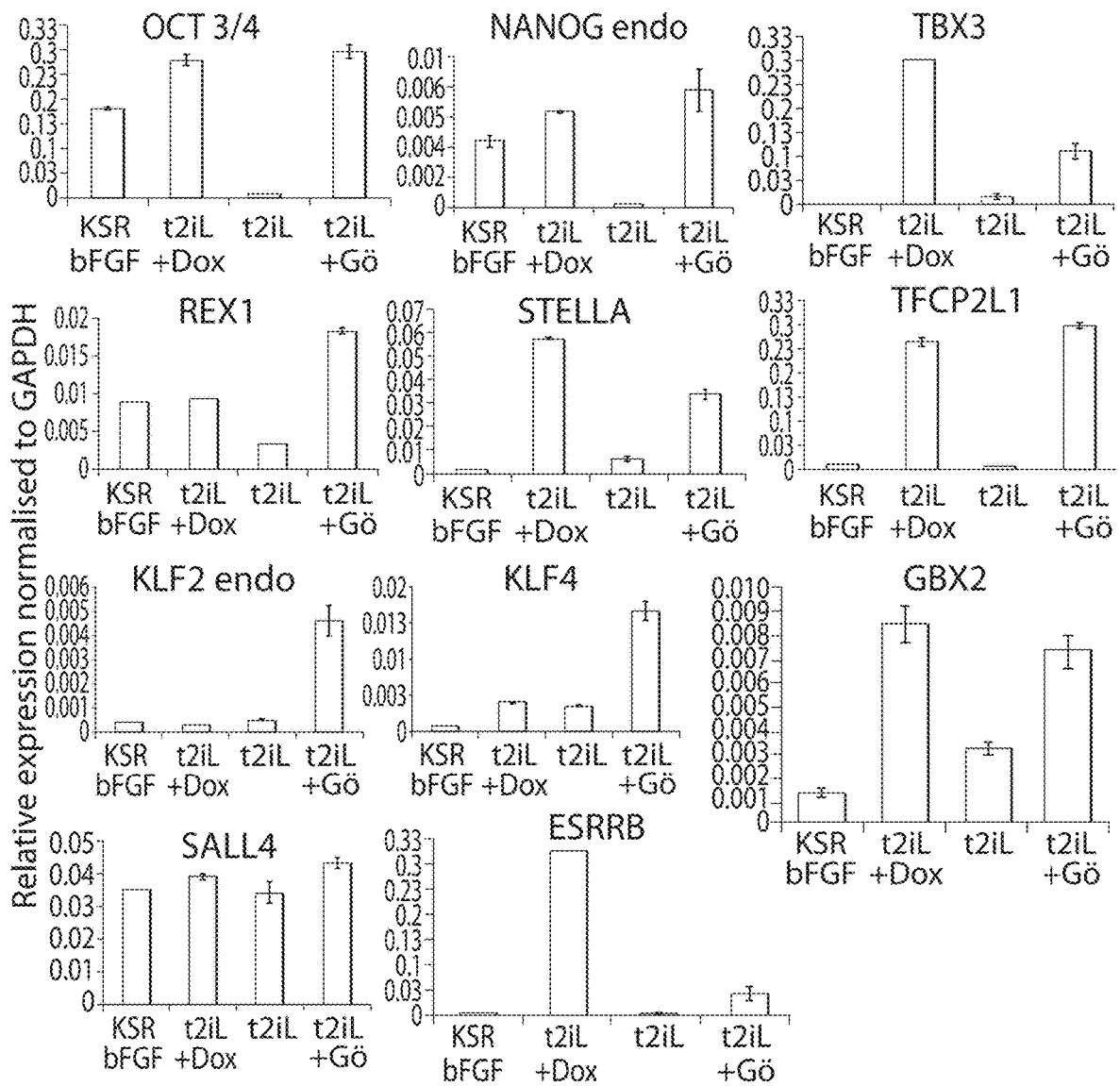
Figure 1I:
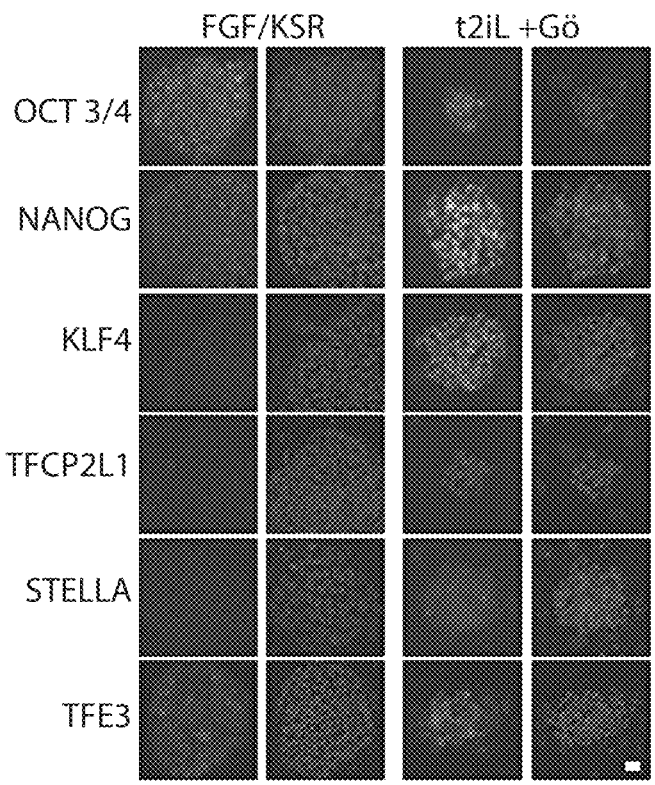

Following DOX withdrawal transgene products were generally undetectable by either reporter expression or qRT-PCR (FIG. 11). We profiled cells expanded in t2iL+Gö for the suite of transcription factors diagnostic of, and functionally implicated in, the mouse ES cell ground state (Dunn et al., 2014). Compared with no or minimal expression in conventional PSC, all factors were substantially up-regulated apart from ESRRB (FIGS. 1H and 12). Furthermore, relative to cells maintained in DOX, endogenous KLF2 and KLF4 mRNAs were increased, suggestive of negative feedback regulation. Protein expression was confirmed with available antibodies by immunostaining and immunoblotting (FIGS. 1I,J and 13). In addition, TFE3 was present in nuclei compared with cytoplasmic localisation in conventional PSC, as described for mouse ground state versus primed cells (Betschinger et al., 2013).

Figures 1J, 1K:
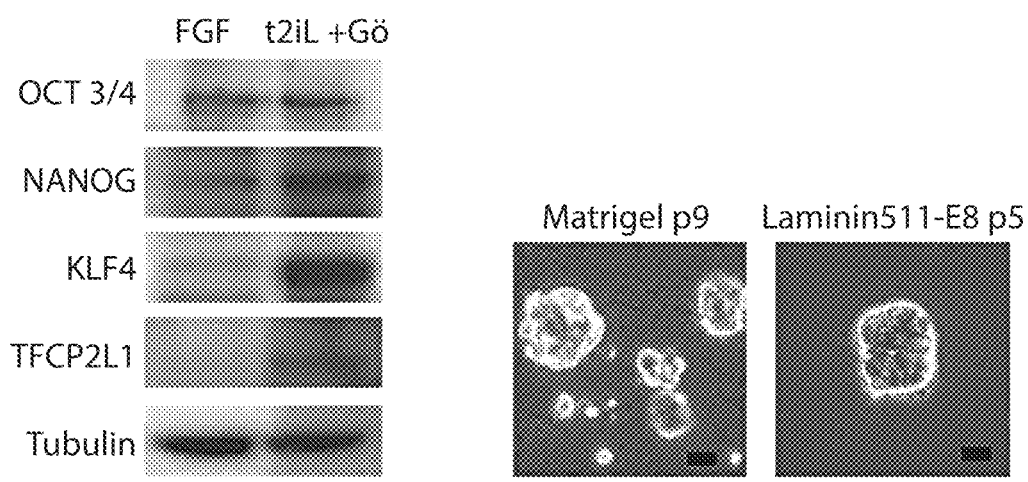
Figure 1L:
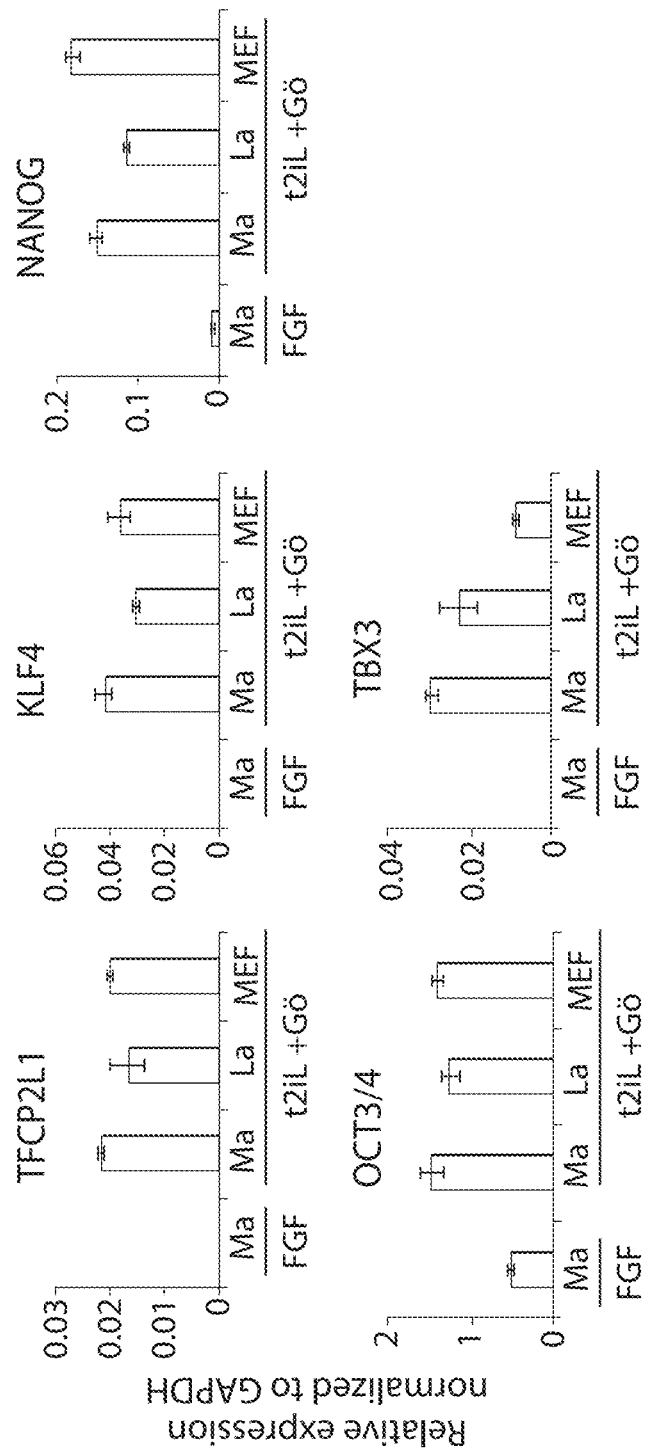

The preceding experiments were performed on feeders and we found that without feeders cultures rapidly deteriorated. Based on observations with mouse ESC we realised that Gö concentration was critical without buffering by feeders. We therefore reduced Gö to 2 µM and also added ROCKi prior to passaging. In these conditions reset cells could form undifferentiated colonies on Matrigel or laminin 511-E8 (Nakagawa et al., 2014) (FIG. 1K). On both substrates cells could be expanded, albeit more slowly on laminin, and ground state pluripotency factor expression was retained over several passages (FIG. 1L).

These observations indicate that NANOG and KLF2 can reset self-renewal requirements and transcription factor complement in human PSC and furthermore that this rewired state may be rendered independent of transgene expression by fine-tuning 2iL in combination with the PKC inhibitor Gö6983.

Differentiation Competence

Figure 2A:
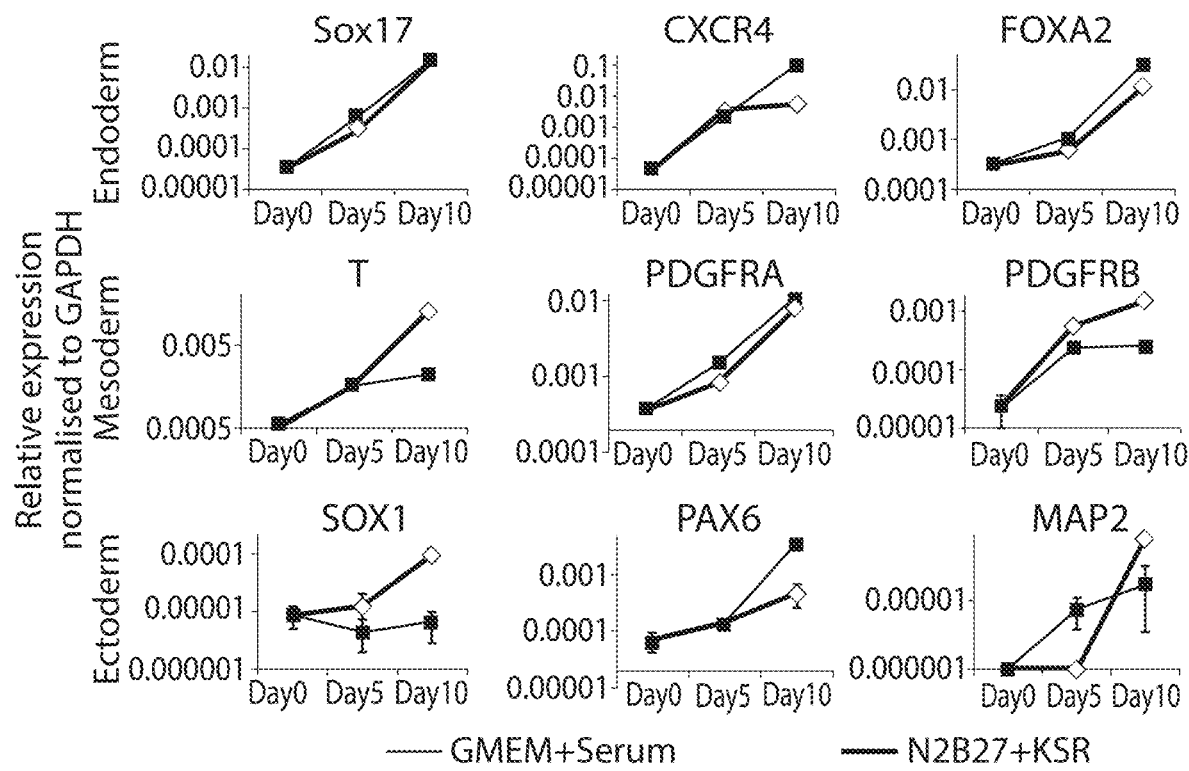
Figure 2B:
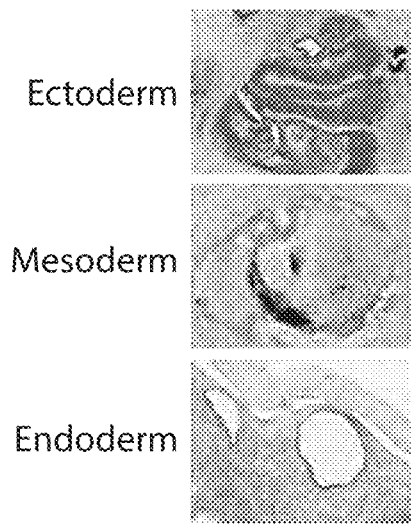

To test whether reset PSC are capable of germ layer specification we generated embryoid bodies. Cells expanded in t2iL+Gö without DOX were dissociated and allowed to aggregate in V-bottom wells either in N2B27 with KSR, or in GMEM and serum. Embryoid bodies were harvested after 5 or 10 days and analysed by qRT-PCR. Up-regulation of transcripts diagnostic of the three germlayers was pronounced in both conditions (FIG. 2A). Embryoid body outgrowths in serum gave rise to beating foci and up-regulated NKX2.2, ISL1, TNNT2 and MYOCD cardiac markers (FIG. 14). Differentiation potency was tested further by grafting to NOD/SCID mice. Cells transplanted directly from t2iL+Gö formed teratomas by 12 weeks. These tumours contained well-differentiated regions of neuroepithelium, cartilage, and digestive tract (FIG. 2B).

Figure 2C:
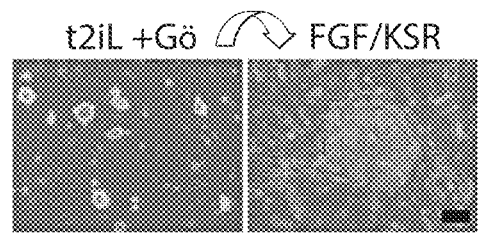
Figure 2D:
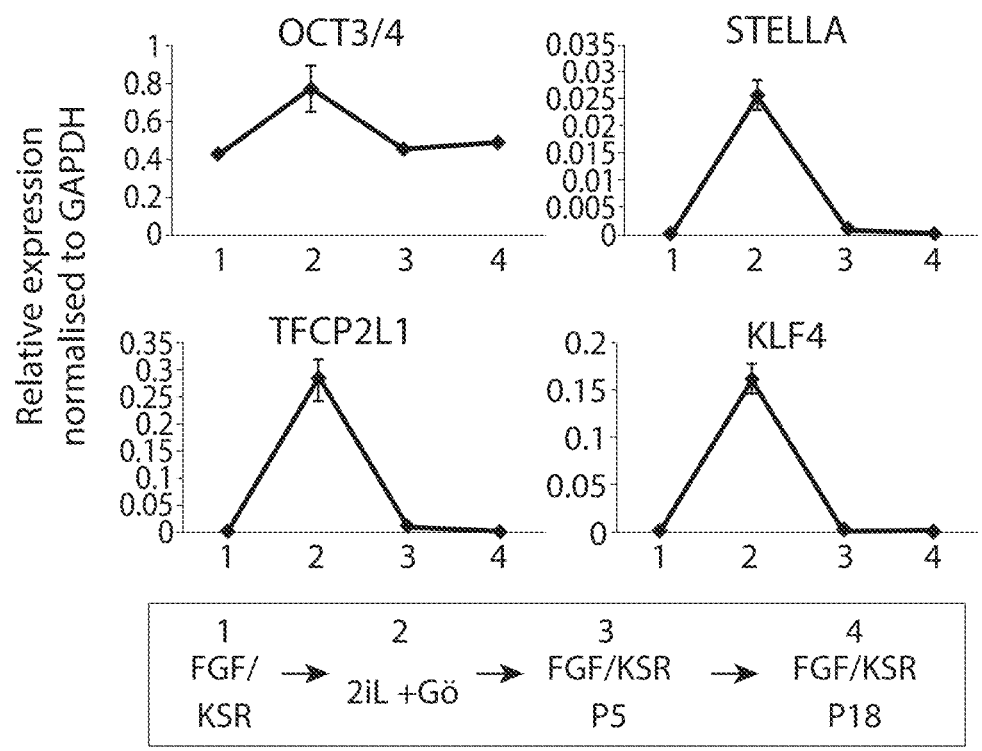
Figure 2E:
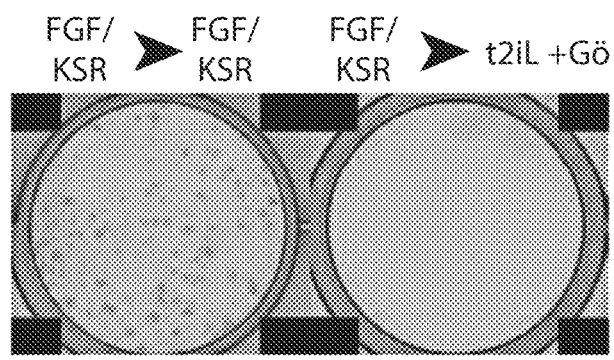
Figure 2F:
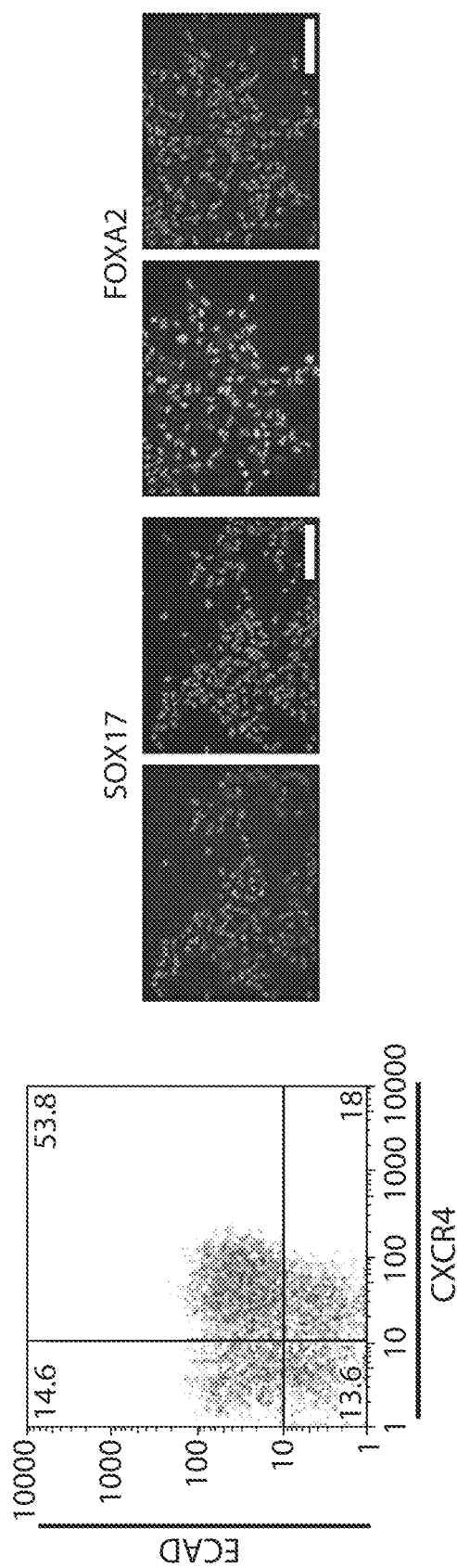
Figure 2G:
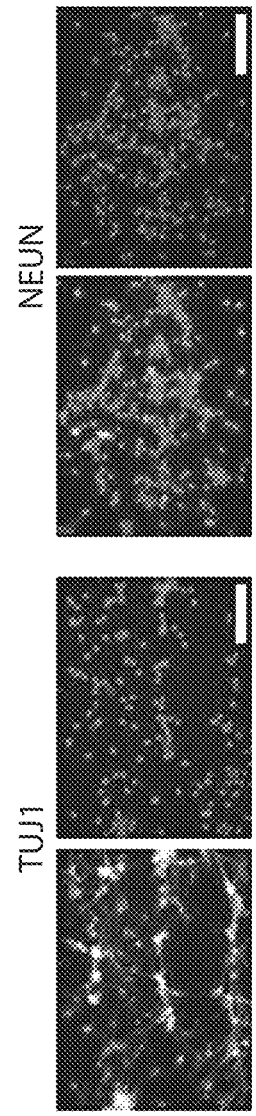

We noted that reset cells differentiated to a standard PSC phenotype upon transfer to FGF/KSR (FIG. 2C). This was accompanied by down-regulation of the ground state pluripotency factors (FIG. 2D). Stable change in cell state after culture for more than 2 passages in FGF/KSR was confirmed by complete loss of ability to form colonies in t2iL+Gö (FIG. 2E). We investigated whether reset cells could be channelled into adherent differentiation by exposure to FGF/KSR and application of protocols developed for conventional PSC. We found that reset cells exchanged into FGF/KSR for a few days responded to Activin and Wnt3A treatment (Kroon et al., 2008) by yielding a high proportion of cells double positive for ECADHERIN and CXCR4 (FIG. 2F). Definitive endoderm identity was corroborated by immunostaining for FOXA2 and SOX17. Conversely, treatment with Noggin and SB431542 (Chambers et al., 2009) resulted in large numbers of TuJ1 and NeuN positive neuronal cells with extended dendritic processes (FIG. 2G).

Treatment with FGF/KSR before the monolayer differentiation protocols was for the practical reason that the protocols have been designed for conventional human PSC cultured in that condition. In addition this procedure is consistent with developmental logic that cells should pass through a primed state before lineage commitment.

We conclude that reset cells can progress through a primed state into germ layer differentiation.

Mitochondrial and Metabolic Adjustment

Figure 3A:
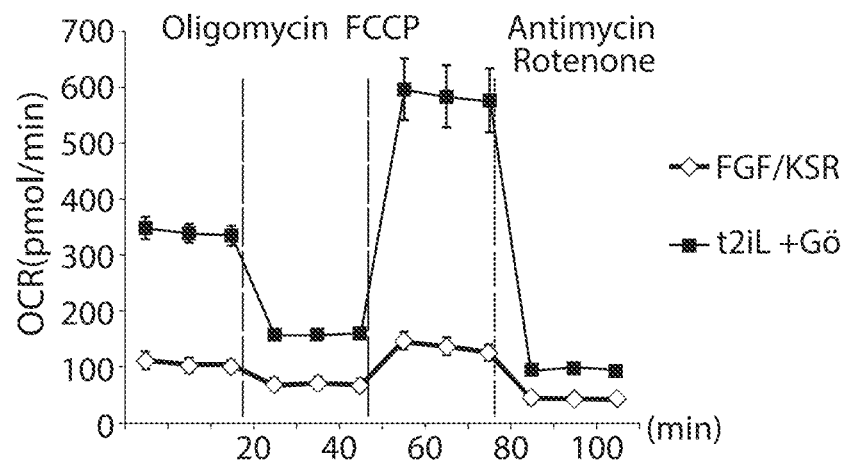
Figure 3B:
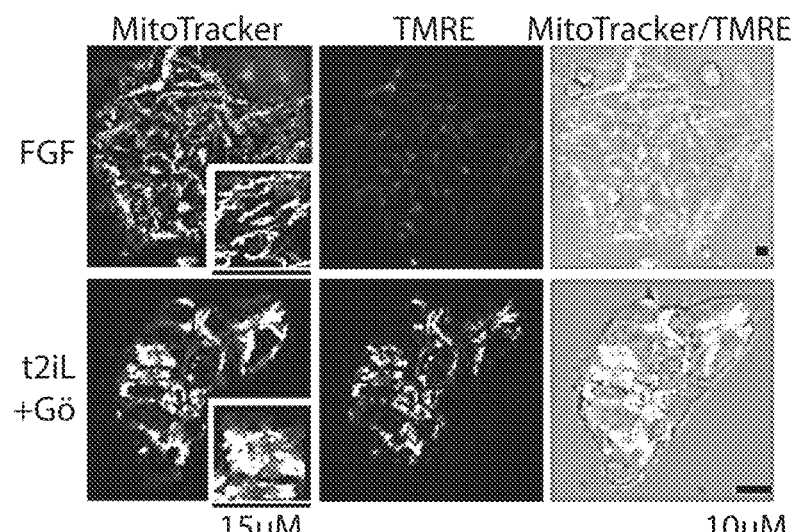
Figure 3C:
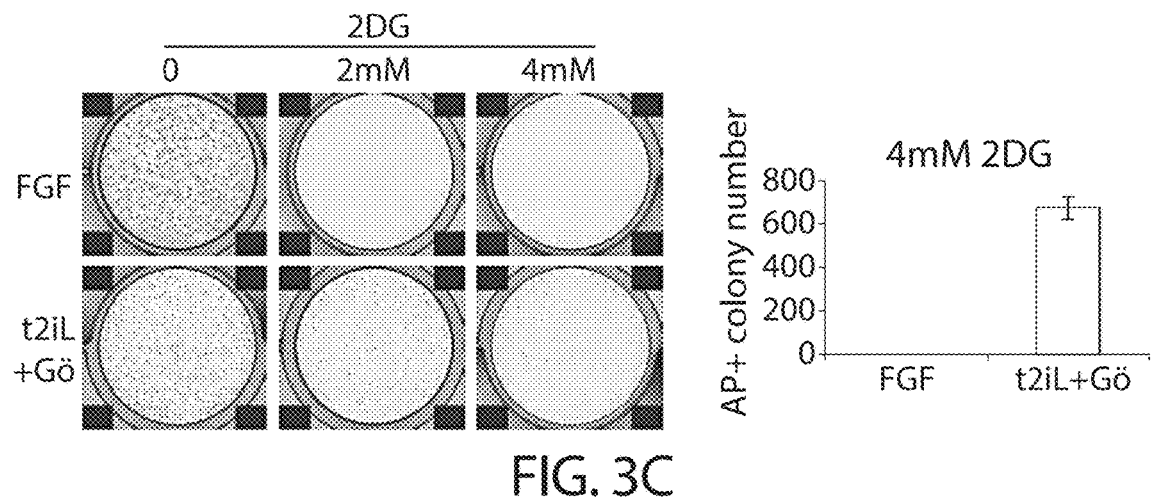
Figure 3D:
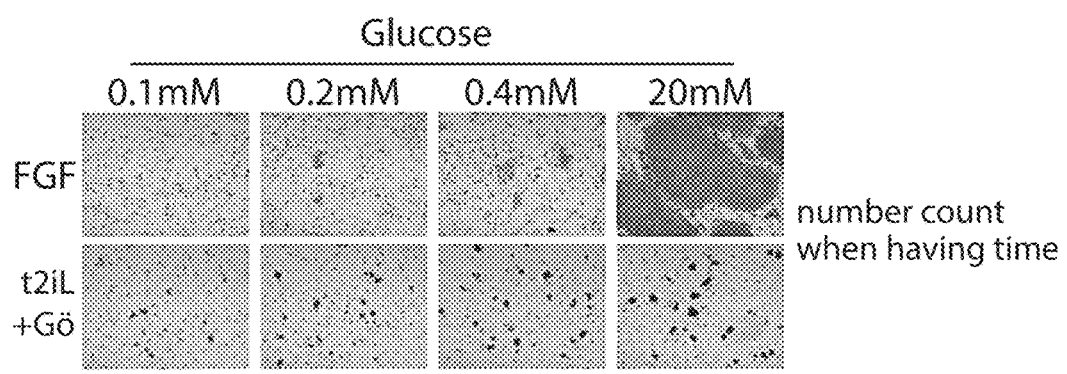

Mouse ESC utilise both mitochondrial oxidative phosphorylation and glycolysis whereas EpiSC/human PSC are almost entirely glycolytic and their mitochondria have very low respiratory capacity (Zhou et al., 2012). We measured basal oxygen consumption rate (OCR) and found it was substantially higher in reset cells than in conventional PSC (FIG. 3A). This difference was minimised in the presence of the mitochondrial ATPase inhibitor oligomycin. The mitochondrial uncoupler FCCP generated a greater OCR increase in reset cells than conventional PSC, consistent with higher mitochondrial electron transport chain (ETC) activity (FIG. 3A). Reset cells also displayed intense staining with tetramethylrhodamine methyl ester (TMRE), indicative of high levels of mitochondrial membrane depolarisation (FIG. 3B). Furthermore, analysis of the complex IV cytochrome c oxidase (COX) gene family revealed higher transcript levels in reset cells than conventional PSC for 14/17 expressed genes (FIG. 15), similar to findings for mouse ESC and EpiSc (Zhou et al., 2012).

We examined functional consequences of altered metabolic properties by culture in 2-deoxyglucose to inhibit glycolysis and in reduced concentrations of glucose to increase dependency on mitochondrial respiration. In contrast to conventional PSC reset cells formed undifferentiated colonies in the presence of 2-deoxyglucose (FIG. 3C) or as low as 0.2 mM glucose (FIG. 16).

These data indicate that resetting human PSC is accompanied by a profound metabolic realignment to a state comparable to ground state mouse ESC in which oxidative phosphorylation is fully operative alongside glycolysis.

Epigenetic Reorganisation

Figure 4A:
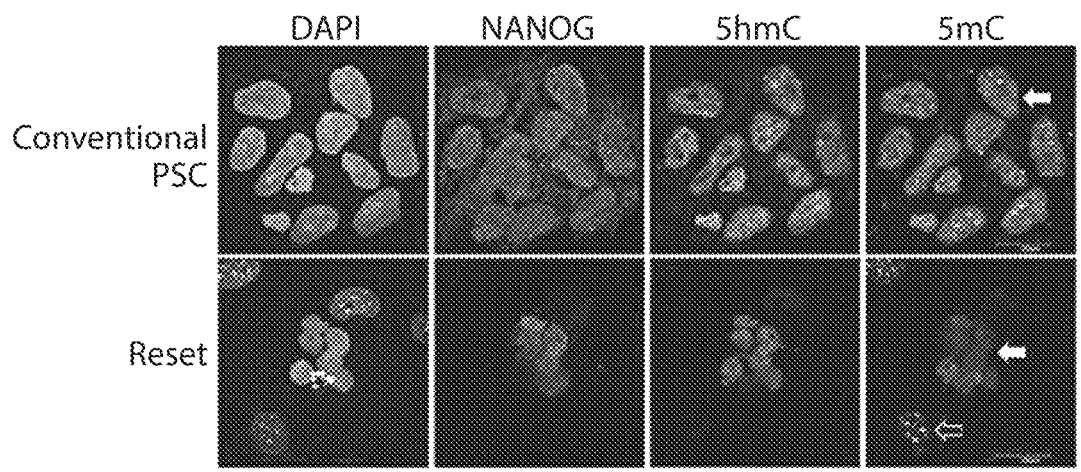
Figure 4B:
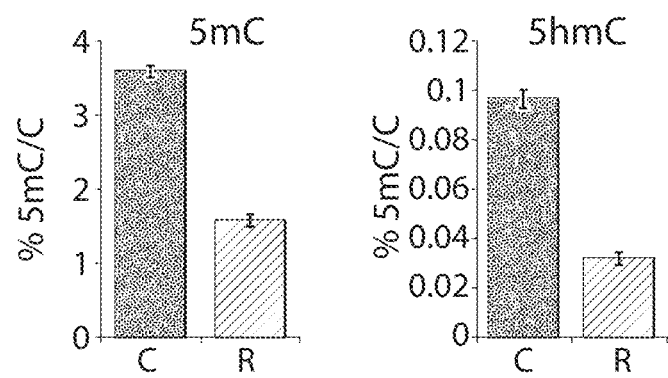
Figure 4C:
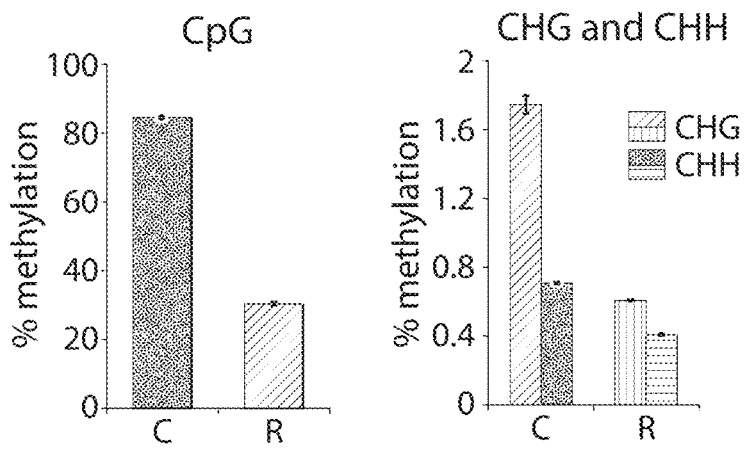
Figure 4D:
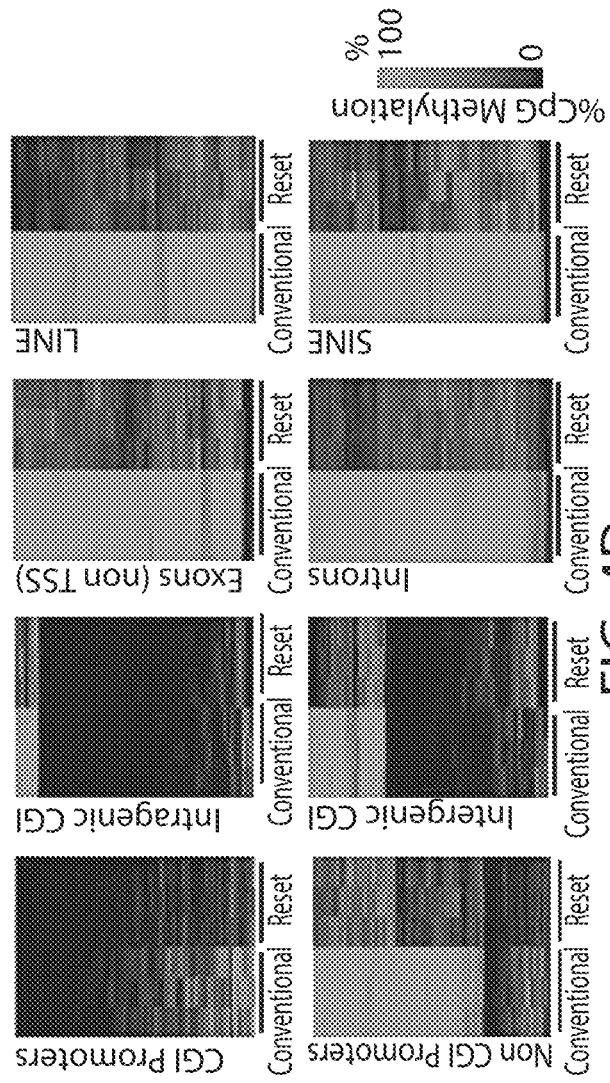

Global DNA hypomethylation is a feature of early embryo cells that is recapitulated in ESC cultured in 2i in contrast to the hypermethylation observed in EpiSCs (Ficz et al., 2013; Habibi et al., 2013; Leitch et al., 2013). We observed that immunofluorescence staining for 5-methylcytosine (5mC) was notably weaker in reset cells than conventional H9 cells (FIG. 4A). Mass spectrometric quantification confirmed a major reduction in total 5mC and also in 5-hydroxymethylcytosine (FIG. 4B). Through bisulphite sequencing (BS-seq) with 8.8× genome coverage (FIG. 17) we identified more than 50% loss of CpG methylation genome-wide (FIG. 4C). We also detected lower non-CpG methylation. Demethylation was substantial and widespread in most genomic contexts including gene bodies, non-CpG island (non-CGI) promoters, and the SINE and LINE1 transposon families (FIG. 4D), although at a minor subset of genes methylation was retained or even increased. A representative genomic interval shows hypomethylation across the SOX2 locus (FIG. 18).

Figure 4E:
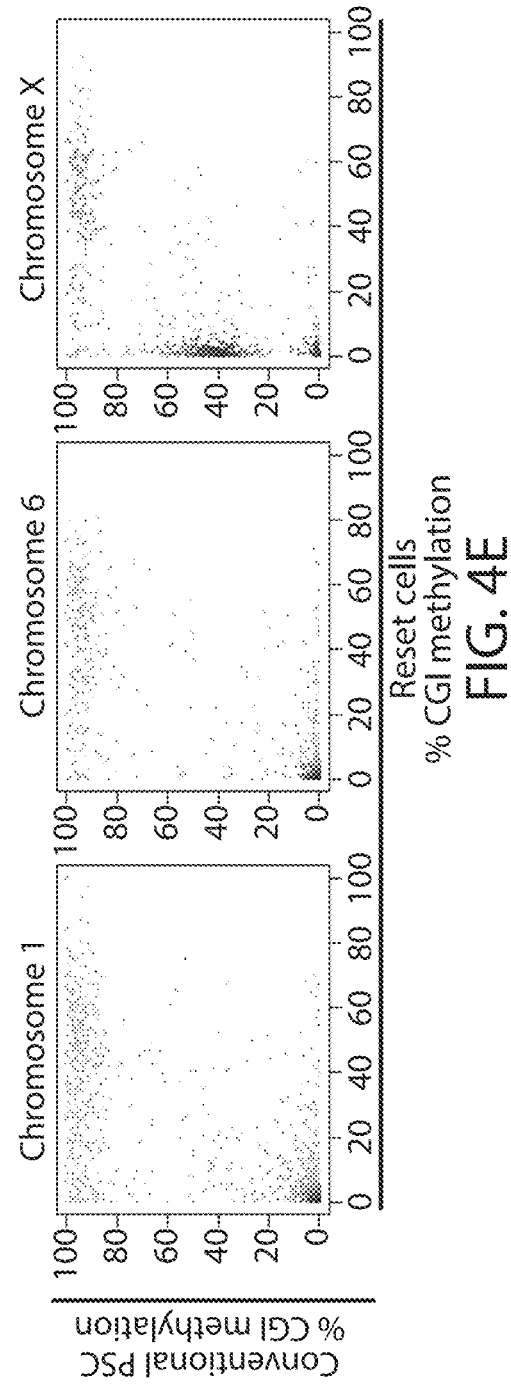
Figure 4F:
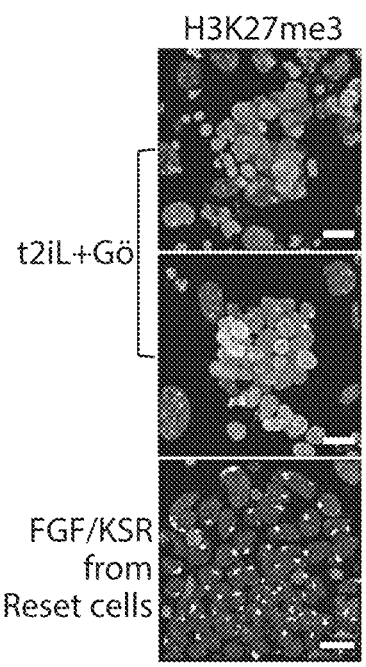
Figure 4G:
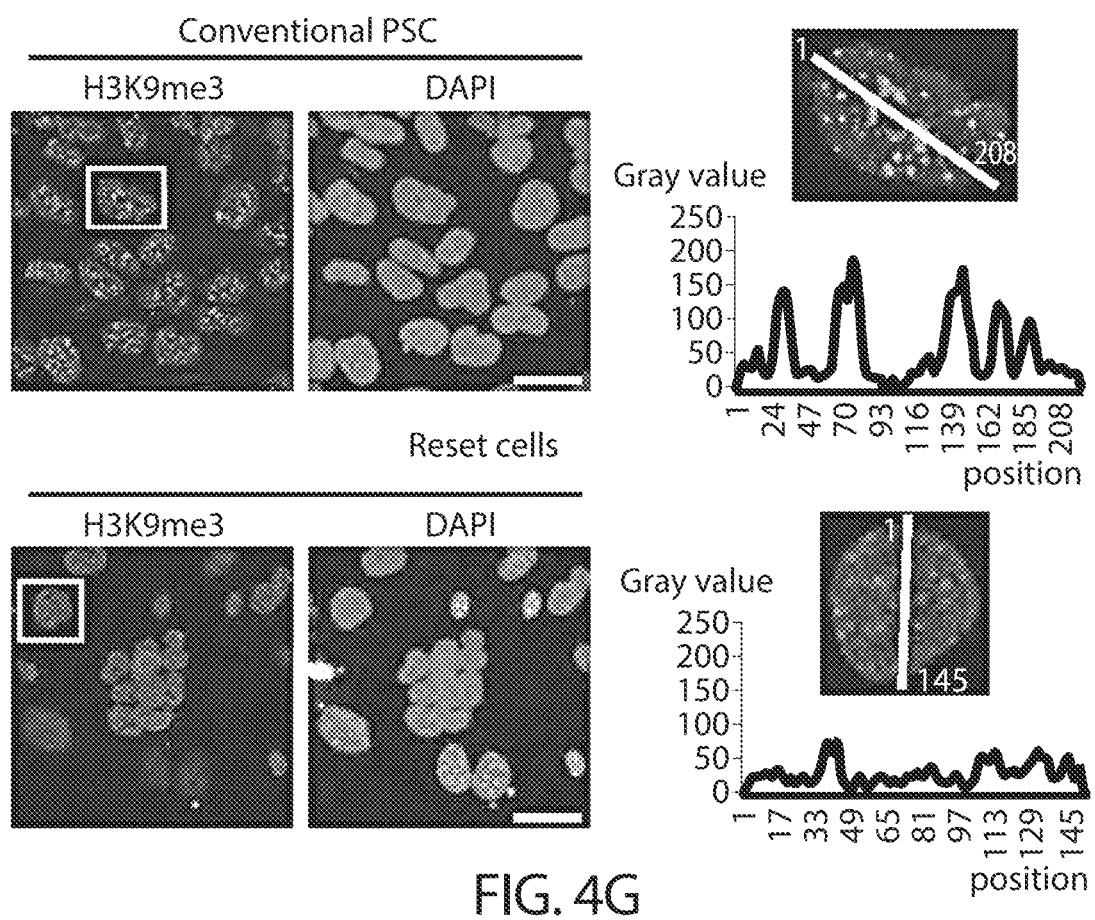

The X chromosome was demethylated as autosomes in reset cells, but with specific reduction in intermediate levels of CGI demethylation (FIG. 4E). Such intermediate levels are likely to reflect methylation of a proportion of X-linked CGIs in conventional PSC. Consistent with epigenetic erasure of the X chromosome we observed that foci of H3K27me3 were almost entirely lacking in reset XX cells (FIG. 4F), although as previously described (Silva et al., 2008; Tomoda et al., 2012) this modification was already lost in many of the parental cells. Notably, however, upon transfer of reset cells to KSR/FGF culture conditions foci of H3K27me3 appeared in the majority of cells within two passages.

We also examined by immunostaining the histone modification trimethylation of histone 3 lysine 9 (H3K9me3) associated with gene silencing. We found that reset cells exhibit much lower levels of this feature compared with conventional human PSC, recapitulating the difference observed between mouse ground state ESC and EpiSC (FIG. 4H, 19).

These data indicate that resetting the human PSC state is accompanied by a profound epigenetic deconstruction. Local demethylation has been described for purported human naïve PSC (Gafni et al., 2013), but no evidence has been provided for global changes or for demethylation of the X chromosome as we observe in reset cells. The global reduction in DNA methylation levels is strikingly similar in magnitude to the hypomethylation observed in mouse ground state ESC and in line with the demethylated status now reported for the human ICM (Guo et al., 2014; Smith et al., 2014).

Reconfiguration of the Global Transcriptome

We assessed the transcriptional state of conventional human PSC, human reset cells and mouse ESC by RNA reverse transcription coupled to deep sequencing (RNA-seq). Multiple independent conventional cultures of H9 and induced PSC were analysed alongside reset counterparts. Clustering by principal component analysis revealed mutually exclusive groups of conventional human PSC and reset cells, with distinct clusters of mouse ESC and human reset cells (FIG. 5A). Much of the variation (24%) is captured in the first principal component, indicating significant correspondence between reset cells and human blastocyst ICM (Yan et al., 2013). The two groups diverge with respect to the second principal component, accounting for 14% of sample variance. This is not unexpected given that mouse ESC bear closest resemblance to epiblast cells in the late blastocyst rather than immature ICM cells (Boroviak et al. 2014). Primary explant ICM cells propagated in standard conditions take on the attributes of conventional PSC cultures and adopt similar expression profiles (light to dark blue circles). This contrasts with ground state mouse ESC which show relatively little deviation from naïve epiblast (Boroviak et al., 2014).

Figure 5B:
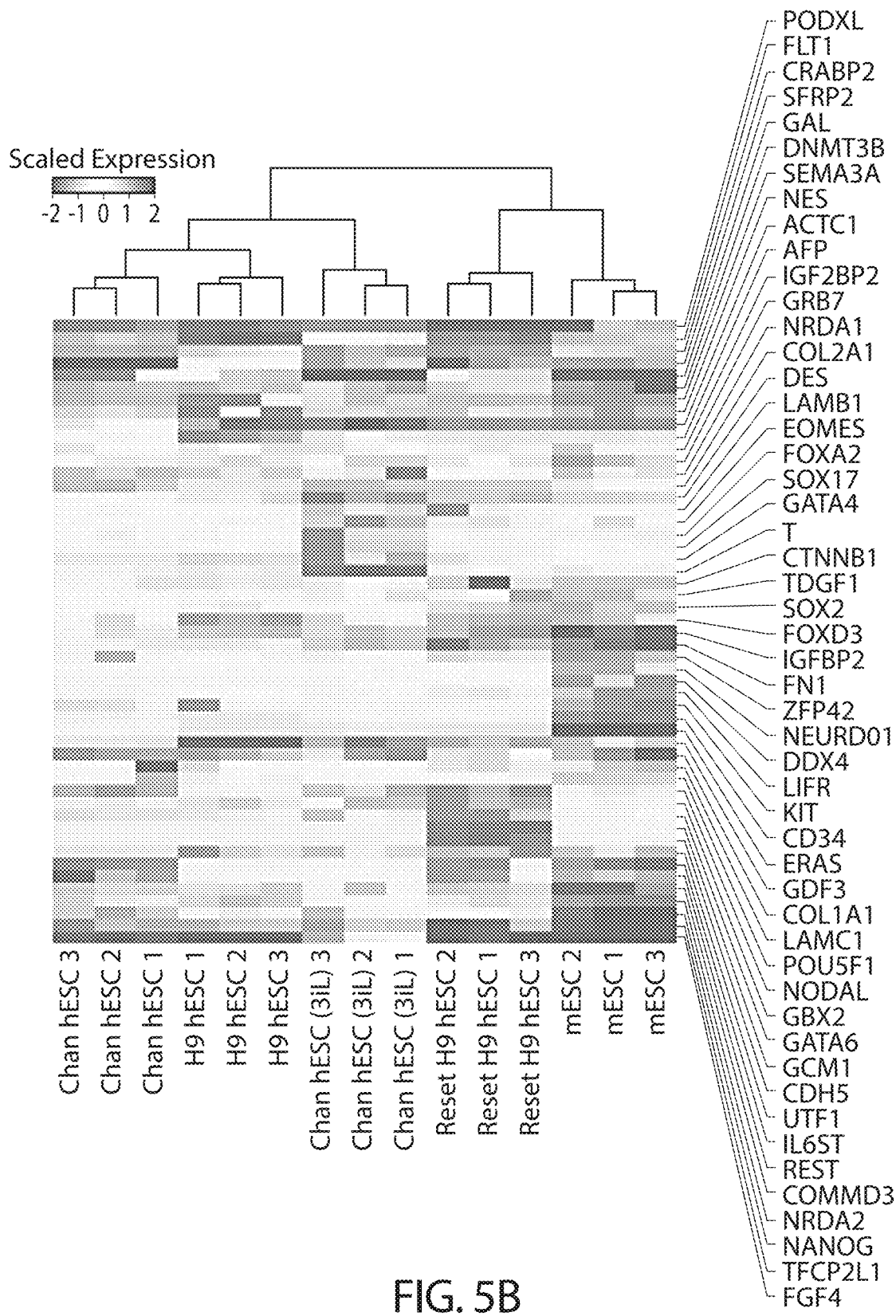

Examination of the genes contributing to the first two principal components confirms the influence of pluripotency factors in reset cells and of lineage-specific genes in conventional PSC (FIG. 20). Further analysis of differential expression shows that reset cells and ESC share similar patterns with respect to upregulation of pluripotency regulators and repression of lineage markers (FIG. 5B). The comparison presented is based on an independent panel of genes selected by the International Stem Cell Initiative (Adewumi et al., 2007) and commonly used in human and mouse stem cell pluripotency arrays. In contrast to conventional PSC, robust expression was observed of ground state pluripotency regulators in both reset cells and ground state ESC. This is accompanied by repression of lineage-specific genes. Reset cells and ESC form a distinct cluster characterised by the robust expression of naïve pluripotency markers including NANOG, KLF4 and TFCP2L1. In contrast, PSC cultured in conventional media feature or the 3iL formulation (Chan et al., 2013) exhibit prominent expression of lineage markers such as AFP, ACTC1, Brachyury and EOMES. Gene Ontology analysis of differentially expressed genes indicated enrichment of functional categories representative of developmental pathways.

We additionally compared reset and conventional PSC cultures with cells purported to have undergone conversion to a naïve state in recent reports (Chan et al., 2013; Gafni et al., 2013). To facilitate direct comparison samples were hybridised to the microarray platform applied in Gafni et al. We profiled an extended panel of samples, including reset cells and standard counterparts from H9 and two independent iPS cell lines derived from fibroblasts and adipose stem cells, in addition to those profiled by RNA-seq above (see Methods). Data from each study were normalised to conventional human embryo-derived PSC to integrate microarray and RNA-seq datasets (see Methods). A significant departure from the conventional state was not apparent for cell lines propagated in alternate culture regimes, suggesting they have not fundamentally changed from standard human PSC (FIG. 5A). Analysis of data from Gafni et al. (2013) on cells derived with the NHSM protocol reveals wide variation across individual lines, but relatively minor divergence from other conventional human PSC cultures (FIG. 21, 22).

Figure 5C:
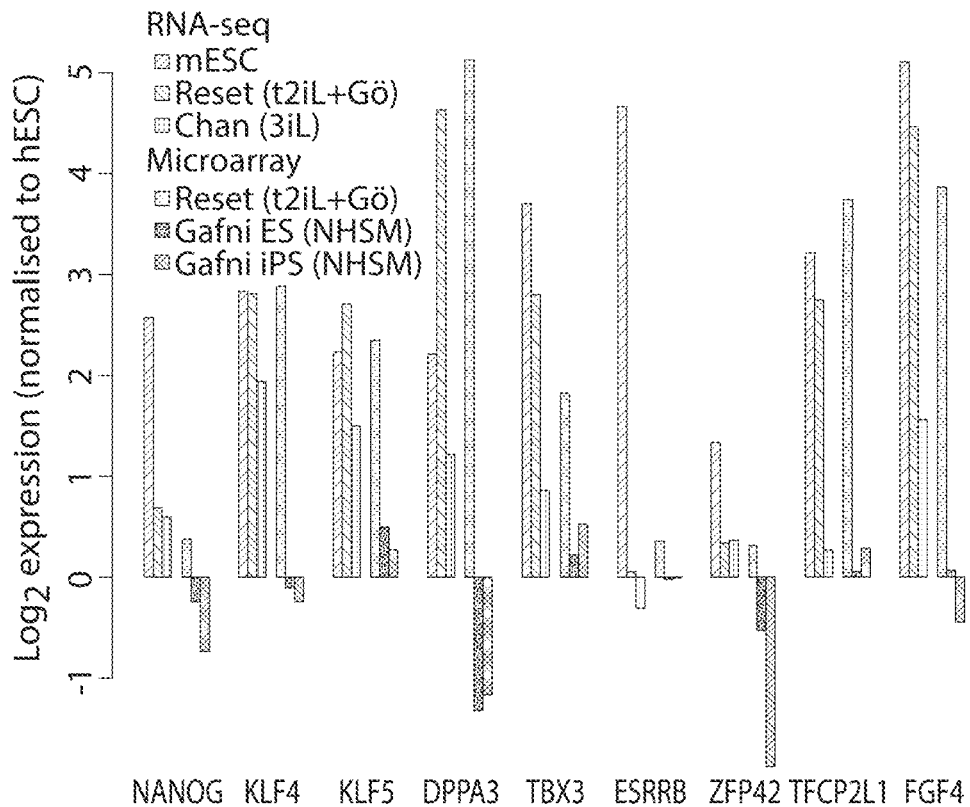
Figure 5D:
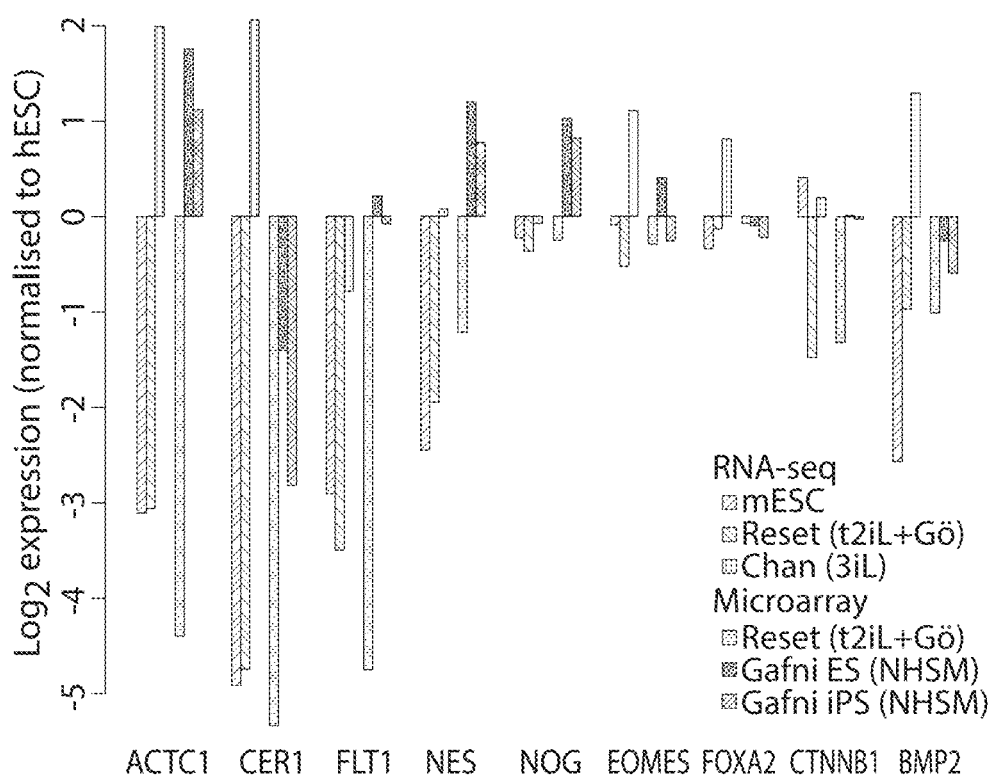

Reset cells display expression patterns characteristic of ground state ESC, in contrast to NHSM cultures where, remarkably, the expression of key pluripotency factors is often downregulated or abolished (FIG. 5C). The inverse trend was evident when examining a range of lineage-specific genes, which are heavily downregulated in ESC and reset cells but display spurious expression in NHSM and 3iL cultures (FIG. 5D). A range of chromatin modifiers was also found to exhibit trends more comparable to mouse ESC for reset cells than for alternative cultures, with NHSM cells lacking expression of important epigenetic regulators such as MLL3, NCOA3 and TETs (FIG. 23). Finally, in line with the observed DNA hypomethylation in reset cells, transcripts for DNMT3B were greatly reduced and for DNMT3L increased, (Neri et al., 2013).

We examined expression of two key factors, TFCP2L1 and KLF4, in human embryos, to evaluate if the ground state pluripotency factors defined in mouse and up-regulated in human reset cells are indeed expected features of human naïve pluripotency.

Figure 5E:
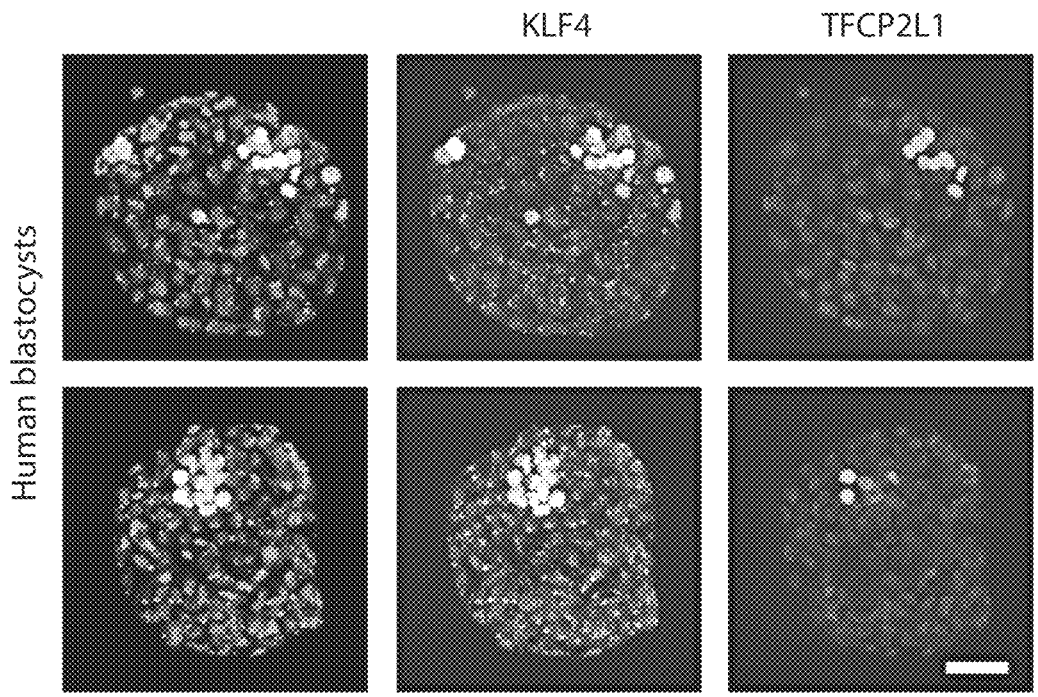
Figure 5F:
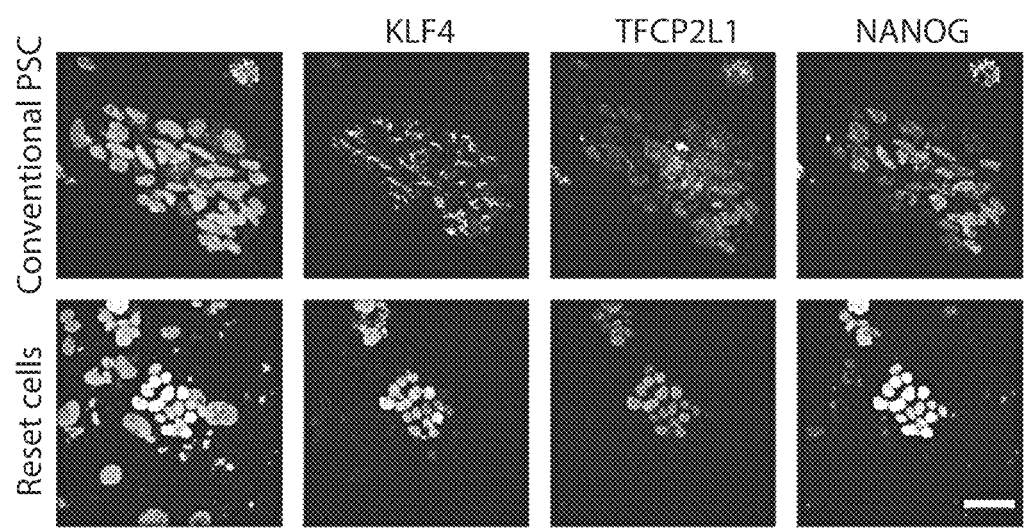

Supernumerary frozen embryos from clinical in vitro fertilisation programmes were thawed and cultured as described (Roode et al., 2012). Embryos that developed to the expanded blastocyst stage were processed for immunostaining. We detected KLF4 staining exclusively in the inner cell mass (FIG. 5E). TFCPL1 staining was faint throughout the embryo but intense staining was evident only within the ICM in a subset of the KLF4 positive cells. Thus the ICM in the mature human blastocyst contains cells double positive for KLF4 and TFCP2L1 protein, neither of which is up-regulated in previously described human PSC (FIG. 5C) but both of which are rather uniformly co-expressed in reset cells along with NANOG (FIG. 5F), as in mouse ESC.

In summary, the meta-genomic comparison of transcriptome data from our own study with that published in the Gafni and Chan studies shows that reset cells we generate are both globally distinct from standard human pluripotent stem cells and highly consistent across cell lines. In contrast, based on systematic analysis of their own datasets, no consistent or substantive change in cell identity from conventional human pluripotent stem cells is apparent in either the Gafni or Chan study.

Executive Operation of the Ground State Transcription Factor Circuit

Figure 6A:
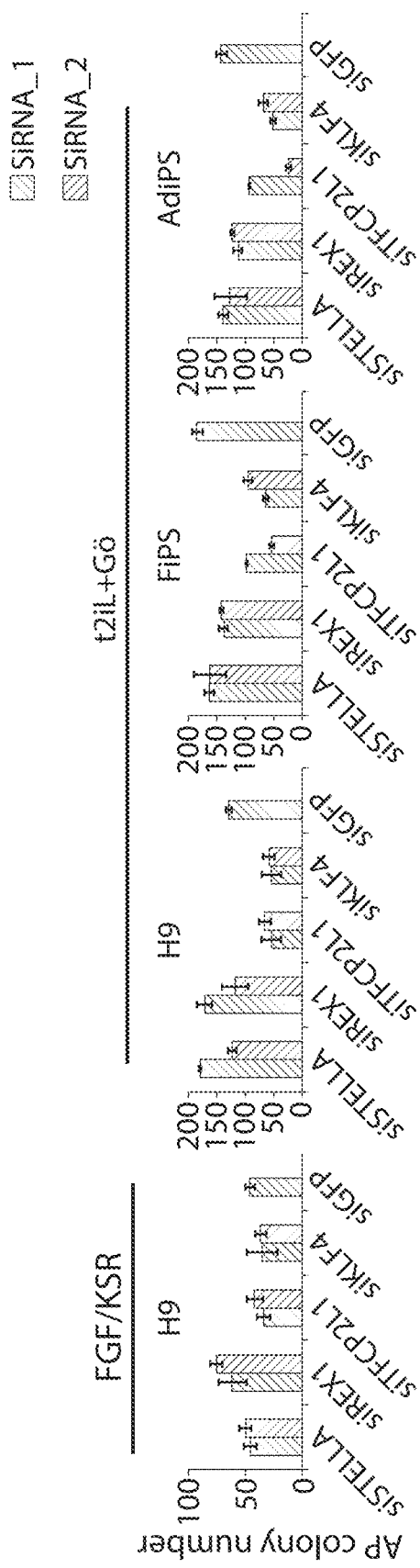
Figure 6C:
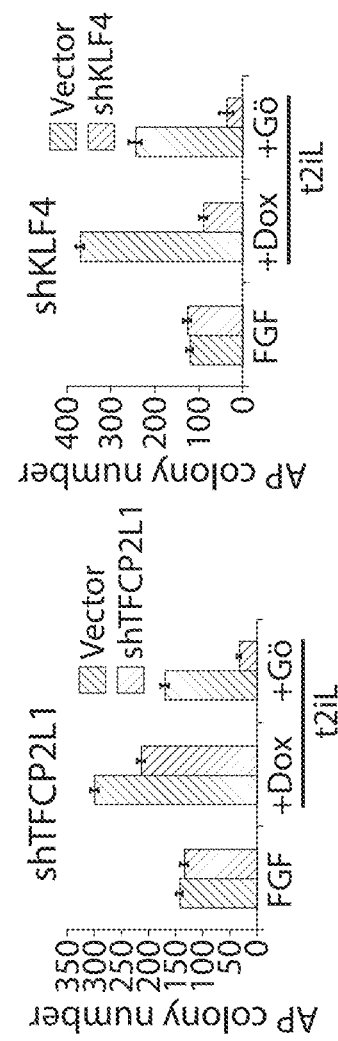
Figure 6B:
Figure 6D:
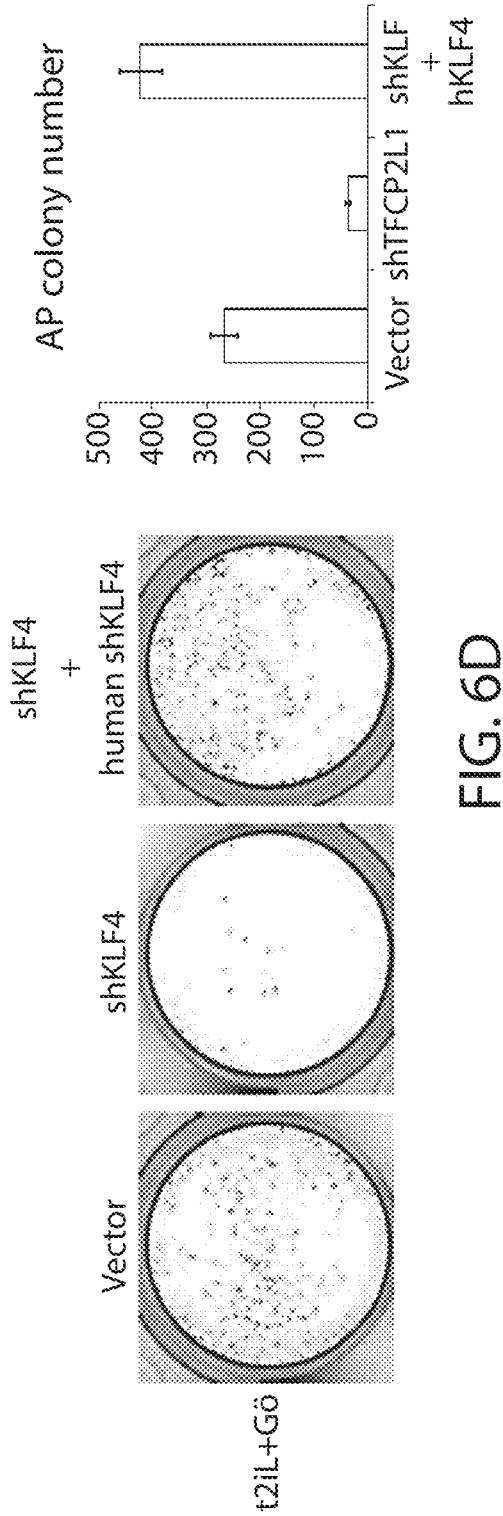

To determine if the ground state transcription factor circuit is functional and essential in reset human cells we tested dependency on ground state transcription factors using RNAi. We employed pooled siRNAs in the first instance and repeated with two individual siRNAs for each gene. siRNA against non-essential naïve pluripotency markers REX1 (ZFP42) and STELLA (DPPA3) did not impair colony formation by either reset or conventional PSC (FIG. 6A). In contrast, knockdown of KLF4 or TFCP2L1 markedly reduced formation of alkaline phosphatase (AP) positive undifferentiated colonies by reset cells but had little effect on conventional cultures. We then used shRNA to achieve constitutive knockdown (FIG. 25). When NANOG and KLF2 transgenes were maintained with DOX, TFCP2L1 or KLF4 knockdown was tolerated but cells showed reduced colony formation (FIG. 6B). After DOX withdrawal differentiation and death ensued in t2iL+Gö, but knockdown cells survived if transferred to FGF/KSR and adopted flattened morphology like conventional PSC. In low density plating assays, colony formation was largely abolished by knockdown in t2iL+Gö but unaffected in FGF/KSR/ROCKi (FIG. 6C, 26). TFCP2L1 shRNA targets the coding sequence. Expression of mouse Tfcp2l1 partially rescued the knockdown phenotype (FIG. 27). KLF4 shRNA targets the 3'UTR and expression of the human KLF4 open reading frame fully restored colony formation (FIG. 6D).

Figure 6E:
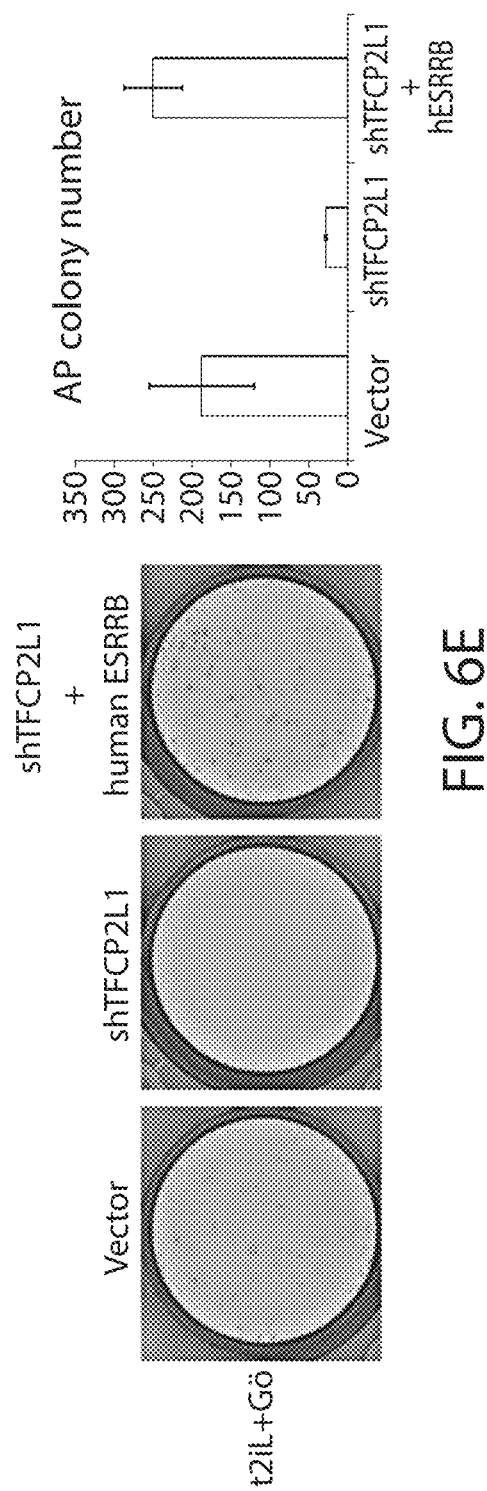

In presence of both 2i and LIF mouse ESC can withstand Tfcp2l1 depletion due to compensation by Esrrb downstream of GSK3 inhibition (Martello et al., 2013). Reset human cells may be sensitised due to weak expression of ESRRB. We therefore tested whether transgenic ESRRB can rescue colony formation upon TFCP2L1 knockdown. Indeed, ESRRB expression rendered reset cells resistant to TFCP2L1 shRNA such that they formed multiple colonies in t2iL+Gö that had refractile domed morphology and could be expanded after passaging (FIG. 6E).

These findings indicate that the self-renewal of reset human cells, but not conventional PSC, is strongly reliant on TFCP2L1 and KLF4 and furthermore point to conserved functionality of ground state transcription factors between mouse and human, even though regulation of individual factor expression may be altered.

Figure 6F:
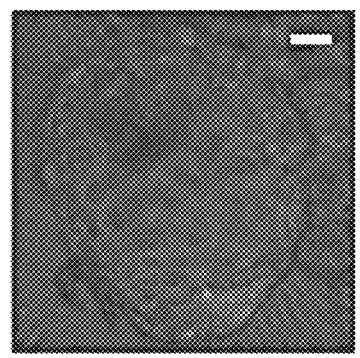
Figure 6G:
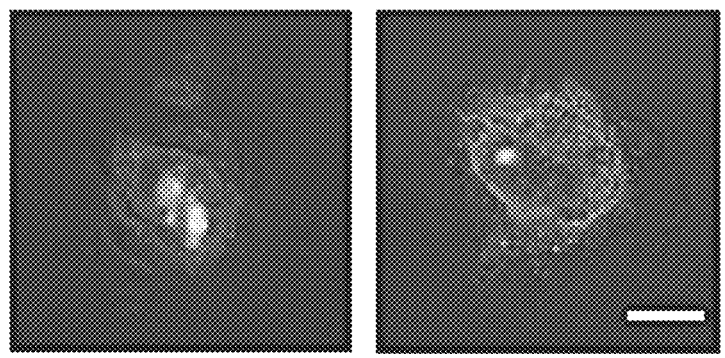

As a potential functional test of naïve epiblast identity we introduced reset cells into mouse pre-implantation embryos and monitored development in vitro. For this we first used fibroblast-derived induced PSC stably transfected with CAG-Cherry before and after resetting. After morula aggregation using conventional iPSC we did not detect any Cherry positive cells 48 hours later in 37 blastocysts. In contrast reset cells contributed to the ICM in 6 out of 42 blastocysts, and in some cases appeared well integrated in the epiblast compartment (FIG. 6F). We repeated this test on reset cells harbouring a GFP reporter line that gave more homogeneous expression. We observed GFP positive cells within the ICM/epiblast in 8 of 49 blastocysts. We then assessed whether reset cells could be incorporated into the ICM by blastocyst injection. Injected embryos were cultured for 72 hours to allow hatching, attachment and primary ICM outgrowth. Of 32 injected embryos 9 showed GFP positive cells within the mature ICM/epiblast (FIG. 6G).

These data show reproducible integration of reset cells into the ICM after introduction into early mouse embryos by both morula aggregation and blastocyst injection. Incorporation is not observed with conventional human PSC. The data suggest that human reset cells are sufficiently similar to mouse naïve cells to allow incorporation into the ICM and pre-implantation epiblast.

Transient Transgenesis and Stable Resetting

Figure 7A:
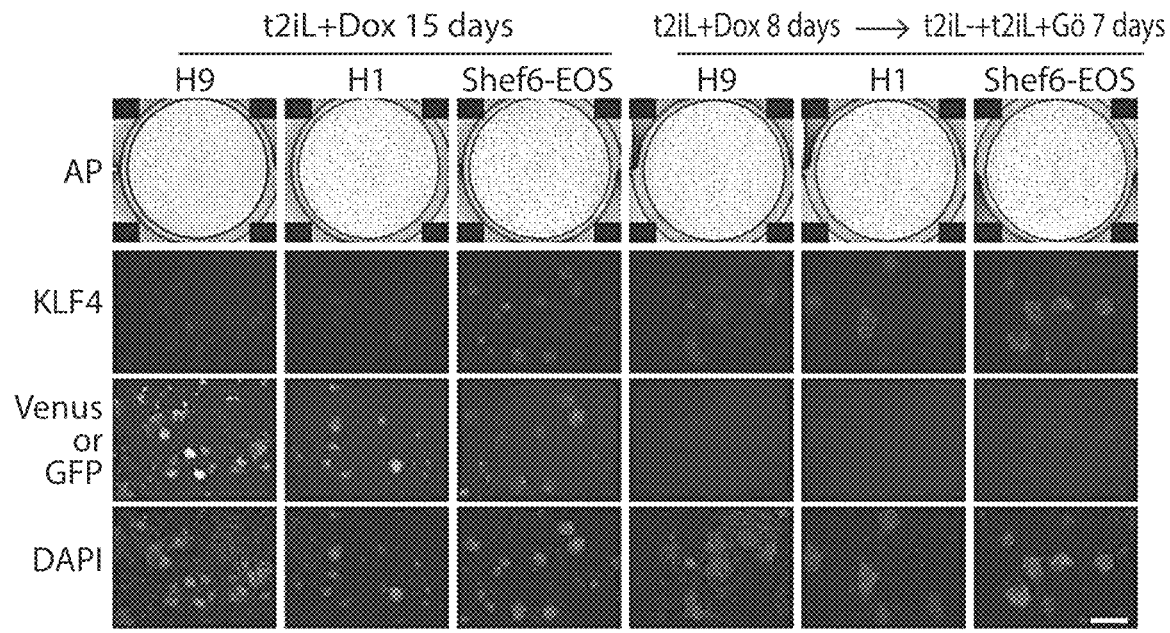
Figure 7B:
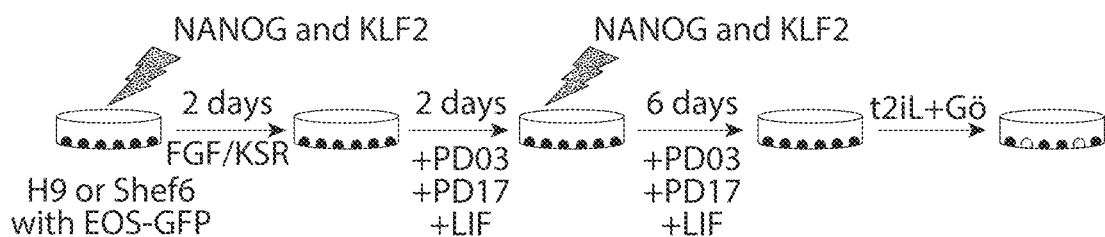
Figure 7C:
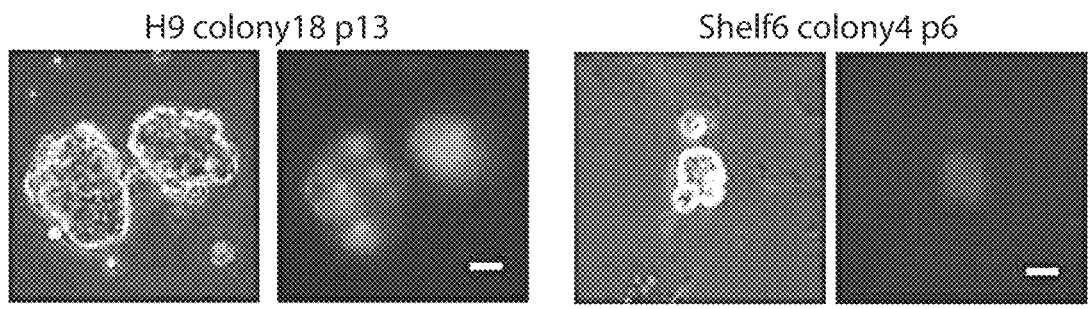
Figure 7D:
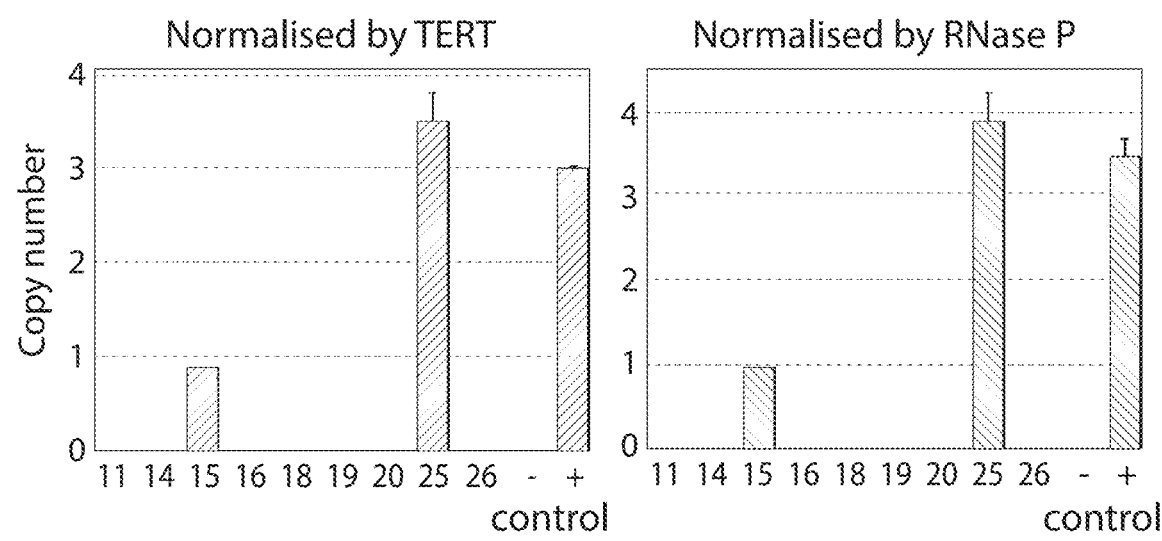
Figure 7E:
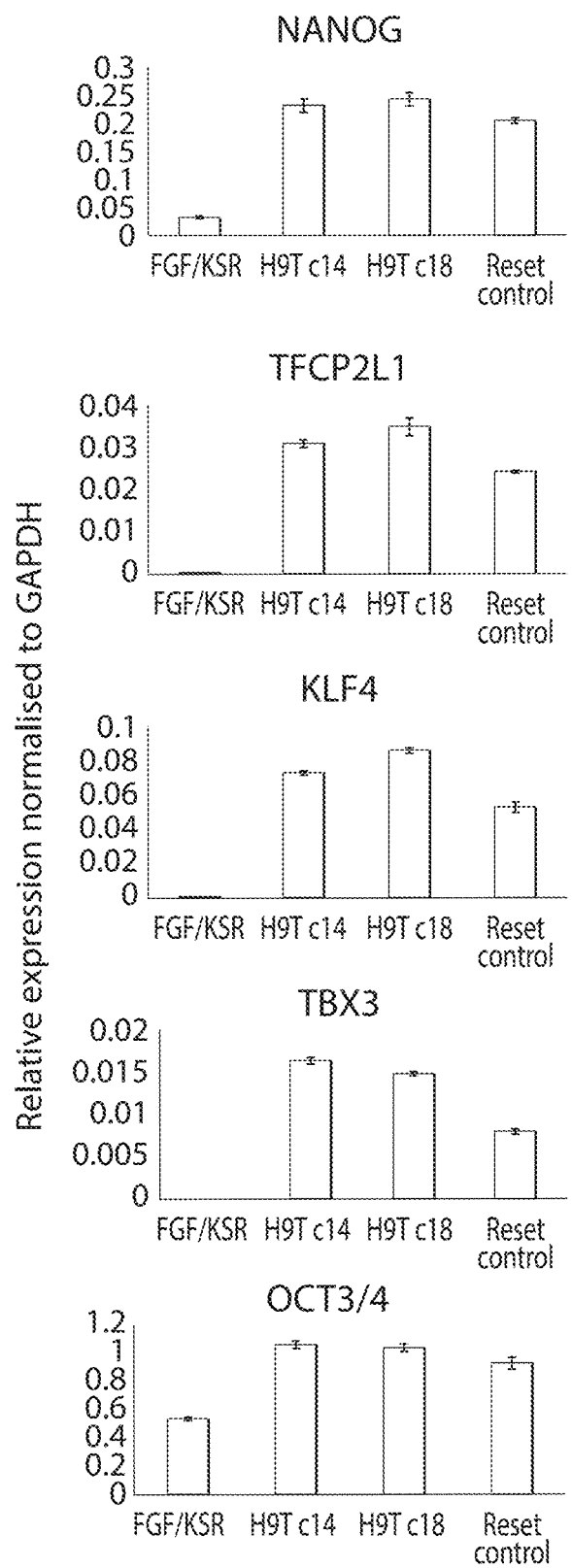
Figure 7F:
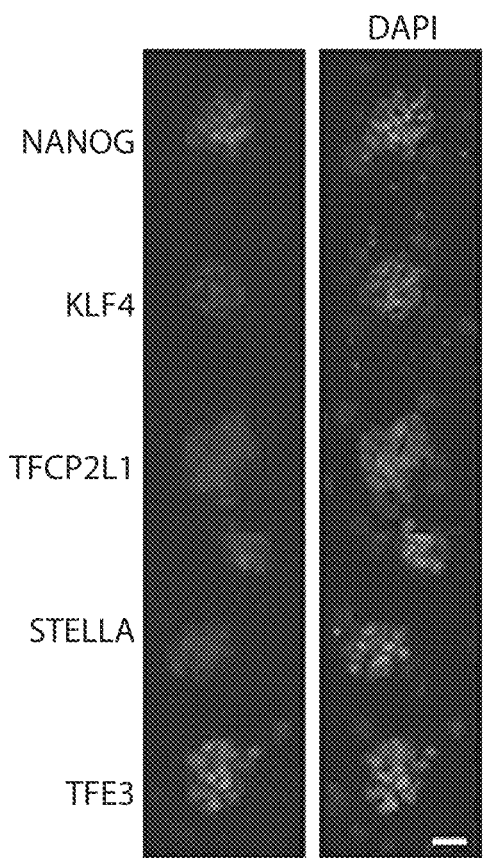
Figure 7G:
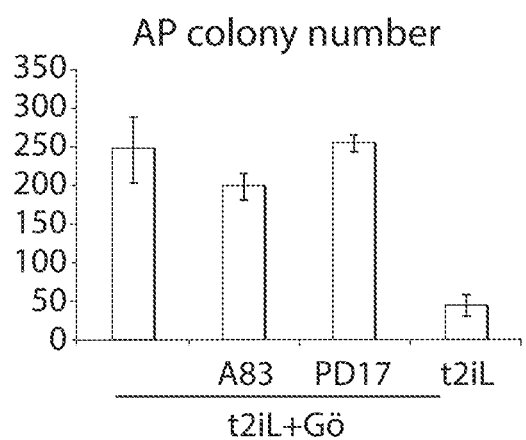
Figure 7H:
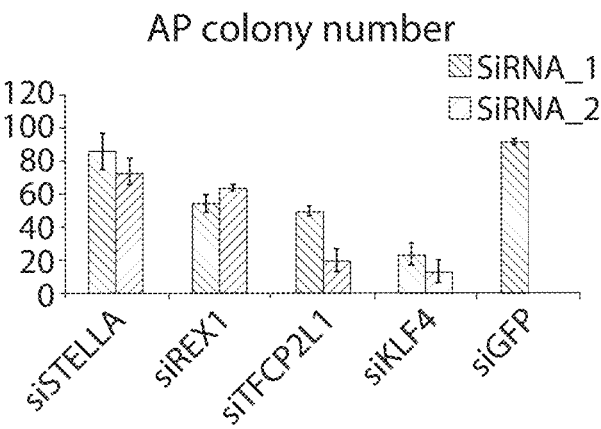
Figure 7I:
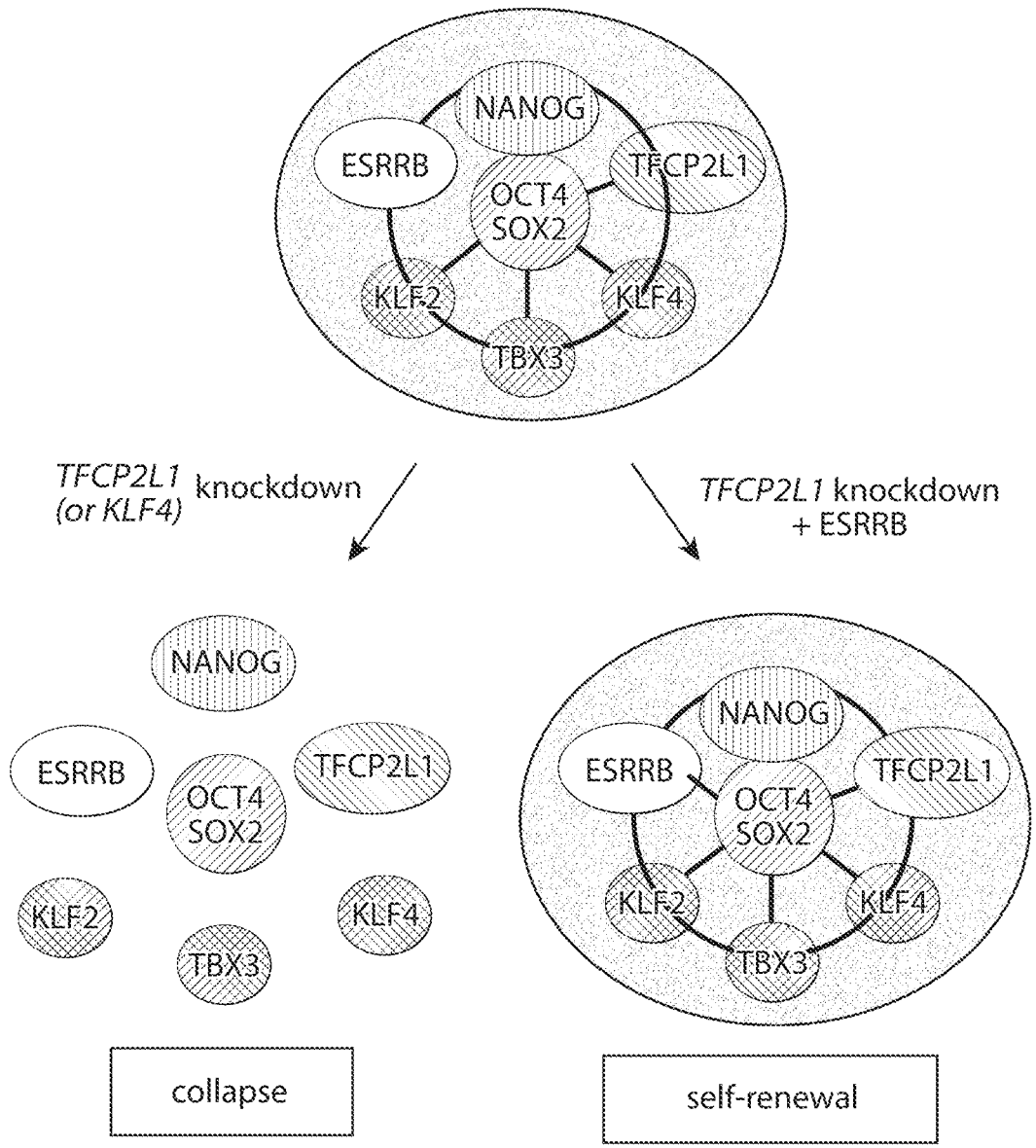

We investigated the timespan for resetting by inducing NANOG/KLF2 expression with DOX for finite intervals then assaying colony formation in t2iL+Gö. This revealed that 8 days of induction was sufficient (FIG. 7A). We reasoned that equivalent transgene expression should be achievable by transient transgenesis. To identify and select for potential reset cells we exploited the EOS construct (Hotta et al., 2009) based on the mouse Oct4 distal enhancer that drives expression in naïve but not primed pluripotent cells. We subjected H9 and Shef6 cells bearing an integrated PB-EOS-GFP/puro$^R$ construct to transfection with constitutive expression plasmids for NANOG and KLF2 (FIG. 7B). In pilot experiments we observed that CH appeared inhibitory to the resetting process and that addition of the FGF receptor inhibitor PD17 might favour resetting. Accordingly two days after transfection medium was switched from KSR/FGF to N2B27 supplemented with PD17 along with PDO3 plus hLIF. At day 4, cells were retransfected and on day 8 medium was changed to t2iL+Gö. From day 12, several GFP positive clusters of cells became visible and puromycin selection commenced. Cultures remained heterogeneous and were passaged 4 times before colonies were picked and expanded in t2iL+Gö (FIG. 7C). Genomic PCR was used to screen for integration of the CAG promoter region and a Taqman copy number assay probe was employed against the blasticidin resistance gene present in both NANOG and KLF2 constructs. Seven cultures out of 9 showed no detectable transgene at single copy resolution (FIG. 7D). These were indistinguishable in morphology from cultures in which transgenes were detected or from reset cells generated previously with inducible transgenes. qRT-PCR and immunostaining confirmed sustained expression of ground state pluripotency factors (FIG. 7E, F). Passaging time and colony formation efficiency of 5-10% after single cell plating without ROCKi were comparable to reset cells generated via inducible transgene expression. Cells continued to proliferate without differentiation in the presence of A83-01 (FIG. 7G) confirming independence from activin/nodal signalling, unlike previously described human PSC but consistent with mouse ESC. Furthermore, siRNA knockdown of TFCP2L1 or KLF4 significantly impaired colony formation (FIG. 7I-1), indicating functional dependency on ground state transcription factors. Continued passaging confirmed that the diploid karyotype was stable.

We conclude that the reset state can be generated by short-term expression of NANOG and KLF2 avoiding permanent genetic modification.

Discussion

The postulate that a self-renewing ground state similar to rodent ESC may pertain to primates remains contentious. Our findings indicate that anticipated ground state properties may be instated in human cells following short-term expression of NANOG and KLF2 transgenes. The resulting cells can readily be perpetuated in defined medium lacking either serum products or growth factors. Feeders support attachment and growth of reset cells as of conventional PSC, but are dispensable.

Reset human stem cells show global changes in DNA methylation and transcription suggestive of conversion to a more primitive state. They also display altered metabolism with increased mitochondrial respiration. This constellation of features distinguishes reset human cells from previously described embryo-derived or induced human PSC and aligns them closer to ground state mouse ESC. Most significantly, the unique transcription factor circuit essential for mouse ESC identity, self-renewal and pluripotency, is functionally operative in sustaining the reset human pluripotent state.

Recent claims of putative naive human PSC (Chan et al., 2013; Gafni et al., 2013; Ware et al., 2014) have employed culture media with an incoherent array of growth factors and inhibitors. The biological rationale for the media formulations is unclear as are the combinatorial molecular consequences. However, one possibility is that such compound conditions may select for propagation of heterogeneous cultures comprising cells co-habiting in different phases of pluripotency as described for mouse EpiSCs (Bernemann et al., 2011; Han et al., 2010; Tsakiridis et al., 2014). Lack of enrichment for naïve pluripotency factors and expression of mixed lineage markers (FIG. 5C,D) are consistent with such an explanation.

We focussed on simple conditions with no added growth factors, other than insulin and the cytokine LIF. We used a concentration (1.0 µM) of MEK inhibitor that ensures complete inhibition of the Erk pathway. Independence from Erk signalling is a hallmark property of rodent ground state cells in vitro and pre-implantation epiblast in vivo (Boroviak et al., 2014; Nichols and Smith, 2009; Ying et al., 2008) that is conserved in human pre-implantation epiblast (Roode et al., 2012).

In contrast the optimal concentration of GSK3 inhibition differs between mouse and human cells. This may reflect an altered balance between TCF3 repressor function and activation of canonical TCF/LEF factors, as delineated in rat ESC (Chen et al., 2013b). In addition, in mouse ESC GSK3 inhibition acts in large part through derepression of Esrrb (Martello et al., 2013) but ESRRB is poorly expressed in reset human PSC. Poor conservation of a genomic interval where NANOG, OCT4, SOX2 and TCF3 bind at the mouse Esrrb gene may underlie this lack of response to CH (FIG. 28). ESRRB is a potent self-renewal factor in mouse ESC (Festuccia et al., 2012; Martello et al., 2012), and its low expression may contribute to the limited ability of human cells to thrive in 2iL and explain the requirement for additional support. Gö6983 is a broad specificity PKC inhibitor found to facilitate mouse ESC self-renewal (Dutta et al., 2011).

Recently we showed that mutation of atypical PKC iota largely recapitulates this effect of Gö6983 (Leeb et al., 2014). Consistent with this, we found that knockdown of aPKC iota allows propagation of reset human cells in t2iL without Gö6983 (FIG. 29). The mechanism downstream of aPKC inhibition remains to be elucidated but it is tempting to speculate that it may inhibit differentiation by interfering with acquisition of epithelial polarity, an essential feature of post-implantation epiblast.

Rewired PSC cultured in t2iL+Gö consistently grow as small colonies in which cells are tightly packed. On transfer to FGF/KSR cells progressively flatten over several days and adopt typical human PSC appearance. They downregulate naïve markers and after 2-3 passages completely lose the ability to form colonies in t2iL+Gö. This process resembles mouse ESC to EpiSC differentiation in vitro and progression from pre- to post-implantation epiblast in vivo. Rodent ground state ESC are distinguished by, and dependent on, expression of a suite of transcription factors additional to OCT4, SOX2 and NANOG (Nichols and Smith, 2012). Each of these is individually dispensable for ESC self-renewal due to overlapping functions in a flexible circuitry (Dunn et al., 2014). They are all absent or very lowly expressed in EpiSC and conventional human PSC. In human reset cells, all are expressed apart from ESRRB (FIG. 7). The absence of ESRRB is anticipated to render the ground state circuitry more fragile. Severe compromise to self-renewal upon KLF4 or TFCP2L1 knockdown is consistent with this prediction and provides evidence that reset human PSC are functionally governed by the rewired ground state transcription factor circuit. Rescue of TFCP2L1 knock down cells by ESRRB provides further evidence for functional conservation with the mouse ESC ground state control system.

TFCP2L1 is a proven pivotal factor in mouse ES cell self-renewal that is barely expressed in any previously described human PSC but is both abundant and essential in our reset cells.

The present findings suggest that authentic ground state pluripotent stem cells may be attainable in human, lending support to the notion of a generic naive state of pluripotency in mammals. In human, the ground state transcription factor circuit appears in large part to be conserved but requires greater reinforcement to be stably propagated. Disposition to collapse reflect the transient nature of naive pluripotency in the embryo (Nichols and Smith, 2012). The imperative for developmental progression may be intrinsically stronger in primates which, unlike mouse and rat, have not evolved the facility for embryonic diapause (Nichols et al., 2001). Nonetheless, there may be scope to refine and further improve the culture conditions for human ground state PSC. The increased number and size of colonies obtained under conditions of transgene induction may point to this potential.

Comprehensive evaluation of the ground state hypothesis remains necessary, however. The reset cells described here might be considered a synthetic product of genetic intervention. Derivation of equivalent cells directly from human blastocysts is therefore a key future landmark. Formation of primary chimaeras, a powerful test of naive status and developmental potency in rodents, cannot be undertaken in human. However, the finding that reset cells can be consistently incorporated into the ICM/epiblast of mouse blastocysts distinguishes them from conventional human PSC or mouse EpiSC and is consistent with pre-implantation identity. Interestingly, upon further culture to mimic post-implantation mouse epiblast development (Bedzhov and Zernicka-Goetz, 2014) contribution of human cells was no longer detected.

These data are preliminary but may suggest that human cells are unable to adjust to the much faster rate and/or distinct morphogenetic organisation of mouse post-implantation epiblast development compared with human. As a valid alternative, contribution to same-species chimaeras could be explored in non-human primates. Perhaps the most important question, however, at least from a translational perspective, is whether rewiring transcriptional circuitry also erases epigenetic specifications. Human genetic variation notwithstanding, a naïve epigenome may be expected to confer increased consistency of both undifferentiated phenotype and differentiation behaviour. Reduced H3K9me3 and genome-wide DNA hypomethylation point to a reprogrammed and derestricted epigenome in reset cells, potentially comparable to the early human embryo (Reik and Kelsey, 2014). It will be of great interest to determine the precise functional impact of such widespread epigenome cleansing.

In summary, the present inventors have demonstrated that ground state pluripotency is a distinctive cell identity for human cells, which is analogous to authentic mouse embryonic stem cells. They show that the transcription factor circuitry that governs mouse embryonic stem cells can be activated in human cells and take executive control of global metabolic, epigenetic and transcriptome programmes.

The inventors have demonstrated reproducibility of their method in difference hPSCs and stability in long-term passaging with retention of normal karyotype for several reset lines. In fact the three reset cell lines used for transcriptome analyses had been passaged multiple times.

The inventors have shown that reset cells are not less pluripotent using 5 different assay systems.

These findings demonstrate feasibility of installing and propagating functional control circuitry for ground state pluripotency in human cells.

Example 2

Materials
FGF/KSR Medium:
DMEM/F12 basal medium supplemented with 20% KSR, 1 mM glutamine, 1% non-essential amino acids, 0.1 mM 2ME and 10 ng/ml FGF2
Resetting Medium & Abbreviations;
PDL-HDACi comprises mTeSR™-E6 basal medium (Stem Cell Technologies) supplemented with 1 µM PD0325901, human LIF (10 ng/ml, prepared in house) and a
HDAC inhibitor such as valproic acid sodium salt (VPC, 0.5-1 mM, Sigma,) or sodium butyrate (SB, 0.5-1 mM, Sigma).
Optionally a Wnt pathway inhibitor such as XAV939 (2 µM) may be included, constituting PDXL. In the presence of XAV939 colony yield may be higher for some cell lines but colonies are also more heterogeneous.
Thus PDXL contains mTeSR™-E6 basal medium (Stem cell Technologies) supplemented with 1 µM PD0325901, 2 µM XAV939, human LIF (prepared in house).
PDXL-HDACi is either:
PDXL-VPC: PDXL medium with valproic acid sodium salt (Sigma, 0.5-1 mM).
PDXL-SB: PDXL medium with Sodium butyrate (Sigma, 0.5-1 mM).
Resetting is preferably performed in incubators at 5% oxygen.
Naïve Maintenance Medium:
2iLGö-Y contains N2B27 basal medium supplemented with 250 µM L-ascorbic acid-2-phosphate magnesium Acid (Sigma), 1 µM PD0325901, 1 mM Chiron, 2.5 µM Gö6983 (2.5 uM, Sigma), human LIF and 10 µM ROCK inhibitor Y27632.
The ROCK inhibitor is optional for continued culture and may be withdrawn or applied only for 24 hours after passaging.
Results
Resetting to Ground State Pluripotency without Use of Transgenes
Human ES cells Shef6 and H9, which carry the EOS reporter [Hotta], were plated at a density of 50,000 to 100,000 cells per well of a six well tissue culture dish in KSR/FGF medium supplemented with 10 µM ROCK inhibitor (Y-27632). The day after medium was replaced with resetting medium (PDL-HDACi or PDXL-HDACi) for the following three days. Thereafter the cells were maintained in naïve maintenance medium, T2iLGö-FROCKi (FIG. 30).

Figure 36:
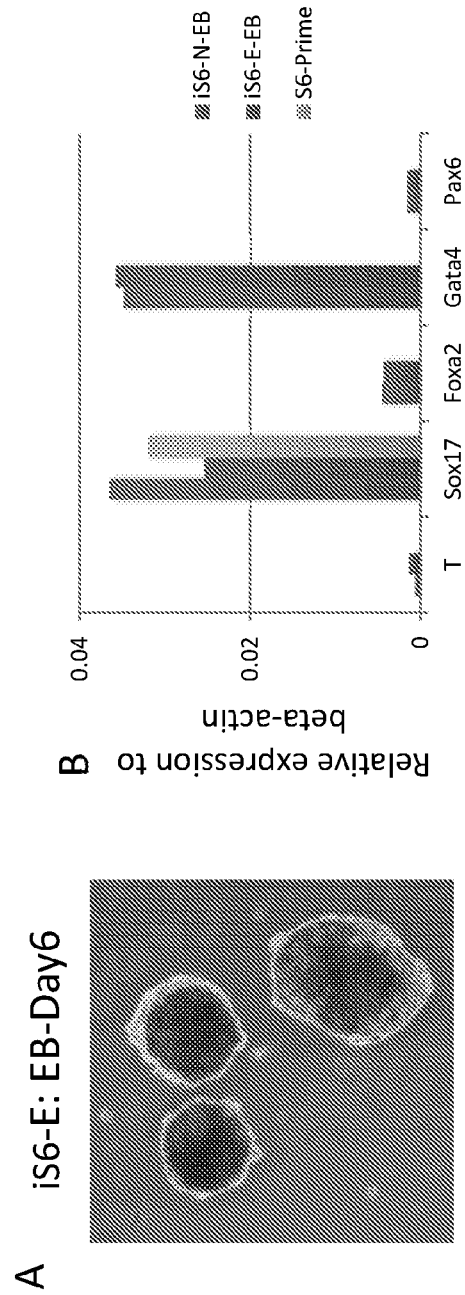

EOS reporter contains a GFPIresPuro cassette driven by LTR of early transposon and a trimer of mouse Oct4 distal enhancer. The EOS reporter in majority of conventional human ES cells is expressed at low to undetectable level by microscope. More than 80 percent of cells do show low to moderate GFP expression by flow cytometry analysis (FACS) (FIG. 31). The resetting medium induced vast cell death and differentiation three days after. The dome shaped GFP positive colonies appears around Day5 to Day7 and peaked after day10 to day 12 (FIG. 32, FIG. 33, FIG. 34). The colonies can then be passaged in bulk or picked singly using TrypLE™ express. Puromycin selection is applied for one or two passages to exclude differentiated cells if needed. The reset cells expressed elevated naïve state markers, TFCP2L1 and DPPA3 from Day7 during resetting (FIG. 35). Two pools, iS6-N and iS6-E, have been maintained over 15 passages and are karyotypically normal by G-band analysis. They form embryoid body readily in low adhesive 96 well plates and up-regulate differentiation markers (FIG. 36).

Figure 37:
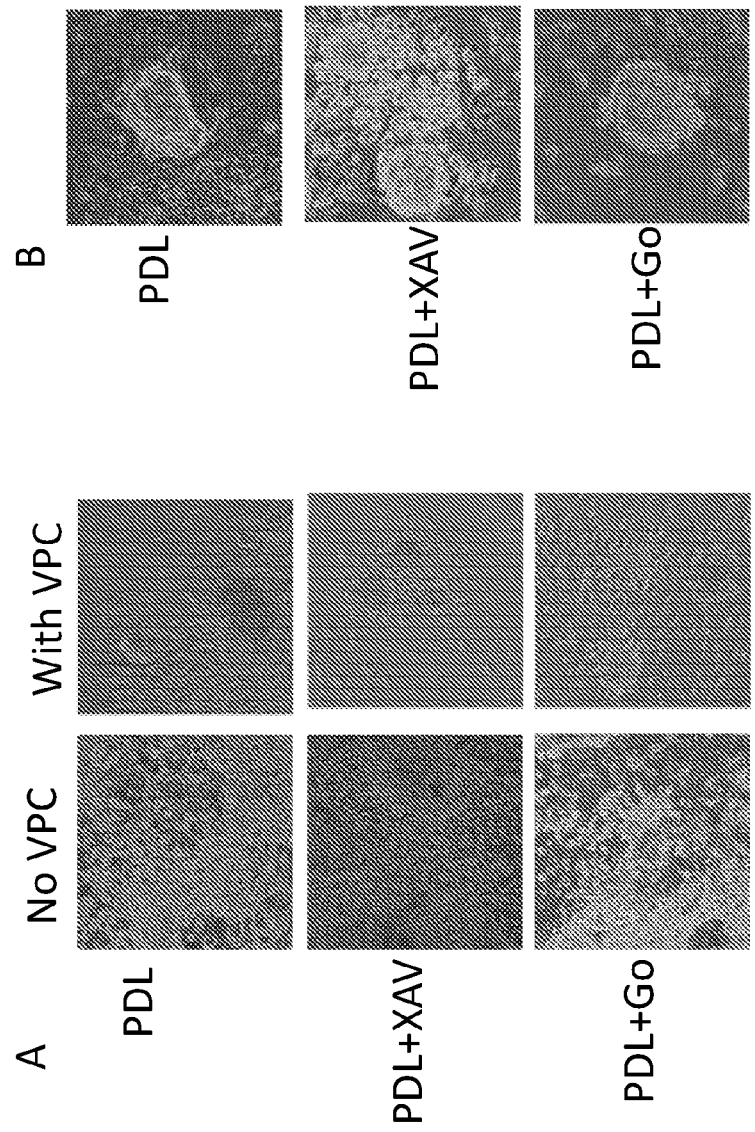

Human naïve cells form compact dome shaped colonies, which can be identified and picked based on morphology. Therefore, EOS reporter is not necessary to identify, pick and expand reset cells (FIG. 37).

Additionally reset naïve cells can also be isolated based on their expression of surface markers such as Tra1-60, Tra1-81, E-cadherin, CD365 or CD53.

Conventional human ES cell and iPS cell lines are heterogeneous. To obtain robust resetting efficiency the conditions may need to be adjusted, especially the concentration and duration of HDAC inhibitor treatment. Addition of XAV939 in transgene-free resetting medium is optional but for some human ES cell lines could significantly increase resetting efficiency.

PKC inhibition is not essential but can be added to the resetting medium. FGF receptor inhibition (PD17) may be applied in addition to MEK inhibition. E6-based medium generally allows fast and robust resetting, but N2B27 based medium also works, although with delayed kinetics.

This protocol can be applied to pluripotent cell lines or primary embryonic cultures from other mammalian species.

Example 3

Establishing Ground State Cultures Directly from the Embryo

Reset cells can be derived directly from primate, rodent or other mammalian embryos.

For derivation from pre-implantation stages, embryos developed in vitro or in utero are cultured either intact, or after isolation of the inner cell mass (ICM) by microdissection or immunosurgery and optional dissociation into single cells. Initial culture is in N2B27 or equivalent basal media with t2iL or PDL plus ROCK inhibitor (10 µM) and with or without ascorbic acid (250 µM, Sigma). Gö may be added at 2-4 µM from the beginning or only after passaging. Colonies with typical tightly clustered morphology of ground state cells may be distinct in primary outgrowths or only emerge after passaging. Colonies are picked and expanded in ground state maintenance medium as above. Levels of GSK3 and PKC inhibition may have to be adjusted to achieve the optimum for different species.

For derivation from late blastocysts, peri-implantation embryos or post-implantation epiblast, dissected and/or dissociated epiblast cells are initially cultured in resetting medium with PDL-HDACi, XAV, and optionally PKC inhibitor. They are then transferred, typically after two or three days, into ground state maintenance medium. Colonies are picked and expanded in ground state medium as above. Derivations are preferably performed in incubators at 5% oxygen.

The following Example demonstrates how appropriate culture conditions can be used to allow direct expansion of human pre-implantation epiblast into naïve stem cell lines.

a) Materials and Methods

Embryo Manipulation

Supernumerary frozen human embryos were generously donated with informed consent under HFEA licence R0178. Embryos were thawed using embryo thawing kit (FertiPro) and cultured in drops of pre-equilibrated embryo media (Origio); either EmbryoAssist for 1-8 cell stage (Day 0-2), or BlastAssist for 8 cell to blastocyst (Day 3-6) under embryo-tested mineral oil (Sigma). They were monitored daily and transferred to fresh medium, as appropriate for developmental stage. Expanded blastocysts (Day 6) were subjected to immunosurgery (13, 23) to isolate inner cell masses (ICMs) using anti-human serum (Sigma). ICMs were treated with Accutase (Sigma or Gibco) for 5-10 minutes, and transferred to a droplet of medium for mechanical separation using a finely-drawn Pasteur pipette. Individual ICM cells were then scattered onto mitotically-inactivated (irradiated) murine embryonic fibroblasts (MEFs).

Naïve Stem Cell Culture

Cells were propagated in modified N2B27 medium supplemented with PD0325901 (1 µM, prepared in house), CHIR99021 (1 µM, prepared in house), Gö6983 (2.5 µM, Sigma-Aldrich), Rho-associated kinase inhibitor (ROCKi, Y-27632)(10 µM, Calbiochem), human LIF (10 ng/ml, prepared in house) and ascorbic acid (250 µM, Sigma). This medium is referred to as t2iLGöY.

Modified N2B27 medium (1 L) comprised 490 mL DMEM/F12 (Life Technologies), 490 mL Neurobasal (Life Technologies), 10 mL B27 (Life Technologies), 5 mL N2 (prepared in house), 10 µg/mL insulin (Sigma), 2 mM L-glutamine (Life Technologies) and 0.1 mM 2-mercaptoethanol (Sigma). N2 contains 100 µg/ml Apo-transferrin (eBioscience, ABC2553), 3 µM Sodium selenite (Sigma), 1.6 mg/mL Putrescine (Sigma) and 2 µg/mL Progesterone (Sigma) in DMEM/F12 (Life technology).

Cells were cultured on irradiated MEFs. Primary colonies and nascent cell lines were passaged manually as described above for ICMs after transferring colonies to micro-drops. Established naïve stem cells were passaged either manually with Accutase (Life Technologies) dissociation or as a pool using TrypLE™ Express (Life technology. 12605). Cells were cultured in 5% oxygen, 7% carbon dioxide in a humidified incubator at 37° C.

Conversion to Primed Pluripotency

HNES cells were seeded on MEFs in t2iLGöY medium for 24 hours then transferred into FGF/KSR medium for 7-10 days before passaging with TrypLE™ Express. Y27632 (10 µM) was added for the first passage. Thereafter cells were routinely passaged as clusters using Collagenase/Dispase (Roche). FGF/KSR medium comprised 20% KSR (Invitrogen), 1x nonessential amino acids (NEAA) (Invitrogen), 2 mM L-glutamine (Invitrogen), 100 µM 2-mercaptoethanol (Sigma), 10 ng/mL FGF2 (prepared in-house) and DMEM/F-12 basal medium (Sigma-Aldrich). Established HNES-primed cultures can also be maintained in mTeSR™ 1 or E8 medium (StemCell Technologies) on Matrigel coated tissue culture plates.

In Vitro Differentiation

Human naïve stem cells or primed derivatives were dissociated with TrypLE™ Express and deposited in Prime-Surface 96V cell plates (Sumitomo Bakelite MS-9096V) at a density of 4000-5000 cells per well in differentiation medium containing either 20% FBS or 20% KSR.

ROCK inhibitor (Y27632; 10 µM) was added during the first 24 hours of aggregation. At day 7 aggregates were plated on gelatin-coated tissue culture plastic in FBS differentiation medium for attachment and outgrowth.

Sample Preparation for Transcriptome Analyses

Total RNA was prepared after depletion of feeder cells by culturing on gelatin-coated dishes for 40 minutes and harvesting non-attached cells for TRIzol extraction.

b) Results

In this Example we cultured human embryo derivations of PSC using serum-free N2B27 medium containing LIF and t2i plus the pan-PKC inhibitor Gö6983.

To safeguard viability of precious embryo cells, we added ascorbic acid and ROCK inhibitor (Y-27632), constituting t2iLGöY. Cultures were maintained on fibroblast feeders in 5% $O_2$.

We used immunosurgery (Solter & Knowles, PNAS 1975; 72(12):5099-102) to isolate ICMs from blastocysts 6 days post-fertilisation. Following accutase-assisted dissociation, single cells or doublets were distributed on feeders in t2iLGöY. Around half of the plated ICM cells formed compact colonies within 4-5 days (FIG. 38A-I), similar to mouse ES cell primary colony formation. Colonies were picked manually, dissociated and pooled. Replated cells proliferated and could be expanded by passaging every 4-5 days (FIG. 38J). Four cell lines were established from different embryos (Table A below) and termed human naïve epiblast stem (HNES) cells.

| | A. Derivations of naïve epiblast stem cell lines | | | | |
|---|---|---|---|---|---|
| Expt | Embryos surviving thaw | Blastocysts^ | Dissociated ICMs | Cell lines | Cumulative passages |
| 1 | 24 | 4 | 1 | HNES1 | P30 |
| 2 | 9 | 4 | 2 | HNES2 | P14 |
| | | | | HNES3 | P29 |
| 3 | 20 | 4 | 4 | HNES4 † | P11 |
| 4 | 5 | 2 | 1 | —* | |
| Total | 58 | 14 | 8 | 4 | |

^Embryos cavitated by day 6.
† Primary colonies lost in three cases associated with incubator humidity failure
*Primary colonies emerged but failure to expand after 5 passages.

Metaphase chromosomes were prepared from the first three lines. Two lines displayed both diploid and aberrant karyotypes while one showed 46 XY karyotype that was stable after further passaging with no abnormalities detected by G-banding or array CGH (FIG. 38K and Table B below). This line, HNES-1, is characterised further below.

| B. Chromosome analysis of naïve epiblast stem cell lines | | |
|---|---|---|
| Cell line | Passage | Karyotype |
| HNES1* | P11 | 46, XY (20/20) |
| | P21 | 46, XY (11/11) |
| HNES2 | P6 | 46, XY (10/30); tetraploid-like (20/30) |
| HNES3 | P18 | 46, XX (6/20); 47, XX (14/20) |

*HNES1 cells were also examined by high resolution array CGH after 14 passages in t2iLGöY and a further 8 passages in KSR/FGF. This analysis confirmed a 46, XY chromosome complement with no detectable abnormalities.

Comparison of markers between HNES cells and reset cells generated from conventional PSC following expression of KLF2/NANOG showed similar elevated transcript levels for NANOG and expression of diagnostic naïve pluripotency markers KLF4, TFCP2L1 and DPPA3 (FIG. 38L). Immunostaining confirmed presence of NANOG, KLF4 and TFCP2L1 proteins along with OCT4 (FIG. 38M).

Figure 39A:
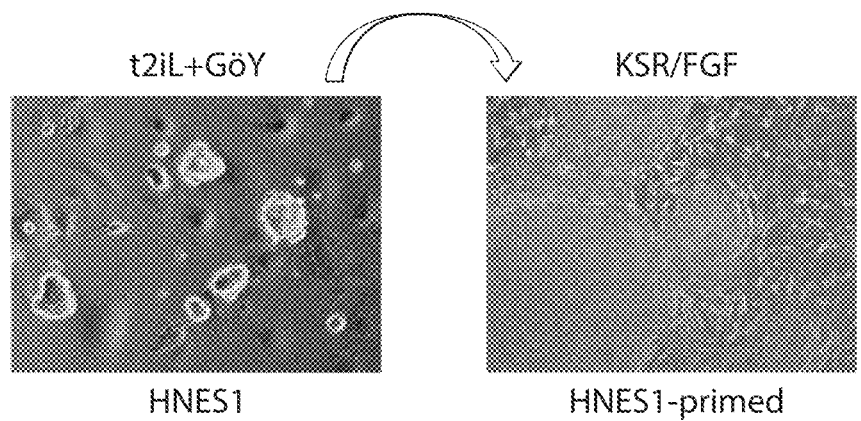
Figure 39B:
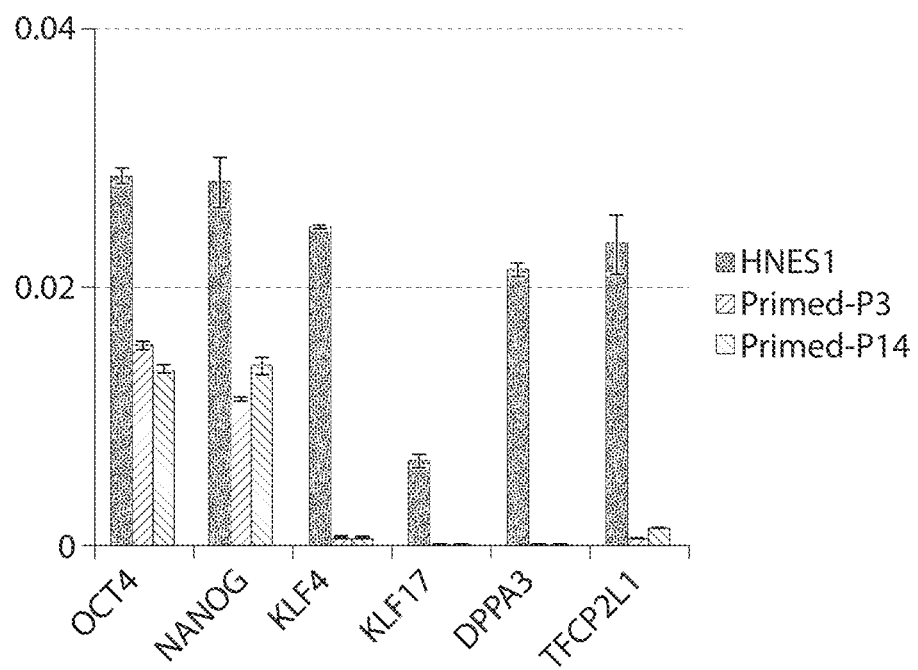

We transferred HNES cells to conventional PSC culture medium containing KSR/FGF and lacking inhibitors. After one passage the domed colonies of HNES cells assumed flattened epithelial morphology and after two passages stabilised in conventional PSC appearance. OCT4 and NANOG expression was reduced and naïve markers extinguished (FIG. 39A, 39B).

Figure 39C:
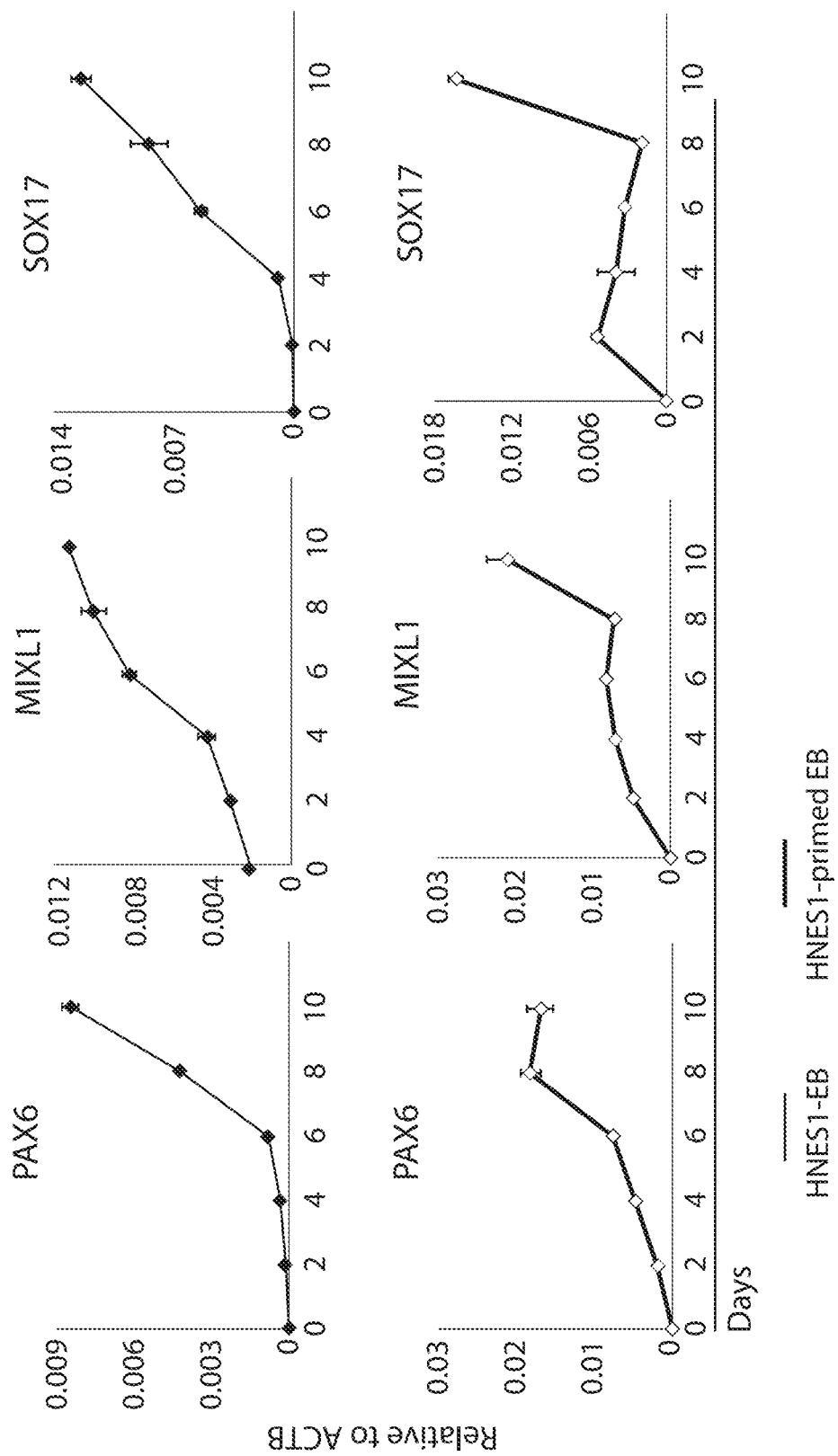
Figure 39D:
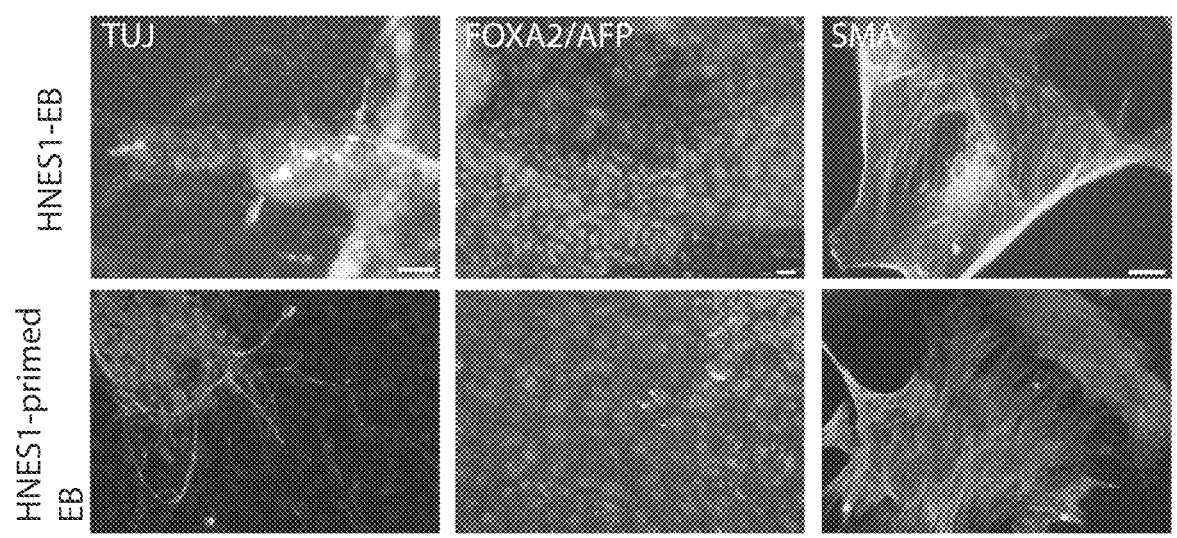

We assessed whether HNES cells can undergo multilineage differentiation via embryoid body formation. We formed aggregates both directly from HNES cells and from HNESprimed cells after culture in KSR/FGF. In both cases we detected up-regulation of early lineage markers, PAX6, MIXL1 and SOX17 (FIG. 39C). Embryoid body outgrowths displayed TuJ1-positive neuronal, FOXA2/AFP double positive endoderm, and smooth muscle actin positive cells (FIG. 39D).

Primed PSC rely on anaerobic glycolysis with very low mitochondrial respiration capacity (Zhou et al., 2012). In contrast, reset PSC have active mitochondria and correspondingly reduced glucose dependence. We evaluated the capacity of HNES cells to form colonies in the presence of the glycolysis inhibitor 2-deoxyglucose. Undifferentiated HNES cells readily formed colonies while HNES-primed cells did not survive (not shown). HNES cells also stained intensely with MitoProbe™ DilC1, reflecting mitochondrial membrane potential (not shown).

Measurement of oxygen consumption rate by extracellular flux analysis confirmed that HNES cells have at least two fold higher respiratory capacity than primed cells (not shown).

We employed RNA-seq to obtain whole transcriptome profiles from replicate cultures of each of the three independent HNES lines. These data were compared to reset and conventional human PSC datasets reported above and to a wider panel of H9 and H1 data from the public domain. HNES cells feature a transcriptome distinct from other PSC and consistent with the reset state (FIG. 40A). They show consistent expression of naïve pluripotency factors, denoting naïve identity. In contrast, conventional PSC exhibit wider variation in expression profiles with, for example, sporadic activation of NANOG, ZFP42 (REX1) and TFCP2L1. HNES cells also express a restricted complement of lineage markers compared with conventional PSC. We performed principal component analysis, additionally incorporating published data on human ICM cells generated by single cell RNAseq and corresponding conventional PSC single cell data (FIG. 40B). PC1 primarily discriminates between single-cell and bulk RNA-seq samples, suggesting a major influence of sequencing protocol. Indeed, numerous genes that are detected in the other studies yield zero scores in the Yan dataset, in line with known detection limitations of single cell RNAseq (Kharchenko et al., Nat Methods. 2014; 11(7):740-2. The biological replicates of the three HNES cells cluster together along with reset H9 cells. PC2 places HNES cells in relative proximity to the ICM cells and well separated from other PSC. The degree of alignment on PC2 between HNES cells and embryo cells appears reasonable, considering that the early ICM cells analysed likely precede naïve epiblast.

Mouse and human ICM cells are characterised by global DNA hypomethylation (Guo et al., 2014; Smith et al., 2014). This epigenomic feature is shared with naïve ES cells (Ficz et al., 2013; Habibi et al., 2013; Leitch et al., 2013) and reset human PSC (see discussion hereinbefore). HNES cells show down-regulation of de novo methyltransferase DNMT3B and appreciable expression of TET1 (FIG. 40C). Immunostaining for 5-methylcytosine (5mC) is fainter in HNES cell nuclei compared to HNES-primed cells. Whole genome bisulfite sequencing (BS-seq) confirmed genome-wide hypomethylation in HNES cells, similar to levels of 30-40% observed in the human ICM (Guo et al., 2014) and in contrast to >70% CpG methylation in conventional PSC and HNES-primed cells (FIG. 40D, E).

c) Discussion

We have shown that after dissociation of the ICM to separate epiblast and primitive endoderm, stem cell colonies grow up directly in the presence of inhibitors of MAPK/Erk, GSK3 and PKC. Resulting HNES cell lines can be propagated by disaggregation to single cells and may retain chromosomal integrity over many passages. Molecular markers, global transcriptome, metabolic properties, and DNA hypomethylation features align HNES cells with reset PSC and in proximity to mouse ES cells and human ICM.

REFERENCES

Adewumi, O., Aflatoonian, B., Ahrlund-Richter, L., Amit, M., Andrews, P. W., Beighton, G., Bello, P. A., Benvenisty, N., Berry, L. S., Bevan, S., et al. (2007). Characterization of human embryonic stem cell lines by the International Stem Cell Initiative. Nat Biotechnol 25, 803-816.

Aflatoonian, B., Ruban, L., Shamsuddin, S., Baker, D., Andrews, P., and Moore, H. (2010). Generation of Sheffield (Shef) human embryonic stem cell lines using a microdrop culture system. In Vitro Cell Dev Biol Anim 46, 236-241.

Amit, M., Carpenter, M. K., Inokuma, M. S., Chiu, C. P., Harris, C. P., Waknitz, M. A., Itskovitz-Eldor, J., and Thomson, J. A. (2000). Clonally derived human embryonic stem cell lines maintain pluripotency and proliferative potential for prolonged periods of culture. Dev Biol 227, 271-278.

Amps, K., Andrews, P. W., Anyfantis, G., Armstrong, L., Avery, S., Baharvand, H., Baker, J., Baker, D., Munoz, M. B., Beil, S., et al. (2011). Screening ethnically diverse human embryonic stem cells identifies a chromosome 20 minimal amplicon conferring growth advantage. Nat Biotechnol 29, 1132-1144.

Anders, S., and Huber, W. (2010). Differential expression analysis for sequence count data. Genome Biol 11, R106.

Anders, S., Pyl, P. T., and Huber, W. (2014). HTSeq—A Python framework to work with high-throughput sequencing data. bioRxiv.

Ang, Y.-S., Tsai, S.-Y., Lee, D.-F., Monk, J., Su, J., Ratnakumar, K., Ding, J., Ge, Y., Darr, H., Chang, B., et al. (2011). Wdr5 Mediates Self-Renewal and Reprogramming via the Embryonic Stem Cell Core Transcriptional Network. Cell 145, 183-197.

Bedzhov, I., and Zernicka-Goetz, M. (2014). Self-organizing properties of mouse pluripotent cells initiate morphogenesis upon implantation. Cell 156, 1032-1044.

Bernemann, C., Greber, B., Ko, K., Sterneckert, J., Han, D. W., Arauzo-Bravo, M. J., and Scholer, H. R. (2011). Distinct developmental ground states of epiblast stem cell lines determine different pluripotency features. Stem Cells 29, 1496-1503.

Betschinger, J., Nichols, J., Dietmann, S., Corrin, Philip D., Paddison, Patrick J., and Smith, A. (2013). Exit from Pluripotency Is Gated by Intracellular Redistribution of the bHLH Transcription Factor Tfe3. Cell 153, 335-347.

Boroviak, T., Loos, R., Bertone, P., Smith, A., and Nichols, J. (2014). The ability of inner-cell-mass cells to self-renew as embryonic stem cells is acquired following epiblast specification. Nat Cell Biol 16, 516-528.

Brons, I. G., Smithers, L. E., Trotter, M. W., Rugg-Gunn, P., Sun, B., Chuva de Sousa Lopes, S. M., Howlett, S. K., Clarkson, A., Ahrlund-Richter, L., Pedersen, R. A., et al. (2007). Derivation of pluripotent epiblast stem cells from mammalian embryos. Nature 448, 191-195.

Buehr, M., Meek, S., Blair, K., Yang, J., Ure, J., Silva, J., McLay, R., Hall, J., Ying, Q. L., and Smith, A. (2008). Capture of authentic embryonic stem cells from rat blastocysts. Cell 135, 1287-1298.

Burdon, T., Stacey, C., Chambers, I., Nichols, J., and Smith, A. (1999). Suppression of SHP-2 and ERK signalling promotes self-renewal of mouse embryonic stem cells. Dev Biol 210, 30-43.

Carvalho, B. S., and Irizarry, R. A. (2010). A framework for oligonucleotide microarray preprocessing. Bioinformatics 26, 2363-2367.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. Nat Biotechnol 27, 275-280.

Chan, Y. S., Goke, J., Ng, J. H., Lu, X., Gonzales, K. A., Tan, C. P., Tng, W. Q., Hong, Z. Z., Lim, Y. S., and Ng, H. H. (2013). Induction of a Human Pluripotent State with Distinct Regulatory Circuitry that Resembles Preimplantation Epiblast. Cell Stem Cell 13, 663-675.

Chen, X., Xu, H., Yuan, P., Fang, F., Huss, M., Vega, V. B., Wong, E., Orlov, Y. L., Zhang, W., Jiang, J., et al. (2008). Integration of external signaling pathways with the core transcriptional network in embryonic stem cells. Cell 133, 1106-1117.

Chen, Y., Blair, K., and Smith, A. (2013a). Robust Self-Renewal of Rat Embryonic Stem Cells Requires Fine-Tuning of Glycogen Synthase Kinase-3 Inhibition. Stem Cell Reports 1, 209-217.

Chen, Y., Blair, K., and Smith, A. (2013b). Robust Self-Renewal of Rat Embryonic Stem Cells Requires Fine-Tuning of Glycogen Synthase Kinase-3 Inhibition. Stem Cell Reports.

Chia, N. Y., Chan, Y. S., Feng, B., Lu, X., Orlov, Y. L., Moreau, D., Kumar, P., Yang, L., Jiang, J., Lau, M. S., et al. (2010). A genome-wide RNAi screen reveals determinants of human embryonic stem cell identity. Nature 468, 316-320.

De Los Angeles, A., Loh, Y. H., Tesar, P. J., and Daley, G. Q. (2012). Accessing naive human pluripotency. Curr Opin Genet Dev 22, 272-282.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Dunn, S. J., Martello, G., Yordanov, B., Emmott, S., and Smith, A. G. (2014). Defining an essential transcription factor program for naïve pluripotency. Science 344, 1156-1160.

Dutta, D., Ray, S., Home, P., Larson, M., Wolfe, M. W., and Paul, S. (2011). Self-renewal versus lineage commitment of embryonic stem cells: protein kinase C signaling shifts the balance. Stem Cells 29, 618-628.

Festuccia, N., Osorno, R., Halbritter, F., Karwacki-Neisius, V., Navarro, P., Colby, D., Wong, F., Yates, A., Tomlinson, Simon R., and Chambers, I. (2012). Esrrb Is a Direct Nanog Target Gene that Can Substitute for Nanog Function in Pluripotent Cells. Cell Stem Cell 11, 477-490.

Ficz, G., Hore, T. A., Santos, F., Lee, H. J., Dean, W., Arand, J., Krueger, F., Oxley, D., Paul, Y. L., Walter, J., et al. (2013). FGF signaling inhibition in ESCs drives rapid genome-wide demethylation to the epigenetic ground state of pluripotency. Cell Stem Cell 13, 351-359.

Flicek, P., Amode, M. R., Barrell, D., Beal, K., Billis, K., Brent, S., Carvalho-Silva, D., Clapham, P., Coates, G., Fitzgerald, S., et al. (2014). Ensembl 2014. Nucleic Acids Res 42, D749-755.

Gafni, O., Weinberger, L., Mansour, A. A., Manor, Y. S., Chomsky, E., Ben-Yosef, D., Kalma, Y., Viukov, S., Maza, I., Zviran, A., et al. (2013). Derivation of novel human ground state naive pluripotent stem cells. Nature 504, 282-286.

Gschwendt M et al *FEBS Lett.* 1996 Aug. 26; 392(2):77-80

Guo, G., Yang, J., Nichols, J., Hall, J. S., Eyres, I., Mansfield, W., and Smith, A. (2009). Klf4 reverts developmentally programmed restriction of ground state pluripotency. Development 136, 1063-1069.

Guo, H., Zhu, P., Yan, L., Li, R., Hu, B., Lian, Y., Yan, J., Ren, X., Lin, S., Li, J., et al. (2014). The DNA methylation landscape of human early embryos. Nature; 511 (7511):606-10.

Habibi, E., Brinkman, A. B., Arand, J., Kroeze, L. I., Kerstens, H. H., Matarese, F., Lepikhov, K., Gut, M., Brun-Heath, I., Hubner, N. C., et al. (2013). Whole-genome bisulfite sequencing of two distinct interconvertible DNA methylomes of mouse embryonic stem cells. Cell Stem Cell 13, 360-369.

Hall, J., Guo, G., Wray, J., Eyres, I., Nichols, J., Grotewold, L., Morfopoulou, S., Humphreys, P., Mansfield, W., Walker, R., et al. (2009). Oct4 and LIF/Stat3 additively induce Kruppel factors to sustain embryonic stem cell self-renewal. Cell Stem Cell 5, 597-609.

Han, D. W., Tapia, N., Joo, J. Y., Greber, B., Araúzo-Bravo, M. J., Bernemann, C., Ko, K., Wu, G., Stehling, M., Do, J. T., et al. (2010). Epiblast Stem Cell Subpopulations Represent Mouse Embryos of Distinct Pregastrulation Stages. Cell 143, 617-627.

Hanna, J., Cheng, A. W., Saha, K., Kim, J., Lengner, C. J., Soldner, F., Cassady, J. P., Muffat, J., Carey, B. W., and Jaenisch, R. (2010). Human embryonic stem cells with biological and epigenetic characteristics similar to those of mouse ESCs. Proc Natl Acad Sci USA 107, 9222-9227.

Hanna, J., Markoulaki, S., Mitalipova, M., Cheng, A. W., Cassady, J. P., Staerk, J., Carey, B. W., Lengner, C. J., Foreman, R., Love, J., et al. (2009). Metastable pluripotent states in NOD-mouse-derived ESCs. Cell Stem Cell 4, 513-524.

Harrow, J., Frankish, A., Gonzalez, J. M., Tapanari, E., Diekhans, M., Kokocinski, F., Aken, B. L., Barrell, D., Zadissa, A., Searle, S., et al. (2012). GENCODE: the reference human genome annotation for The ENCODE Project. Genome Res 22, 1760-1774.

Hotta, A., Cheung, A. Y., Farra, N., Garcha, K., Chang, W. Y., Pasceri, P., Stanford, W. L., and Ellis, J. (2009). EOS lentiviral vector selection system for human induced pluripotent stem cells. Nat Protoc 4, 1828-1844.

Hotta A et al. Nat Methods. 2009 May; 6(5): 370-6. Isolation of human iPS cells using EOS lentiviral vectors to select for pluripotency.

Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics 4, 249-264.

Ivanova, N., Dobrin, R., Lu, R., Kotenko, I., Levorse, J., DeCoste, C., Schafer, X., Lun, Y., and Lemischka, I. R. (2006). Dissecting self-renewal in stem cells with RNA interference. Nature 442, 533-538.

Klimanskaya, I., Chung, Y., Becker, S., Lu, S. J., and Lanza, R., Human embryonic stem cell lines derived from single blastomeres, (2006). Nature 444, 481-485

Kojima, Y., Kaufman-Francis, K., Studdert, Joshua B., Steiner, Kirsten A., Power, Melinda D., Loebel, David A. F., Jones, V., Hor, A., de Alencastro, G., Logan, Grant J., et al. (2014). The Transcriptional and Functional Properties of Mouse Epiblast Stem Cells Resemble the Anterior Primitive Streak. Cell Stem Cell 14, 107-120.

Kroon, E., Martinson, L. A., Kadoya, K., Bang, A. G., Kelly, O. G., Eliazer, S., Young, H., Richardson, M., Smart, N. G., Cunningham, J., et al. (2008). Pancreatic endoderm derived from human embryonic stem cells generates glucose-responsive insulin-secreting cells in vivo. Nat Biotechnol 26, 443-452.

Leeb, M., Dietmann, S., Paramor, M., Niwa, H., and Smith, A. (2014). Genetic Exploration of the Exit from Self-Renewal Using Haploid Embryonic Stem Cells. Cell Stem Cell 14, 385-393.

Leitch, H. G., McEwen, K. R., Turp, A., Encheva, V., Carroll, T., Grabole, N., Mansfield, W., Nashun, B., Knezovich, J. G., Smith, A., et al. (2013). Naive pluripotency is associated with global DNA hypomethylation. Nat Struct Mol Biol 20, 311-316.

Li, P., Tong, C., Mehrian-Shai, R., Jia, L., Wu, N., Yan, Y., Maxson, R. E., Schulze, E. N., Song, H., Hsieh, C. L., et al. (2008). Germline competent embryonic stem cells derived from rat blastocysts. Cell 135, 1299-1310.

Marson, A., Levine, S. S., Cole, M. F., Frampton, G. M., Brambrink, T., Johnstone, S., Guenther, M. G., Johnston, W. K., Wernig, M., Newman, J., et al. (2008). Connecting microRNA genes to the core transcriptional regulatory circuitry of embryonic stem cells. Cell 134, 521-533.

Martello, G., Bertone, P., and Smith, A. (2013). Identification of the Missing Pluripotency Mediator Downstream of Leukaemia Inhibitory Factor. EMBO J In press.

Martello, G., Sugimoto, T., Diamanti, E., Joshi, A., Hannah, R., Ohtsuka, S., Gottgens, B., Niwa, H., and Smith, A. (2012). Esrrb is a pivotal target of the Gsk3/Tcf3 axis regulating embryonic stem cell self-renewal. Cell Stem Cell 11, 491-504.

Meek, S., Wei, J., Sutherland, L., Nilges, B., Buehr, M., Tomlinson, S. R., Thomson, A. J., and Burdon, T. (2013). Tuning of beta-catenin Activity is Required to Stabilise Self-renewal of Rat Embryonic Stem Cells. Stem Cells 31, 2104-2115.

Moretti, A., Bellin, M., Jung, C. B., Thies, T. M., Takashima, Y., Bernshausen, A., Schiemann, M., Fischer, S., Moosmang, S., Smith, A. G., et al. (2010). Mouse and human induced pluripotent stem cells as a source for multipotent Isl1+ cardiovascular progenitors. FASEB J 24, 700-711.

Nakagawa, M., Taniguchi, Y., Senda, S., Takizawa, N., Ichisaka, T., Asano, K., Morizane, A., Doi, D., Takahashi, J., Nishizawa, M., et al. (2014). A novel efficient feeder-free culture system for the derivation of human induced pluripotent stem cells. Sci Rep 4, 3594.

Neri, F., Krepelova, A., Incarnato, D., Maldotti, M., Parlato, C., Galvagni, F., Matarese, F., Stunnenberg, Hendrik G., and Oliviero, S. (2013). Dnmt3L Antagonizes DNA Methylation at Bivalent Promoters and Favors DNA Methylation at Gene Bodies in ESCs. Cell 155, 121-134.

Nichols, J., Chambers, I., Taga, T., and Smith, A. (2001). Physiological rationale for responsiveness of mouse embryonic stem cells to gp130 cytokines. Development 128, 2333-2339.

Nichols, J., and Smith, A. (2009). Naive and primed pluripotent states. Cell Stem Cell 4, 487-492.

Nichols, J., and Smith, A. (2012). Pluripotency in the embryo and in culture. Cold Spring Harbor Perspectives in Biology 4, a008128.

Niwa, H. (2007). How is pluripotency determined and maintained? Development 134, 635-646.

Niwa, H., Ogawa, K., Shimosato, D., and Adachi, K. (2009). A parallel circuit of LIF signalling pathways maintains pluripotency of mouse ES cells. Nature 460, 118-122.

Reik, W., and Kelsey, G. (2014). Epigenetics: Cellular memory erased in human embryos. Nature *advance online publication*.

Reubinoff, B. E., Pera, M. F., Fong, C. Y., Trounson, A., and Bongso, A. (2000). Embryonic stem cell lines from human blastocysts: somatic differentiation in vitro. Nat Biotechnol 18, 399-404.

Roode, M., Blair, K., Snell, P., Elder, K., Marchant, S., Smith, A., and Nichols, J. (2012). Human hypoblast formation is not dependent on FGF signalling. Dev Biol 361, 358-363.

Rossant, J. (2008). Stem cells and early lineage development. Cell 132, 527-531.

Silva, J., Nichols, J., Theunissen, T. W., Guo, G., van Oosten, A. L., Barrandon, O., Wray, J., Yamanaka, S., Chambers, I., and Smith, A. (2009). Nanog is the gateway to the pluripotent ground state. Cell 138, 722-737.

Silva, S. S., Rowntree, R. K., Mekhoubad, S., and Lee, J. T. (2008). X-chromosome inactivation and epigenetic fluidity in human embryonic stem cells. Proc Natl Acad Sci USA 105, 4820-4825.

Smith, A. G. (2001). Embryo-derived stem cells: of mice and men. Ann Rev Cell Dev Biol 17, 435-462.

Smith, A. G., Heath, J. K., Donaldson, D. D., Wong, G. G., Moreau, J., Stahl, M., and Rogers, D. (1988). Inhibition of pluripotential embryonic stem cell differentiation by purified polypeptides. Nature 336, 688-690.

Smith, Z. D., Chan, M. M., Humm, K. C., Karnik, R., Mekhoubad, S., Regev, A., Eggan, K., and Meissner, A. (2014). DNA methylation dynamics of the human preimplantation embryo. Nature *advance online publication*.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Tesar, P. J., Chenoweth, J. G., Brook, F. A., Davies, T. J., Evans, E. P., Mack, D. L., Gardner, R. L., and McKay, R. D. (2007). New cell lines from mouse epiblast share defining features with human embryonic stem cells. Nature 448, 196-199.

Theunissen et al: "Systematic Identification of Culture Conditions for Induction and Maintenance of Naive Human Pluripotency". Cell Stem Cell 2014

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tomoda, K., Takahashi, K., Leung, K., Okada, A., Narita, M., Yamada, N. A., Eilertson, K. E., Tsang, P., Baba, S., White, M. P., et al. (2012). Derivation conditions impact X-inactivation status in female human induced pluripotent stem cells. Cell Stem Cell 11, 91-99.

Tsakiridis, A., Huang, Y., Blin, G., Skylaki, S., Wymeersch, F., Osorno, R., Economou, C., Karagianni, E., Zhao, S., Lowell, S., et al. (2014). Distinct Wnt-driven primitive streak-like populations reflect in vivo lineage precursors. Development 141, 1209-1221.

Vallier, L., Alexander, M., and Pedersen, R. A. (2005). Activin/Nodal and FGF pathways cooperate to maintain pluripotency of human embryonic stem cells. J Cell Sci 118, 4495-4509.

Wang, W., Yang, J., Liu, H., Lu, D., Chen, X., Zenonos, Z., Campos, L. S., Rad, R., Guo, G., Zhang, S., et al. (2011). Rapid and efficient reprogramming of somatic cells to induced pluripotent stem cells by retinoic acid receptor gamma and liver receptor homolog 1. Proc Natl Acad Sci USA 108, 18283-18288.

Ware, C. B., Nelson, A. M., Mecham, B., Hesson, J., Zhou, W., Jonlin, E. C., Jimenez-Caliani, A. J., Deng, X., Cavanaugh, C., Cook, S., et al. (2014). Derivation of naive human embryonic stem cells. Proc Natl Acad Sci USA.

Watanabe, K., Ueno, M., Kamiya, D., Nishiyama, A., Matsumura, M., Wataya, T., Takahashi, J. B., Nishikawa, S., Nishikawa, S., Muguruma, K., et al. (2007). A ROCK inhibitor permits survival of dissociated human embryonic stem cells. Nat Biotechnol 25, 681-686.

Williams, R. L., Hilton, D. J., Pease, S., Willson, T. A., Stewart, C. L., Gearing, D. P., Wagner, E. F., Metcalf, D., Nicola, N. A., and Gough, N. M. (1988). Myeloid leukaemia inhibitory factor maintains the developmental potential of embryonic stem cells. Nature 336, 684-687.

Wray, J., Kalkan, T., and Smith, A. G. (2010). The ground state of pluripotency. Biochem Soc Trans 38, 1027-1032.

Yan, L., Yang, M., Guo, H., Yang, L., Wu, J., Li, R., Liu, P., Lian, Y., Zheng, X., Yan, J., et al. (2013). Single-cell RNA-Seq profiling of human preimplantation embryos and embryonic stem cells. Nat Struct Mol Biol 20, 1131-1139.

Ye, S., Li, P., Tong, C., and Ying, Q. L. (2013). Embryonic stem cell self-renewal pathways converge on the transcription factor Tfcp2l1. EMBO J 32, 2548-2560.

Ying, Q. L., Wray, J., Nichols, J., Batlle-Morera, L., Doble, B., Woodgett, J., Cohen, P., and Smith, A. (2008). The ground state of embryonic stem cell self-renewal. Nature 453, 519-523.

Young, R. A. (2011). Control of the embryonic stem cell state. Cell 144, 940-954.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R., et al. (2007). Induced pluripotent stem cell lines derived from human somatic cells. Science 318, 1917-1920.

Zhou, W., Choi, M., Margineantu, D., Margaretha, L., Hesson, J., Cavanaugh, C., Blau, C. A., Horwitz, M. S., Hockenbery, D., Ware, C., et al. (2012). HIF1alpha induced switch from bivalent to exclusively glycolytic metabolism during ESC-to-EpiSC/h ESC transition. EMBO J 31, 2103-2116.

The invention claimed is:

1. A method of resetting a human stem cell to a naive state, the method comprising:
   (a) providing a human stem cell to be reset,
   (b) inducing a naive state by
      (i) optionally introducing one or more heterologous reprogramming factors into the cell for expression thereof,
   (ii) culturing the cell in a resetting medium, wherein the resetting medium comprises a MEK inhibitor, a tankyrase inhibitor and a STAT3 activator,
   (c) sustaining the cell in a naive culture medium, wherein the naive culture medium is different from the resetting medium and comprises a MEK inhibitor, a PKC inhibitor, a GSK3 inhibitor, and a STAT3 activator,
thereby resetting a human stem cell to a naive state.

2. The method according to claim 1, wherein step (b)(i) is performed to reprogram the cell to a naive state and comprises expressing reprogramming factors in the cell, wherein the reprogramming factors comprise NANOG and KLF2.

3. The method according to claim 2, wherein the reprogramming factors consist of NANOG and KLF2.

4. The method according to claim 1, wherein the resetting medium further comprises the presence of a GSK3 inhibitor and/or an FGF inhibitor.

5. The method of claim 2, comprising expressing reprogramming factors in the cell, wherein the reprogramming factors comprise NANOG and KLF2, and culturing the cell in the resetting medium, wherein the resetting medium comprises a MEK inhibitor, and optionally either (i) a GSK3 inhibitor and a STAT3 activator, or (ii) a FGF inhibitor and a STAT3 activator.

6. The method according to claim 5, wherein expression of the reprogramming factors is transient.

7. The method according to claim 6, comprising introducing into the cell a plasmid preparation which expresses the reprogramming factors in the cell.

8. The method according to claim 6, wherein heterologous nucleic acid encoding the reprogramming factors is not maintained following reprogramming to the nave state.

9. The method according to claim 1, wherein step (b) (i) is not performed and the resetting medium further comprises a HDAC inhibitor.

10. The method of claim 1, wherein the resetting medium further comprises a HDAC inhibitor.

11. The method according to claim 1, wherein the naive culture medium further comprises a ROCK inhibitor.

12. The method according to claim 1, wherein
(i) the GSK3 inhibitor is CHIR99021;
(ii) the MEK inhibitor is PD0325901;
(iii) the PKC inhibitor is Gö6983 or Ro-31-8425;
(iv) the STAT3 activator is LIF, which is optionally human LIF; or
(v) the tankyrase inhibitor is XAV939.

13. The method according to claim 1, wherein
(i) the cells are cultured in an FGF supplemented serum replacement medium prior to inducing the naive state in step (b)(i),
(ii) the resetting medium or naive culture medium of step (b)(ii) or step (c), respectively is replaced daily, or
(iii) the resetting is performed in the presence of 5% oxygen.

14. The method according to claim 1, wherein maintenance in a nave state is confirmed by one of more of the following phenotypes or genotypes:
a) the ability to continuously and clonally self-renew in culture and retain pluripotency;
b) a global transcriptome more similar to that of mouse embryonic stem cells cultured in defined media than to mouse post-implantation epiblast stem cells (EpiSCs) or conventional human pluripotent stem cells;
c) a global transcriptome more similar to pre-implantation epiblast than post-implantation epiblast;
d) expression of mRNA and protein of pre-implantation epiblast specific transcription factors, optionally 1, 2, 3, 4, 5, 6 or all of: KLF2, KLF4, TFCP2L1, TBX3, REX1, GBX2 and STELLA (DPPA3), and expression of mRNA and protein of general pluripotency factors, such as OCT4, SOX2 and SALL4, and optionally elevated mRNA and protein levels of NANOG;
e) reliance on critical transcription factors defined in mouse embryonic stem cells, particularly TFCP2L1 and KLF4;
f) nuclear localisation of TFE3;
g) low level expression or absence of expression of early lineage markers that are typically expressed in convention human pluripotent stem cells, such as AFP, EOMES and/or BRACHURY;
h) active mitochondrial respiration;
i) genome-wide hypomethylation;
j) lower levels of histone modifications associated with gene, such as reduced levels of H3K27me3 and H3K9me3;
k) capable of incorporation into a host embryo inner cell mass and a pre-implantation epiblast to form embryo chimaeras;
l) able to colonise a post-implantation epiblast and derivative tissues in chimaeras formed with the same, or closely related, species;
m) self-renewal in the presence of complete inhibition of Erk/MAP kinase signalling;
n) self-renewal in the presence of growth factor receptor tyrosine kinase signalling inhibition;
o) self-renewal in the presence of TGFbeta/activin signalling inhibition;
p) self-renewal in the presence of PKC inhibition or knockdown;
q) self-renewal in the presence of partial inhibition of (GSK3) glycogen synthase kinase-3 activity;
r) self-renewal in the presence of STAT3 agonists, such as LIF;
s) self-renewal from dissociated single cells with or without Rho associated kinase inhibition (ROCKi);
t) self-renewal in the absence of serum or serum substitutes;
u) self-renewal in the absence of feeder cells;
v) self-renewal in the absence of transgene expression or other genetic perturbation;
w) retention of diploid karyotype without rearrangement in long-term passaging, for example over more than 40 population doublings;
x) differentiation into conventional primed pluripotent phenotype in the presence of growth factor stimulation of Erk/MAP kinase signalling and activin;
y) able to differentiate in vitro into primordial germ cells as well as somatic germ layers;
z) able to establish continuous culture in vitro by transition from a pre-implantation epiblast;
aa) tightly packed domed appearance; and/or
bb) reduction in expression of DNMT3a and DNMT3b.

15. The method according to claim 14, wherein expression of KLF2, KLF4, TFCP2L1, TBX3, REX1, GBX2 and STELLA is induced in the reprogrammed cells.

16. The method according to claim 5, wherein the human stem cell to be reset in step (a) is selected from:
(i) an induced pluripotent stem cell;
(ii) a cell from an embryonic cell line; or
(iii) an embryonic stem cell obtained by biopsy without destruction of the respective embryo.

17. The method according to claim 1, wherein the resetting medium comprises a PKC inhibitor.

18. The method of claim 4, wherein the FGF inhibitor is PD173074.

* * * * *